(12) United States Patent
Maruyama et al.

(10) Patent No.: US 7,414,111 B2
(45) Date of Patent: Aug. 19, 2008

(54) ENGINEERED TEMPLATES AND THEIR USE IN SINGLE PRIMER AMPLIFICATION

(75) Inventors: Toshiaki Maruyama, La Jolla, CA (US); Katherine S. Bowdish, Del Mar, CA (US); Shana Frederickson, Solana Beach, CA (US); Mark Renshaw, San Diego, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 549 days.

(21) Appl. No.: 10/737,252

(22) Filed: Dec. 15, 2003

(65) Prior Publication Data

US 2004/0175736 A1 Sep. 9, 2004

Related U.S. Application Data

(63) Continuation-in-part of application No. 10/251,085, filed on Sep. 19, 2002.

(60) Provisional application No. 60/323,455, filed on Sep. 19, 2001.

(51) Int. Cl.
*C07K 16/00* (2006.01)

(52) U.S. Cl. ............... 530/387.1; 530/387.3; 530/388.1; 530/861

(58) Field of Classification Search ........................ None
See application file for complete search history.

(56) References Cited

U.S. PATENT DOCUMENTS

| | | | |
|---|---|---|---|
| 4,582,788 A | 4/1986 | Erlich | |
| 4,683,194 A | 7/1987 | Saiki et al. | |
| 5,130,238 A | 7/1992 | Malek et al. | |
| 5,508,178 A | 4/1996 | Rose et al. | |
| 5,595,891 A | 1/1997 | Rose et al. | |
| 5,658,727 A | 8/1997 | Barbas et al. | |
| 5,679,512 A | 10/1997 | Lancy et al. | |
| 5,683,879 A | 11/1997 | Lancy et al. | |
| 5,744,308 A | 4/1998 | Guillou-Bonnici et al. | |
| 5,962,272 A | 10/1999 | Chenchik et al. | |
| 6,251,639 B1 | 6/2001 | Kurn | |
| 6,291,158 B1 | 9/2001 | Winter et al. | |
| 6,291,159 B1 | 9/2001 | Winter et al. | |
| 6,291,160 B1 | 9/2001 | Lerner et al. | |
| 6,291,161 B1 | 9/2001 | Lerner et al. | |
| 6,403,319 B1 | 6/2002 | Lizardi et al. | |

FOREIGN PATENT DOCUMENTS

| | | |
|---|---|---|
| EP | 0050424 | 9/1985 |
| EP | 0084796 | 5/1990 |
| EP | 0237362 | 3/1992 |
| EP | 0201184 | 12/1992 |
| EP | 0258017 | 6/1997 |
| WO | WO 96/41012 | 12/1996 |
| WO | WO 9914226 | 3/1999 |
| WO | WO 00/08208 | 2/2000 |
| WO | WO 00/66779 | 11/2000 |
| WO | WO 01/06004 | 1/2001 |
| WO | WO 01/55454 | 8/2001 |

OTHER PUBLICATIONS

Moreno de Alboran, I et al. Immunotechnology [1995] 1(1):21-28.*
Kuhn et al, "DNA Helicases", Cold Spring Harbor Laboratory, pp. 63-67 (1978).
Mullis et al., Specific Enzymatic Amplification of DNA in Vitro: The Polymerase Chain Reaction, Cold Spring Harbor Symposia on Quantitative Biology, vol. LI, pp. 263-273 (1986).
Ørum, et al., "Efficient method for constructing comprehensive murine Fab antibody libraries displayed on phage", Nucleic Acids Research, 21(19) pp. 4491-4498 (1993).
Patel et al., "Formation of Chimeric DNA Primer Extension Products by Template Switching onto an Annealed Downstream Oligonucleotide", Proc. Natl. Acad. Sci., USA, 93, pp. 2969-2974 (1996).
Redding, Homologous Pairing and Strand Exchange in Genetic Recombination, Ann. Rev. Genet., 16: pp. 405-437 (1982).
Zheleznaya, et al., "PCR Fragmentation of DNA", Biochemistry, 64(4), pp. 373-378 (1999).
Ayala et al., "New Primer Strategy Improves Precision of Differential Display," *Biotechniques,* 18(5): 842-844, 846, 848 and 850 (1995).
Cheung and Nelson, "Whole Genome Amplification Using a Degenerate Oligonucleotide Primer Allows Hundreds of Genotypes to be Performed on Less than One Nanogram of Genomic DNA," *Proceedings of the National Academy of Sciences of USA,* 93:14676-14679 (1996).

(Continued)

*Primary Examiner*—Christina Chan
*Assistant Examiner*—F. Pierre VanderVegt
(74) *Attorney, Agent, or Firm*—Ropes & Gray, LLP

(57) ABSTRACT

Methods of amplifying nucleic acid have now been discovered which include the steps of: a) annealing a primer to a template nucleic acid sequence, the primer having a first portion which anneals to the template and a second portion of predetermined sequence; b) synthesizing a polynucleotide that anneals to and is complementary to the portion of the template between the location at which the first portion of the primer anneals to the template and the end of the template, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide and a second portion having the same predetermined sequence as the second portion of the primer; e) extending the polynucleotide synthesized in step (b) to provide a terminal portion thereof that is complementary to the predetermined sequence; and f) amplifying the extended polynucleotide using a single primer having the predetermined sequence. In particularly useful embodiments, the methods are used to amplify a repertoire of IgA antibodies.

2 Claims, 14 Drawing Sheets

OTHER PUBLICATIONS

Froussard, "A Random-PCR Method (rPCR) Construct Whole cDNA Library from Low Amounts of RNA," *Nucleic Acids Research*, 20(11):2900 (1992).

Little et al., "Generation of a Large Complex Antibody Library from Multiple Donors," *Journal of Immunological Methods*, 231(1-2):3-9 (1999).

Roux and Dhanarajan, "A Strategy for Single Site PCR Amplification of dsDNA: Priming Digested Cloned or Genomic DNA from an Anchor-Modified Restriction Site and a Short Internal Sequence," *Biotechniques*, 8(1):48-57 (1990).

Telenius et al., "Degenerate Oligonucleotide-Primed PCR: General Amplification of Target DNA by a Single Degenerate Primer," *Genomics*, 13:718-725 (1992).

* cited by examiner

Fig. 3

$2^{nd}$ strand cDNA synthesis on $1^{st}$ strand cDNA by a primer that has a first portion that hybridizes to the variable region of an antibody gene and a second portion with a predetermined sequence

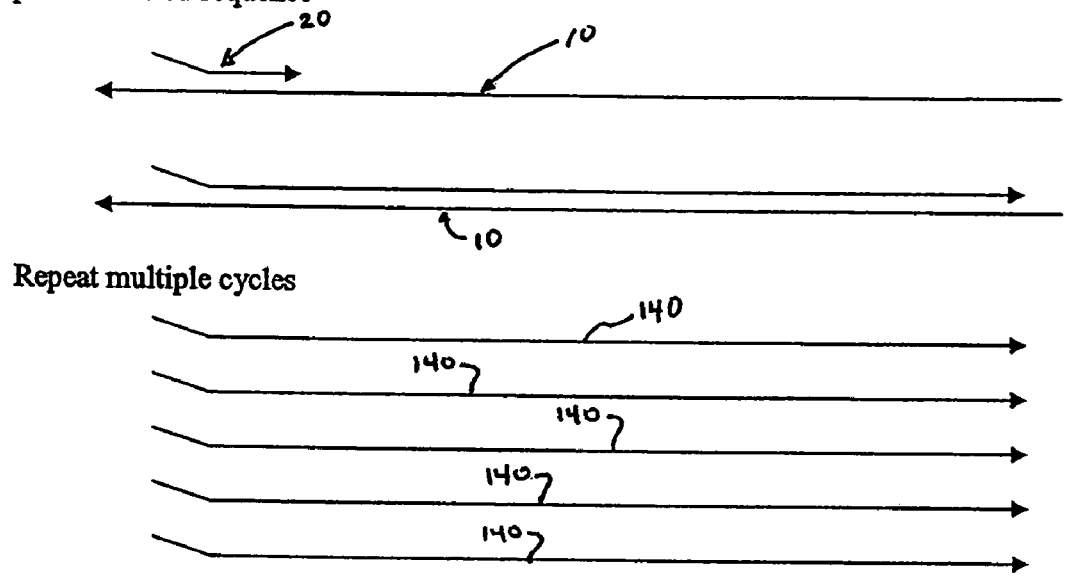

Repeat multiple cycles

Hybridize a restriction oligonucleotide on the desired position in the constant region of an antibody gene and digest with an appropriate restriction enzyme (RED)

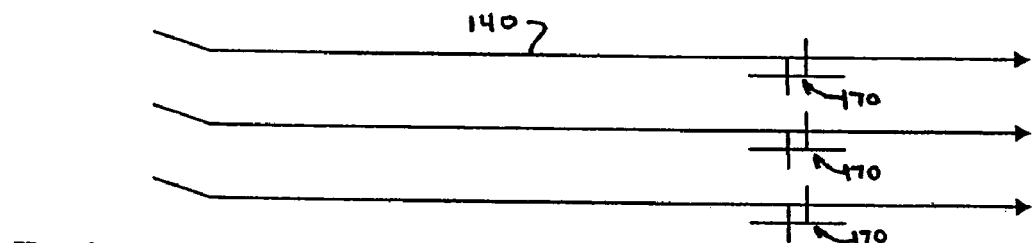

Heat denature and add nested oligo nucleotide and perform nested oligonucleotide extension reaction (NOER)

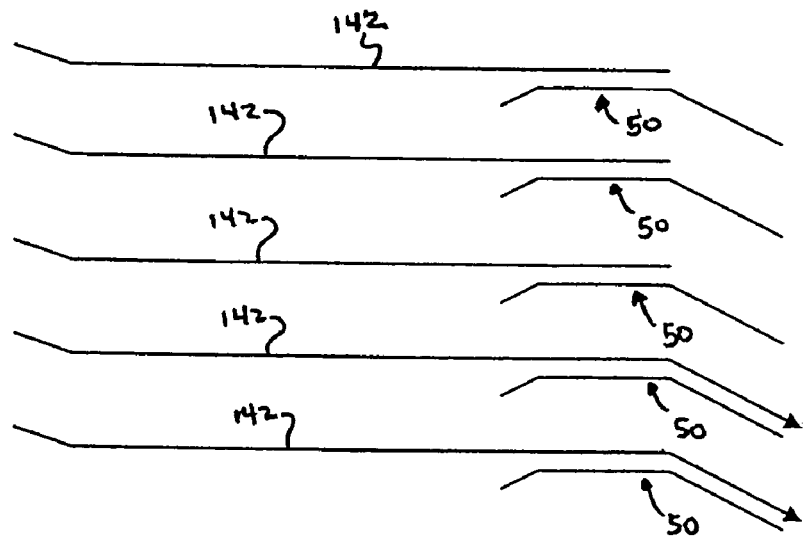

IgG kappa clones

Heavy chain

| Fab | framework 1 | CDR1 | framework 2 | CDR2 | |
|---|---|---|---|---|---|
| HBPAXK1a | EVQLVESGGGLVQPGGSLRLSCAASGFTFG | S--YTMN | WVRQAPGKGLEWIS | YIST--TSSSIYYADSVKG | VH3 |
| HBPAXK1b | Q•••L••••V••••T••T••T•••••••• | •••••• | •••••••••••••• | •••••••••••••••••• | VH3 |
| HBPAXK1c | Q•••••••••••••T••T••T•••••••• | •••••• | •••••••••••••• | •••••••••••••••••• | VH3 |
| HBPAX1Kd | •••L••••••••••••••••••••••••• | •••••• | •••••••••••••• | •••••••••••••••••• | VH3 |
| HBPAXK2a | EVQLVESGGGLVQPGGSLRLSCAASGFTLS | S--SAMS | WVRQAPGKGLEWVS | VNSG--NGFSTYYADSVKG | VH3 |
| HBPAXK2b | Q••••••••••••••••••••V••••••• | •••••• | •••••••••••••• | ••••S••••••••••••• | VH3 |
| HBPAXK2c | Q••••••••••••••••••••••••••••• | •••••• | •••••••••••••• | •••••••••••••••••• | VH3 |
| HBPAXK2d | •••L••••••••••••••••••••••••• | •••••• | •••••••••••••• | •••••••••••••••••• | VH3 |
| HBPAXK2e | •••••••••••••••••••••••••••••• | •••••• | •••••••••••B•• | •••••••••••••••••• | VH3 |
| HBPAXK3a | EVQLLESGGGLVQPGGSLRLSCAASGFTFS | S---SAMS | WVRQAPGKGLEWVS | VISG--NGFSTYYADSVKG | VH3 |
| HBPAXK3b | •••V•••••••••••••••••••V••••• | •••••• | •••••••••••••• | •••••••••••••••••• | VH3 |
| HBPAXK4a | QMQLVQSGAEVKKPGASVKVSCKASGYTFS | D--YFMH | WVRQAPGBGLEWMG | LVNP--TNGYTAYAPKFQG | VH1 |
| HBPAXK4b | •••V•••••••••••••••••••••••••• | •••••• | •••••••••Q•••• | •••••••••••••••••• | VH1 |
| HBPAXK5 | QVQVVQSGAEVKKPGASVKVSCKASGYTFT | S--YGIC | WVRQAPGQSLEWMG | WIST--YNGNTNYAQKLQG | VH1 |
| HBPAXK6 | EVQLLESGGGLVQPGGSLRLSCAASGFTER | N--YAMS | WVRQPPGKGLEWVT | AISG--DVVDFYYADSVQG | VH3 |
| HBPAXK7a | QVQLQESGPGLVKPSETLSLTCTVSGGSIS | SLMYFWG | WIRQPPGKGLEWIG | SIY--YSGTAYYNPSLRS | VH4 |
| HBPAXK7b | •V•••A•••••••••••••••••••••• | •V•••A | ••••S••••••••• | •••••••••••••••••• | VH4 |
| HBPAXK7c | •••••••••••••••••••••••••••••• | •A•••• | •••••••••••••• | ••••T•••••••••••• | VH4 |
| HBPAXK7d | •L•••••••••••••••••••••••••••• | •••••• | ••••S••••••••• | •••••••••••••••••• | VH4 |
| HBPAXK7e | •••••••••••••••••••••••••••••• | •••••• | •••••••••••••• | •••••••••••••••••• | VH4 |
| HBPAXK8 | QMQLVQSGGGVLAEVGGSLRLSCAVSGLTFN | N--AWMN | WVRQAPGRGLECVG | RIKSKIDGGTTDYATPVKG | VH3 |
| HBPAXK9a | EVQLVESGGGLVRPGGSLRLSCAASGFTFS | R--YTLS | WVRQAPGKGLEWVS | YIST--DGSTIYYADSVKG | VH3 |
| HBPAXK9b | Q•••••••••••••••••••••••••••• | •••••• | •••••••••••••• | •••••••••••••••••• | VH3 |
| HBPAXK10 | EVQLVQSGAEVGKPGASVKVSCGASGYSFT | A--YYMH | WVRQAPGQGLQVMG | WITP--DNGRTNYAQQFQR | VH1 |
| HBPAX11 | QVQLVESGGVVQPGGSLRLSCAASGFTFD | D--YAMH | WVRQVPGKGLEWVS | LISW--DAISTYYADSVKG | VH3 |

| Fab | framework 3 | CDR3 / DH / JH | JH | |
|---|---|---|---|---|
| HBPAXK1a | RFSISRDNAKNSLYLQMNSLRDEDTAVYYCAR | VFFVEGS----------YWSFDLWGRGTLVTVSS | JH2 | (Seq. ID No. 83) |
| HBPAXK1b | •••••••••••••••••••••••••••••• | •••••••••••••••••••••••••••••• | JH2 | (Seq. ID No. 84) |
| HBPAXK1c | •••••••••••••••••••••••••••••• | •••••••••••••••••••••••••••••• | JH2 | (Seq. ID No. 85) |
| HBPAX1Kd | •••••••••••••••••••••••••••••• | •••••••••••••••••••••••••••••• | JH2 | (Seq. ID No. 86) |
| HBPAXK2a | RFSISRDNSKNTLYLQMNSLRAEDTAKYYCVK | VKYGSRSHFF------FDRWGQGTLVTVSS | JH5 | (Seq. ID No. 87) |
| HBPAXK2b | •••••••••••••••••••••••••••••• | •••••••••••••••••••••••••••••• | JH5 | (Seq. ID No. 88) |
| HBPAXK2c | •••••••••••••••••••••••••••••• | •••••••••••••••••••••••••••••• | JH5 | (Seq. ID No. 89) |
| HBPAXK2d | •••••••••••••••••••••••••••••• | •••••••••••••••••••••••••••••• | JH5 | (Seq. ID No. 90) |
| HBPAXK2e | •••••••••••••••••••••••••••••• | •••••••••••••••••••••••••••••• | JH5 | (Seq. ID No. 91) |
| HBPAXK3a | RFSISRDNKNTLYLQMNSLRAEDTAEYYCAN | VKYGSGSHF---------WFDPWGQGTLVTVSS | JH5 | (Seq. ID No. 92) |
| HBPAXK3b | •••••••••••••••••••••••••••••• | •TK•••••••••••••••••••••••••••• | JH5 | (Seq. ID No. 93) |
| HBPAXK4a | RVTMTRQRPTSTVMELRSSLRSEDTAVYFCAR | VRSSDSI-------DAPDIWGQGTMVTVSS | JH3 | (Seq. ID No. 94) |
| HBPAXK4b | •••••••••••••••••••••••••••••• | ••K••••••••••••••••••••••••••• | JH3 | (Seq. ID No. 95) |
| HBPAXK5 | RVTMTTDTSTSTAYMELRSSLRSDDTAVYYCAR | AWPPRGSSQLDR----GQYFQHWGQGTLVTVSS | JH1 | (Seq. ID No. 96) |
| HBPAXK6 | RFIISRDNSKNMLYLEMKSLRAEDTAVYYCAK | DYGAYDILTGKLLDYYQYGMDVWGQGTTVTVSS | JH6 | (Seq. ID No. 97) |
| HBPAXK7a | RATISVDTSKNQLSLKLMSVTAADTAVYYCAR | PSSFYFNGRTSYYPGET-AFEIWGQGTTVAVSS | JH3 | (Seq. ID No. 98) |
| HBPAXK7b | •V•M••••••••••••••••••••••••• | ••T•Y•••S•T•••••A•••D•••••T••• | JH3 | (Seq. ID No. 99) |
| HBPAXK7c | •VS••••••••••••••••R•I•••••••• | ••••A••••••••G•T•••••••V••••• | JH3 | (Seq. ID No. 100) |
| HBPAXK7d | •V•M•••••••••••••••••S•••••••• | ••••••••••••••••A•••D•••••M•T••• | JH3 | (Seq. ID No. 101) |
| HBPAXK7e | •V••••••••••••••••••••••••••• | •••••••••••••••••••••••••••••• | JH3 | (Seq. ID No. 102) |
| HBPAXK8 | RFTISRDDSKNMVLQMNSLRIEDTAVYYCTT | RPNPWQSPAFW---------DPWGQGTLVTVSS | JH4 | (Seq. ID No. 103) |
| HBPAXK9a | RFTISRDNAKNSLSLQMISLRDEDTAVYYCAR | VFPGGNFRA----HWYFDLWGRGTLVTVSS | JH2 | (Seq. ID No. 104) |
| HBPAXK9b | •••••••••••••••••••••••••••••• | ••K••••••••••••••••••••••••••• | JH2 | (Seq. ID No. 105) |
| HBPAXK10 | RLTLTSDTSINTYYLEMKSLKSDDTAVYYCVR | SGWSQP----LDYWGQGTLVTVSS | JH4 | (Seq. ID No. 106) |
| HBPAX11 | RFTTSRDNKKNFLYLQMDSLTPEDTALYYCGK | DQGGRFRL-----VDYWQGGTLVTVSS | JH4 | (Seq. ID No. 107) |

Fig 8a

| Fab | Clone | framework 1 | CDR1 | framework 2 | CDR2 | |
|---|---|---|---|---|---|---|
| | | EIVMTQSPAALSVSPGERATLSC | RASQSISS------SLA | WYQQKPGQAPRLLIY | AASTRAT | |
| HBPAXK1a | 3A1 | ·················· | ·········N·· | ················ | G······ | VK3 |
| HBPAXK1b | 3A2 | ·····T······T······ | ····V·······N·· | ·······R···G···P | GT····P | VK3 |
| HBPAXK1c | 3A3 | ·····F··T··A······· | ·······T·NN·· | ·······S········ | ·······S | VK3 |
| HBPAXK1c | 3A8 | ·····T······S······ | ·····N·R·· | ················ | ·T·····A | VK3 |
| HBPAXK1c | 3G6 | ·····T······TT····· | ····H·VT··· | ················ | ·T·····A | VK3 |
| HBPAXK1d | 3C11 | ·····T·············· | ···G··V····· | ···········H···· | ········ | VK3 |
| HBPAXK1d | 3F4 | W···················· | W··V·······D·· | ···········H···· | ········ | VK3 |
| HBPAXK2a | 3A4 | ·····T·············· | ········G·····Y·· | ················ | G······ | VK3 |
| HBPAXK2b | 3A5 | ···L·T·A··········· | ····VN··· | ···········N·· | G······ | VK3 |
| HBPAXK2c | 3A6 | ·····T·············· | ····V···· | ···········N·· | ········ | VK3 |
| HBPAXK2c | 3B8 | ············V····· | G····V···· | ···········N·MS | G······ | VK3 |
| HBPAXK2c | 3B10 | ···················· | ·····V···· | ···········N·· | GS····· | VK3 |
| HBPAXK2c | 3E10 | ·····T······D······ | ····V·T··· | ···········NV· | ········ | VK3 |
| HBPAXK2c | 3H9 | ···················· | ·····V···· | ···········N·· | ········ | VK3 |
| HBPAXK2d | 3A9 | ·····T·············· | ····V···· | ···········NL· | G······ | VK3 |
| HBPAXK2d | 3A12 | ·····T·····EQ····· | ····V···· | ···········NL· | ········ | VK3 |
| HBPAXK2d | 3B4 | ·····T······EQ····· | ····V···· | ···········NL· | ·····M·D | VK3 |
| HBPAXK2d | 3C1 | ·····T·············· | ····V···· | ···········N·· | ········ | VK3 |
| HBPAXK2d | 3D12 | ·····T·············· | ····V···· | ···········N·· | GT····· | VK3 |
| HBPAXK2d | 3G4 | ·····VS·FL···V···· | ····VRG·· | ············P·· | ·······N | VK3 |
| HBPAXK3a | 3B1 | ···················· | ····V·T··· | ···········N·· | ········ | VK3 |
| HBPAXK3b | 3C6 | D·········EA······· | ····V·N··· | ············H·· | ········ | VK3 |
| HBPAXK4a | 3B3 | D·QL···ST·A·V·D·V·IT· | ········· | ·········K··K·· | Q··SLQS | VK1 |
| HBPAXK4b | 3F2 | D·QL···ST·A·V·D·V·IT· | ···RD·KT·· | ·········K··K·· | D··SLES | VK1 |
| HBPAXK5 | 3B6 | ·····T······T······ | ····V·····S | ················ | G······ | VK3 |
| HBPAXK6 | 3C7 | ···L·····GT··L····· | ····V·····S | ················ | G···S·· | VK3 |
| HBPAXK7a | 3D1 | ···L·····GT··L····· | ····VN·K···F | ·········R··P·· | G··NT·· | VK3 |
| HBPAXK7b | 3D3 | ···L·····GT··L····· | ····V·····S | ················ | G···S·· | VK3 |
| HBPAXK7b | 3F5 | ···L·····GT··L····· | ·····I···· | ················ | ST····· | VK3 |
| HBPAXK7c | 3D7 | ···L·····GT··L····· | ····FGNN··· | ··········RL··· | G···S·· | VK3 |
| HBPAXK7d | 3E1 | D······DS·A··L····· | KS··VLYSSNNKNN·· | ·········P·K··· | W····ES | VK4 |
| HBPAXK7e | 3E8 | ·····S············· | ·········N·· | ················ | G··N··· | VK3 |
| HBPAXK8 | 3D9 | D······DS···L····N· | KS··NVLYSSNNKNY·· | ·········P·K··· | W··A·ES | VK4 |
| HBPAXK9a | 3E3 | ···L·····T··L····· | ····GV···· | ············Q·· | D··N··· | VK3 |
| HBPAXK9b | 3E7 | ···L·····T··L····· | ·····Y···· | ················ | D··N··· | VK3 |
| HBPAXK9b | 3G5 | ···L·····T··L····· | ·····Y···· | ················ | D··N··· | VK3 |
| HBPAXK10 | 3F10 | D·M····ES·A··L····IY· | KS··T·L·SRNNQKY·· | ·········A·HP·K·· | B··S·ES | VK4 |
| HBPAXK11 | 3G8 | D·QL····SS·A·V·D·VSIT· | ····D··N·····Y·V | ·····F·······K··KS·· | ···SLQG | VK1 |

IgG lambda clones

| Fab | | framework 1 | CDR1 | framework 2 | CDR2 | |
|---|---|---|---|---|---|---|
| HBL1 | 3D11 | LEEVQLLESGGGLVHPGGSLRLSCAASGFRFG | SYAMS | WVRQAPGKGLEWVS | SISGSGDTIYYADSVRG | |
|  | 3C12 | LEEVQLLESGGGLVHPGGSLRLSCAASGFRFG | SYAMS | WVRQAPGKGLEWVS | SISGSGDTIYYADSVRG | |
|  | 3D9 | LEEVQLLESGGGLVHPGGSLRLSCAASGFRFG | SYAMS | WVRQAPGKGLEWVS | SISGSGDTIYYADSVRG | |
| HBL2a | 3B5 | LEEVQLLESGGGLVQPGGSLRLSCAASGFRFS | SYGMS | WVRQAPGKGLEWVS | GISGSSGSTHYADSVKG | |
| HBL2b | 3B8 | LEEVQLLESGGGLVQPGGSLRLSCAASGFRFT | SYGMS | WVRQAPGKGLEWVS | GISGNGGRIYYADSVKG | |
|  | 3C6 | LEEVQLLESGGGLVQPGGSLRLSCAASGFRFT | SYGMS | WVRQAPGKGLEWVS | GISGNGGRIYYADSVKG | |
| HBL2c | 3B9 | LEEVQLLESGGGLVQPGGSLRLSCAASGFRFS | SYGMS | WVRQVPGKGLEWVA | GITGNSGKIYYADSVKG | |
| HBL2d | 3C4 | LEEVQLLESGGGLVQPGGSQRLSCAASGFTFR | SYGMS | WYRQAPGKGLEWVS | GLSGSSGRIYYADSVKG | |
| HBL3 | 3B10 | LEQVQLVESGGGVVQPGGSLRLSCAASGFTFR | NYGMH | WVRQAPGKGLEWVA | YILYDGSKKYYVDSVKG | |
| HBL4a | 3C11 | LEQVQLVESGGGVVQPGRSLRLSCAASGVRFS | SYGMH | WVRQAPGKGLEWVA | SISSDATKKNYADSVKG | |
|  | 3D6 | LEQVQLVESGGGVVQPGRSLRLSCAASGVRFS | SYGMH | WVRQAPGKGLEWVA | SISSDATKKNYADSVKG | |
| HBL4b | 3E5 | LEQVQLVQSGGGVVQPGGSLRLSCAASGVTFR | SYGMH | WVRQAPGKGLEWVA | FVSSDGNKKNYADSVKG | |
| HBL4c | 3E8 | LEEVQLVESGGGVVQPGRSLRLSCAASRLSFT | SYGMH | WVRQAPGKGLEWVA | SISSDGNKKNYADSVKG | |
| HBL4d | 3E12 | LEQVQLVESGGGVVQPGRSLRLSCAASGLTFS | SYGMH | WVRQAPGKGLEWVA | FISYDGNNKKYADSVKG | |
| HBL5 | 3D1 | LEEVQLLESGGGLVQPGGSLRISCAGSGFRFG | SYAMS | WVRQAPGKGLEWIS | GIVGTGGDTKYGDSVKG | |
| HBL6 | 3F10 | LEEVQLLESGGGLVQPGGSLRLSCAASGFSSS | AYALS | WVRQIPGKGLEWVA | AISGGGGSTYYADSVEG | |
| HBL7 | 3G5 | LEQVQLVESGGGLVQPGGSLRLSCAASGFTFS | RYDIH | WVRQAPGKGLEWVA | LISYDGMYKSSADSVKG | |

| Fab | | framework 3 | CDR3 DH | JH | | |
|---|---|---|---|---|---|---|
| HBL1 | 3D11 | RFTISKDSSRNTLFLQLNSLRVDDTAVYYCAK | GSIFGTAKVYG | VDYWGQGALVTVSS | (Seq. ID No. 146) |
|  | 3C12 | RFTISKDSSRNTLFLQLNSLRVDDTAVYYCAK | GSIFGTAKVYG | VDYWGQGTLVTVSS | (Seq. ID No. 147) |
|  | 3D9 | RFTISKDSSRNTLFLQLNSLRVDDTAVYYCAK | GSIFGTAKVYG | VDYWGQGTLVTVSS | (Seq. ID No. 148) |
| HBL2a | 3B5 | RFIISRDNSKNTLYLQMDSLRADDTAVYYCAK | DGYYGSGLFYG | MDVWGQGTTVTVSS | (Seq. ID No. 149) |
| HBL2b | 3B8 | RFIISRDNSKNTLYLQMDSLRADDTAVYYCAK | DGYYGSGVFYG | MDVWGQGTTVTVSS | (Seq. ID No. 150) |
|  | 3C6 | RFIISRDNSKNTLYLQMDSLRADDTAVYYCAK | DGYYGSGVFYG | MDVWGQGTTVTVSS | (Seq. ID No. 151) |
| HBL2c | 3B9 | RFIISRDNSKNTLYLQMNSLRAEDTAVYYCAK | DGYYGSGSFYG | IDVWGQGTTVTVSS | (Seq. ID No. 152) |
| HBL2d | 3C4 | RFIISRDNSKNTLYLQMNSLRAEDTAVYYCAK | DGLLAGGYEGG | FDYWGQGTLVTVSS | (Seq. ID No. 153) |
| HBL3 | 3B10 | RFTVSRDNSQNTLYLQMNSLRPEDTAVYYCVK | DGYYGSGLLYG | IDYWGQGTTVAVSS | (Seq. ID No. 154) |
| HBL4a | 3C11 | RFTISRDNSKNTLHLHLQMVTLRPEDTAVYYCAK | TDILGPAIEFG | LDYWGQGTLVTVSS | (Seq. ID No. 155) |
|  | 3D6 | RFTISRDNSKNTLYLQMISLRREDTAVYYCAK | TDILGPAIEFG | LDYWGQGTLVTVSE | (Seq. ID No. 156) |
| HBL4b | 3E5 | RFTISRDNSKNTLYLQMISLRREDTAVYYCAK | TDILGPAIEFG | LDYWGQGTLVTVSP | (Seq. ID No. 157) |
| HBL4c | 3E8 | RFTISRDNSKNTLSLQMIGLRREDTAVYYCAK | TDILGPAIEFG | LDYWGQGTLVTVSP | (Seq. ID No. 158) |
| HBL4d | 3E12 | RFTISRDNSKNRLFLQMVSLRREDTAVYYCAK | TDILGPAIEYG | LDYWGQGTLVTVSS | (Seq. ID No. 159) |
| HBL5 | 3D1 | RFTISRDNSKNVVYLQMNGLRVEDTAVYYCAK | SAYYVSGSYYG | FDYWGQGTRVTVSS | (Seq. ID No. 160) |
| HBL6 | 3F10 | RFTISRDNSKNTLYLQMNSLRGEDTAAYYCAT | GNYGRNVQNWY | FDLWGRGTLVTVSP | (Seq. ID No. 161) |
| HBL7 | 3G5 | RFTVSRENSRNTVFLQMSGLRPEDTAVYFCAK | SDVMARARGSG | FDVWGQGTTVTVSS | (Seq. ID No. 162) |

Fig 8d

Light chain

| Fab | | framework 1 | CDR1 | framework 2 | CDR2 |
|---|---|---|---|---|---|
| HBL1 | 3D11 | SRSYELTQPPSVSVAPGQTARITC | GGNTIGSQSVH | WYQQKPGQAPVLVVY | DDSDRPS |
| | 3C12 | SRSYVLTQPPSVSVAPGQTASIAC | GGNNIGSKSKS | WYQQKPGQAPVLVVY | DDTDRPS |
| | 3D9 | SRSYELTQPPSVSVAPRTDGQITC | GEDKIESKSVH | WYQQKPGQAPVLVVY | DDSDRPS |
| HBL2a | 3B5 | SRLPVLTQPPSVSVAPGQTATITC | GGNNIGSKSVH | WFQQKPGQAPVLVVY | DDNERPS |
| HBL2b | 3B8 | SRSYVLTQPPSVSVAPGQTARITC | GGDSIGSKSVH | RYQQKPGQAPVLVVY | DDSDRPS |
| | 3C6 | SRSYVLTQPPSVTVPGQTARITC | GGNNIGSKSVH | WYQQKPGQAPVLVVY | DDSDRPS |
| HBL2c | 3B9 | SRSYELTQPPSVSVAPGQTARIAC | GGNNIGSRSVH | WYQQKPGQAPVLVVY | DDSDRPS |
| HBL2d | 3C4 | SRLPVLTQPPSVSVAPGQTARITC | GGNNIGSKSVH | WYQQKPGQAFLLLVY | DDSDRPS |
| HBL3 | 3B10 | SRSYVLTQPPSVSVAPGQTARITC | GGNNIGAKSVQ | WYQQRPGQAPLMVVY | DDTERPS |
| HBL4a | 3C11 | SRQSVLTQPPSVSVAPGQTARITC | GGNNIGSKSVH | WYQQKPGQAFVLAVY | DDSDRPS |
| | 3D6 | SRSYVLTQPPSVSVAPGQTARIAC | GGDNIGIKTVQ | WYQQKPGQAPVLVVH | DDSDRPS |
| HBL4b | 3E5 | SRQPVLTQPPSVSVAPGQMARITC | GGNNIGRQSVN | WYQQKPGQAPVLVVY | DDSDRPS |
| HBL4c | 3E8 | SRSYELTQPPSVSVAPGQTARITC | GGNNIGSKSVH | WYQQKPGQAPVLVVY | DDSDRPF |
| HBL4d | 3E12 | SRLPVLTQPPSVSVAPGQTASIAC | GGDNIGSKSVH | WYQKAGQAPVLVVY | DDNDRPS |
| HBL5 | 3D1 | SRSYVLTQPPSVSVAPGQTARITC | GGNSIGSKSVH | WYQQKPGQAPVLVVY | DDSDRPS |
| HBL7 | 3G5 | SRQAVLTQPPSVSVAPGQTARITC | GGNNIGSKSAH | WYQQRPGQAPLLVVY | DDSDRPS |

| Fab | | framework 3 | CDR3 | JL | |
|---|---|---|---|---|---|
| HBL1 | 3D11 | GIPERFSGSNSGNTATLTISRVEAGDEADYYC | QVWDSSSDH--- | VVFGGGTRLTVL | (Seq. ID No. 163) |
| | 3C12 | GIPERFSGSNSGNTATLTISRVEAGDEADYYC | QVWDASSDQPY- | VVFGGGTRLTVL | (Seq. ID No. 164) |
| | 3D9 | GIPERISGSNSGNTATLIISRVTTSRVEAGTT | QVWDSSSHH--- | VVFGGGTKLTVL | (Seq. ID No. 165) |
| HBL2a | 3B5 | GIPBRFSGSNSGNTATETISRVEAGDEADYYC | QVWHITSDHPN- | VIFGGGTKLTVI | (Seq. ID No. 166) |
| HBL2b | 3B8 | GIPERFSGSNSGNTATLSISRVEAGDEADYYC | QLWDTNNDH--- | VVFGGGTKLTVI | (Seq. ID No. 167) |
| | 3C6 | GIPERFSGSNSGNTATLTISRVEAGDEADYHC | HVWDSSGDLPD- | VVFGGGSKLTVI | (Seq. ID No. 168) |
| HBL2c | 3B9 | GIPERFSGSNSGNTATLTISRVEAGDEADYYC | QVWDSSSDH--- | VVFGGGTKLTVI | (Seq. ID No. 169) |
| HBL2d | 3C4 | GIPERLSGSNSGNTATLTISRVEAGDEADYYC | QVWDSSSDP--- | VVFGGGTKLAVL | (Seq. ID No. 170) |
| HBL3 | 3B10 | AIPERFSGSNSGNTATLTISRAEAGDEADYYC | QVWDDSSDH--- | VVFGGGTKLFVL | (Seq. ID No. 171) |
| HBL4a | 3C11 | GIPERLSGSNSGNTATLTITRVEAGDEADYYC | QVWDSSGDHP-- | VVFGGGTKLTVL | (Seq. ID No. 172) |
| | 3D6 | GIAERFSGSNSGNTATLTISRAEAGDEAEYYC | QVWDSSGDH--- | VVFGGGTKLTVL | (Seq. ID No. 173) |
| HBL4b | 3E5 | GIPERFSGSNSGNTATLTISRVEAGDEADYYC | QVWDSSSDHL-- | VVFGGGTLLTVL | (Seq. ID No. 174) |
| HBL4c | 3E8 | GTPERFSGSNSGNTATLTISRVEAGDEADYFC | QVWDSTSDHPY- | VVFGGGTKLTVL | (Seq. ID No. 175) |
| HBL4d | 3E12 | GIPERFSGSNSGTTATLTITSRVEAGDEADYYC | QVWDSTGDR--- | VVFGGGTKLTVL | (Seq. ID No. 176) |
| HBL5 | 3D1 | GIPERFSGSNSGNAATLTITRVEAGDEADYYC | QVWGDTGDHP-- | VVFGGGTKLTVL | (Seq. ID No. 177) |
| HBL7 | 3G5 | GIPERFSGSNSGNAATLTITRVEAGDEADYYC | QVWGDTGDHP-- | VVFGGGTKLTVL | (Seq. ID No. 178) |

HBL2d 3C4 had a "tga" stop codon in CDR1 as indicated by "J".

Mouse IgG kappa clones to IgE Fc — Heavy chain

| Fab | Framework 1 | CDR1 | Framework 2 | CDR2 | | |
|---|---|---|---|---|---|---|
| | QSGAELMKPGASVKISCKATDYTFS | NYWIE | WVKQRPGHGLEWIG | EILPGSGSTNFNEKFKG | | |
| m2G1R2A8 | ·····················RT· | ······ | ·R············· | ····T·D········R· | | |
| m2G1R2B9 | ········I··············· | ······ | ··············· | ······D······R··D | | |
| m2G1R2B11, C5 | ························ | ······ | ·I············· | ······D········· | | |
| m2G1R2C2, F9, c3 | ·····V·················· | ······ | ··············· | ······D··V······ | | |
| m2G1R2C8 | ························ | ······ | ··············· | ······D··V······ | | |
| m2G1R2F12 | ························ | ······ | ··············· | ······D········· | | |
| m2G1R2G1, C11 | ·········S·············· | ······ | ··············· | ····T·D········R· | | |
| m2G1R2H8 | ························ | ······ | ··············· | ······D········· | | |
| m2G1R2F7 | ························ | ······ | ··············· | D·····D··V······ | | |
| m2G1R2D10 | ························ | ······ | ··············· | ······D········· | | |
| m2G1R2F10 | ·········S·············· | ······ | ··············· | ······D········· | | |
| m2G1R2H3 | ························ | ······ | ··············· | ······DA········ | | |
| m2G1R2H7 | ·····V·················· | ······ | ··············· | ······D··VS····· | | |
| m2G1R2a9 | ························ | ······ | ··············· | ······D········· | | |

| Fab | Framework 3 | CDR3 | FR4 | |
|---|---|---|---|---|
| | KATFTADTSSNTAYMQLSSLTSEDSAVYYCAR | AYFTFS | LDYWGQGTTLTVSS | |
| m2G1R2A8 | ································ | ······ | ·············· | (Seq. ID No. 233) |
| m2G1R2B9 | ································ | ·····Y | F············· | (Seq. ID No. 234) |
| m2G1R2B11, C5 | ································ | ·····Y | F············· | (Seq. ID No. 235) |
| m2G1R2C2, F9, c3 | ··············Y················ | ·····Y | F············· | (Seq. ID No. 236) |
| m2G1R2C8 | ·············L·Y················ | ·····Y | F············· | (Seq. ID No. 237) |
| m2G1R2F12 | ································ | ·····Y | F············· | (Seq. ID No. 238) |
| m2G1R2G1, C11 | ································ | ·····Y | F············· | (Seq. ID No. 239) |
| m2G1R2H8 | ································ | ·····Y | F············· | (Seq. ID No. 240) |
| m2G1R2F7 | ··············Y················ | ···Y·L· | F············· | (Seq. ID No. 241) |
| m2G1R2D10 | ··············Y················ | ·····Y | F············· | (Seq. ID No. 242) |
| m2G1R2F10 | ··············S················ | ·····Y | ·············· | (Seq. ID No. 243) |
| m2G1R2H3 | ··············Y················ | ·····Y | F············· | (Seq. ID No. 244) |
| m2G1R2H3 | ································ | ·····Y | F············· | (Seq. ID No. 245) |
| m2G1R2a9 | ································ | ···Y·L· | F············· | (Seq. ID No. 246) |

Mouse IgG lambda clones to IgE Fc

Fig. 9b

| Fab | Framework 3 | CDR3 | FR4 | (Seq. ID No.) |
|---|---|---|---|---|
| m3G1R3A11 | KATFTADTSSNTAYMQLSSLTSEDSAVYYCAR | QVGLRWF | FDYWGQGTTLTVSS | 247 |
| m3G1R3A12 | ································ | ······· | ·············· | 248 |
| m3G1R3D12 | ································ | ······· | ·············· | 249 |
| m3G1R3G8 | ································ | ······· | ·············· | 250 |
| m3G1R3E9 | ································ | ······· | ·············· | 251 |
| m3G1R3B10 | KATFTADTSSNIAYMQLSSLTSEDSAVYYCAR | QVGLRWY | FDYWGQGTTLTVSS | 252 |
| m3G1R3B11 | ······I························ | ·····Y· | ·············· | 253 |
| m3G1R3F11 | ······I························ | ·····Y· | ·············· | 254 |
| m3G1R3H9 | ······I························ | ·····Y· | ·············· | 255 |
| m3G1R3E7 | RFTISRDDSQSILYLQMNTLRAEDSATYYCLR | NGRPYYYALDYWGQGTSVSVSS | | 256 |
| m3G1R3E10 | ························S······· | ······················ | | 257 |
| m3G1R3F8 | ························S······· | ······················ | | 258 |
| m3G1R3G9 | ························L······· | ······················ | | 259 |
| m3G1R3B7 | KATFTADTSSNTAYMQLSSLTSEDSAVYYCAR | GLWLRGYYFDYWGQGTTLTVSS | | 260 |
| m3G1R3C7 | ································ | GLW··GYY·············· | | 261 |
| m3G1R3G12 | ································ | GLW··GYY·············· | | 262 |
| m3G2aR3C8 | ································ | GLW··GYY·············· | | 263 |
| m3G2aR3H7 | ································ | GLW··GYY·············· | | 264 |
| m3G2aR3B10 | RFTISRDDSQSILYLQMNTLRAEDSATYYCAR | HGRPYYYLMDYWGQGTSVTVSS | | 265 |
| m3G2aR3E10 | ································ | ······················ | | 266 |
| m3G2aR3D8 | KVTFTADTSSNTAYMQFSSLTSEDSAVYYCAT | TTVVRDYLDYWGQGTTLTVSS | | 267 |
| m3G2aR3D4 | ································ | ····················· | | 268 |
| m3G2aR3B4 | ···S········L··················· | ····················· | | 269 |

Fig. 9c

Kappa light chain

| Fab | Framework 1 | CDR1 | Framework 2 | CDR2 |
|---|---|---|---|---|
| m3G1R3B10 | SRQIVLTQSPAIMSASPGEKVTMTC | SASSSVSYMH | WYQQKSSTSPKLWIY | DTSKLAS |
| m3G1R3H9 | ·························· | ·········· | ··············· | ······· |
| m3G1R3B7 | SRQIVLTQSPAIMSASPGEKVTMTC | SASSSVNYMH | WYQQKSGTSPKRWIY | DTSKLTS |
| m3G1R3C7 | ·························· | ··N···S··· | ··········A··· | ······A· |
| m3G1R3D12 | SRQIVLTQSPAIMSASPGEKVTMTC | SASSSVSYMH | WYQQKSSTSPKLWIY | DTSKLAS |
| m3G1R3E9 | ·························· | ·········· | ··············· | ······· |
| m3G1R3E7 | SRDIQMTQSPASLSASVGETVTITC | RASENINSYLA | WFQQKQGKSPQLLVY | DAKTLAE |
| m3G2aR3D8 | ·························· | ··········· | ··············· | ······· |
| m3G2aR3E10 | ·························· | ··········· | ··············· | ······· |

| Fab | Framework 3 | CDR3 | FR4 | |
|---|---|---|---|---|
| m3G1R3B10 | GVPGRFSGSGSGNSYSLTISSMEAEDVATYYC | FQGSGYP LT | FGAGTKLELKR | (Seq. ID No. 270) |
| m3G1R3H9 | ······························ | ·········· | ··S····I··· | (Seq. ID No. 271) |
| m3G1R3B7 | GVPARFSGSGSGTSYSLTISSMEAEDAATYYC | QQWNRNP PT | FGGGTKLEIKR | (Seq. ID No. 272) |
| m3G1R3C7 | ······························ | ·········· | ··········· | (Seq. ID No. 273) |
| m3G1R3D12 | GVPGRFSGSGSGNSYSLTISSMEAEDVATYYC | FQGSGYP LT | FGSGTKLEIKR | (Seq. ID No. 274) |
| m3G1R3E9 | ···············T············· | ·········· | ··········· | (Seq. ID No. 275) |
| m3G1R3E7 | GVPSRFSGSGSGTQFSLKINSLQPEDFGSYYC | QHHYGIP LT | FGAGTKLELKR | (Seq. ID No. 276) |
| m3G2aR3D8 | ······························ | ·········· | ··········· | (Seq. ID No. 277) |
| m3G2aR3E10 | ······························ | ·········· | ··········· | (Seq. ID No. 278) |

Fig. 9d

ENGINEERED TEMPLATES AND THEIR USE IN SINGLE PRIMER AMPLIFICATION

RELATED APPLICATIONS

This application is a continuation in part of U.S. application Ser. No. 10/251,085 filed Sep. 19, 2002 which claims priority to U.S. Provisional Application No. 60/323,455 filed Sep. 19, 2001.

TECHNICAL FIELD

This disclosure relates to engineered templates useful for amplification of a target nucleic acid sequence. More specifically, templates which are engineered to contain complementary sequences at opposite ends thereof are provided by a nested oligonucleotide extension reaction (NOER). The engineered template allows Single Primer Amplification (SPA) to amplify a target sequence within the engineered template. In particularly useful embodiments, the target sequences from the engineered templates are cloned into expression vehicles to provide a library of polypeptides or proteins, such as, for example, an antibody library.

BACKGROUND OF RELATED ART

Methods for nucleic acid amplification and detection of amplification products assist in the detection, identification, quantification and sequence analysis of nucleic acid sequences. Nucleic acid amplification is an important step in the construction of libraries from related genes such as, for example antibodies. These libraries can be screened for antibodies having specific, desirable activities. Nucleic acid analysis is important for detection and identification of pathogens, detection of gene alteration leading to defined phenotypes, diagnosis of genetic diseases or the susceptibility to a disease, assessment of gene expression in development, disease and in response to defined stimuli, as well as the various genome projects. Other applications of nucleic acid amplification method include the detection of rare cells, detection of pathogens, and the detection of altered gene expression in malignancy, and the like. Nucleic acid amplification is also useful for qualitative analysis (such as, for example, the detection of the presence of defined nucleic acid sequences) and quantification of defined gene sequences (useful, for example, in assessment of the amount of pathogenic sequences as well as the determination of gene multiplication or deletion, and cell transformation from normal to malignant cell type, etc.). The detection of sequence alterations in a nucleic acid sequence is important for the detection of mutant genotypes, as relevant for genetic analysis, the detection of mutations leading to drug resistance, pharmacogenomics, etc.

There are many variations of nucleic acid amplification, for example, exponential amplification, linked linear amplification, ligation-based amplification, and transcription-based amplification. One example of exponential nucleic acid amplification method is polymerase chain reaction (PCR) which has been disclosed in numerous publications. See, for example, Mullis et al. Cold Spring Harbor Symp. Quant. Biol. 51:263-273 (1986); Mullis K. EP 201,184; Mullis et al. U.S. Pat. No. 4,582,788; Erlich et al. EP 50,424, EP 84,796, EP 258,017, EP 237,362; and Saiki R. et al. U.S. Pat. No. 4,683,194. In fact, the polymerase chain reaction (PCR) is the most commonly used target amplification method. PCR is based on multiple cycles of denaturation, hybridization of two different oligonucleotide primers, each to opposite strand of the target strands, and primer extension by a nucleotide polymerase to produce multiple double stranded copies of the target sequence.

Amplification methods that employ a single primer, have also been disclosed. See, for example, U.S. Pat. Nos. 5,508,178; 5,595,891; 5,683,879; 5,130,238; and 5,679,512. The primer can be a DNA/RNA chimeric primer, as disclosed in U.S. Pat. No. 5,744,308.

Some amplification methods use template switching oligonucleotides (TSOs) and blocking oligonucleotides. For example, a template switch amplification in which chimeric DNA primer are utilized is disclosed in U.S. Pat. Nos. 5,679,512; 5,962,272; 6,251,639 and by Patel et al. Proc. Natl. Acad. Sci. U.S.A. 93:2969-2974 (1996).

However the previously described target amplification methods have several drawbacks. For example, the transcription base amplification methods, such as Nucleic Acid Sequence Based Amplification (NASBA) and transcription mediated amplification (TMA), are limited by the need for incorporation of the polymerase promoter sequence into the amplification product by a primer, a process prone to result in non-specific amplification. Another example of a drawback of the current amplification methods is the requirement of two binding events which may have optimal binding at different temperatures as well as the use of primers containing naturally occurring sequences. This combination of factors results in increased likelihood of mis-priming and resultant amplification of sequences other than the target sequence.

Therefore, there is a need for improved nucleic acid amplification methods that overcome these drawbacks. The invention provided herein fulfills this need and provides additional benefits.

SUMMARY

Novel methods of amplifying nucleic acid have now been discovered which include the steps of: a) annealing a primer to a template nucleic acid sequence, the primer having a first portion which anneals to the template and a second portion of predetermined sequence; b) synthesizing a polynucleotide that anneals to and is complementary to the portion of the template between the location at which the first portion of the primer anneals to the template and the end of the template, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide and a second portion having the same predetermined sequence as the second portion of the primer; e) extending the polynucleotide synthesized in step (b) to provide a terminal portion thereof that is complementary to the predetermined sequence; and f) amplifying the extended polynucleotide using a single primer having the predetermined sequence.

In an alternative embodiment, the method includes the steps of a) annealing a primer and a boundary oligonucleotide to a template nucleic acid sequence, the primer having a first portion which anneals to the template and a second portion of predetermined sequence; b) synthesizing a polynucleotide that anneals to and is complementary to the portion of the template between the location at which the first portion of the primer anneals to the template and the portion of the template to which the boundary oligonucleotide anneals, the polynucleotide having a first end and a second end, wherein the first end incorporates the primer; c) separating the polynucleotide synthesized in step (b) from the template; d) annealing a nested oligonucleotide to the second end of the polynucleotide synthesized in step (b), the nested oligonucleotide having a first portion that anneals to the second end of the polynucleotide and a second portion having the same predetermined sequence as the second portion of the primer; e) extending the polynucleotide synthesized in step (b) to provide a terminal portion thereof that is complementary to the predetermined sequence; and f) amplifying the extended polynucleotide using a single primer having the predetermined sequence.

It is also contemplated that a engineered nucleic acid strand having a predetermined sequence at a first end thereof and a sequence complementary to the predetermined sequence at the other end thereof is itself a novel aspect of this disclosure.

In another aspect, this disclosure provides a new method of amplifying a nucleic acid strand that includes the steps of providing an engineered nucleic acid strand having a predetermined sequence at a first end thereof and a sequence complementary to the predetermined sequence at the other end thereof; and contacting the engineered nucleic acid strand with a primer having the predetermined sequence in the presence of a polymerase and nucleotides under conditions suitable for polymerization of the nucleotides.

The amplification processes and engineered templates described herein can be used to prepare amplified products that can be ligated into a suitable expression vector. The vector may then be used to transform an appropriate host organism using standard methods to produce the polypeptide or protein encoded by the target sequence. In particularly useful embodiments, the techniques described herein are used to amplify a family of related sequences to build a complex library, such as, for example an antibody library.

BRIEF DESCRIPTION OF DRAWINGS

FIG. 3 is a schematic illustration of an alternate embodiment wherein multiple rounds of polymerization are performed and a restriction oligonucleotide is annealed to the newly synthesized strands, rather than to the original template;

Figure 8C:
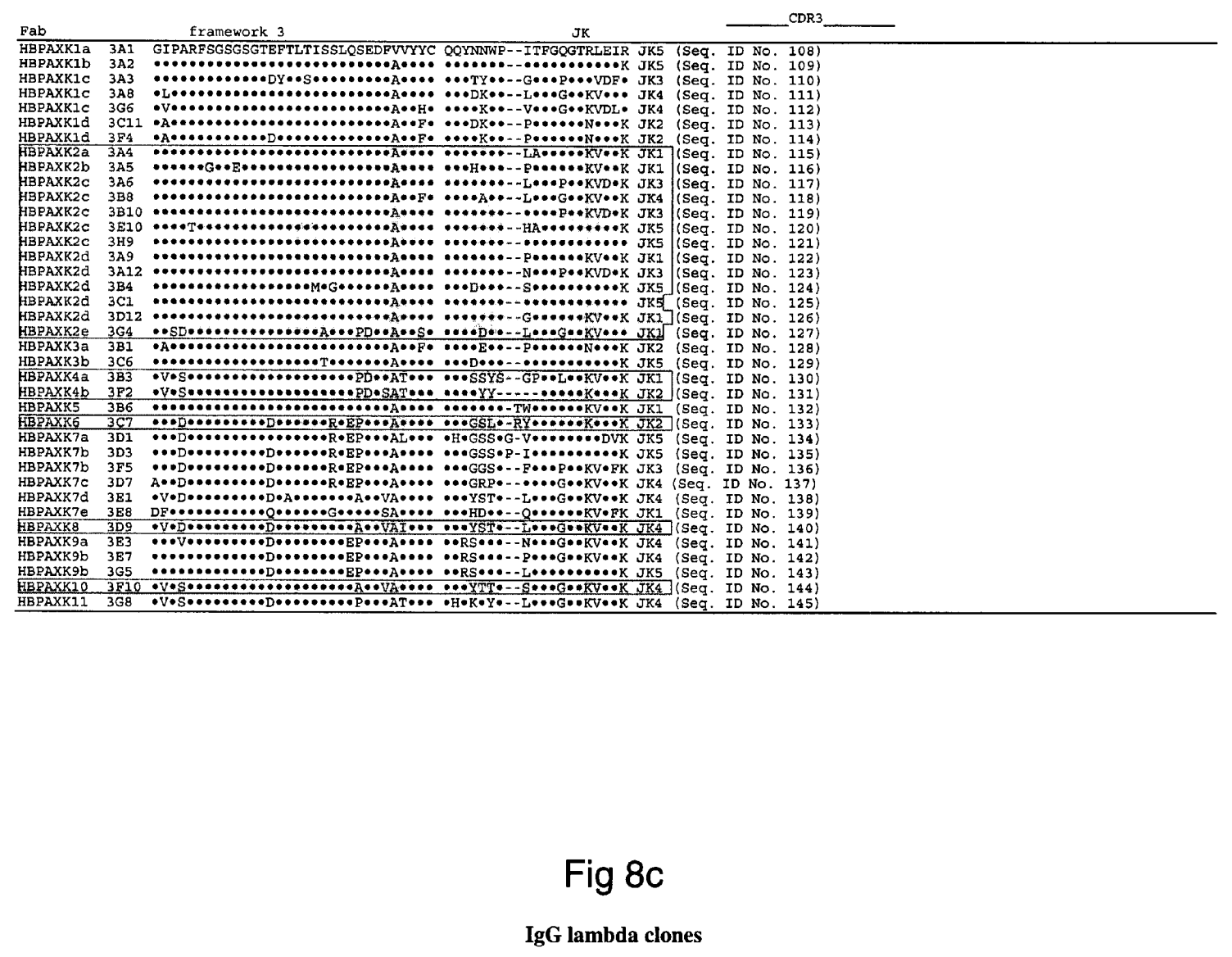

FIGS. 8a-e show the sequences of isolated Fabs produced in Example 3; and

Figure 9B:
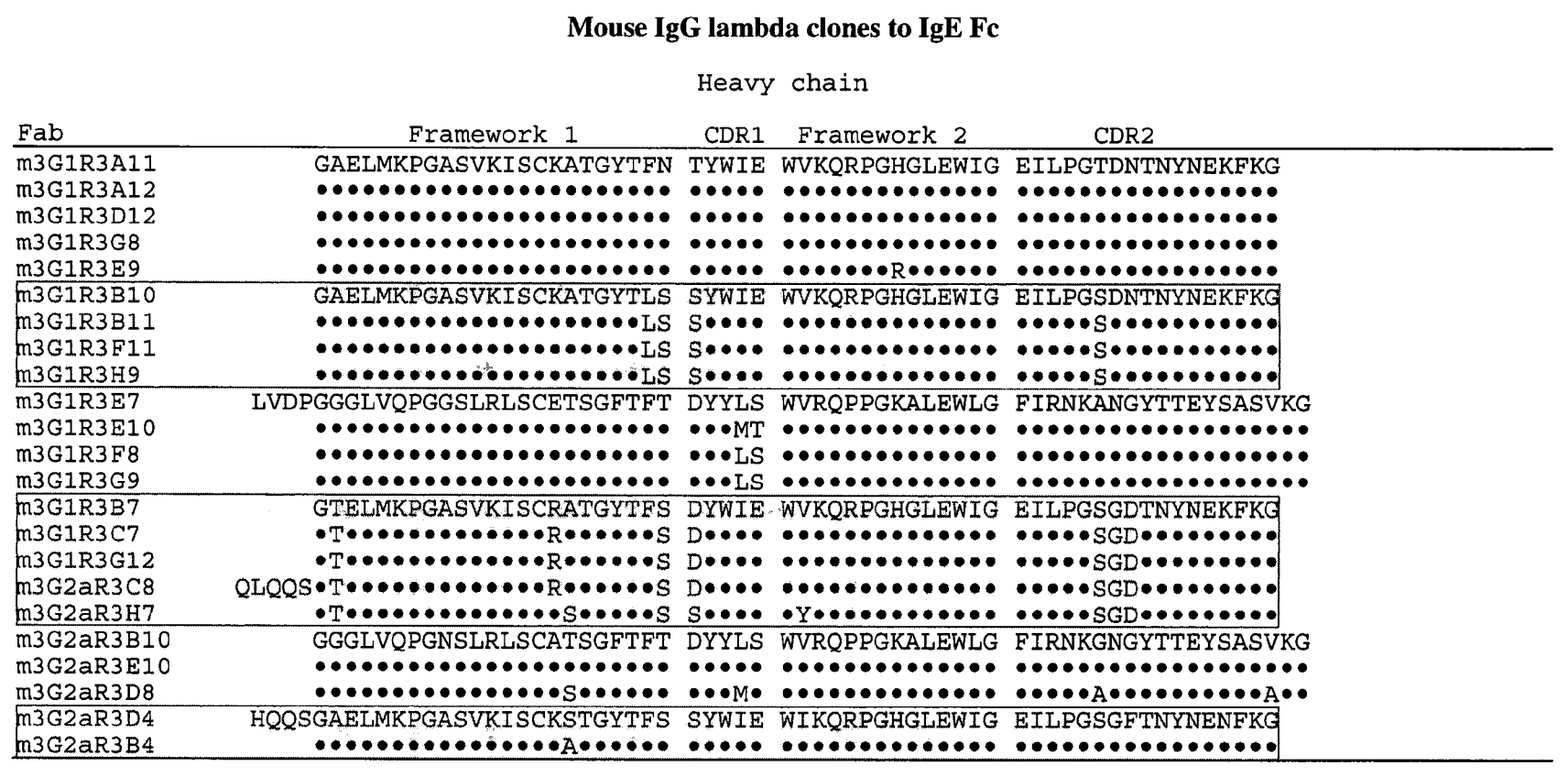

FIGS. 9a-d show the sequences of isolated Fabs produced in Example 5.

DETAILED DESCRIPTION OF PREFERRED EMBODIMENTS

Figure 1:
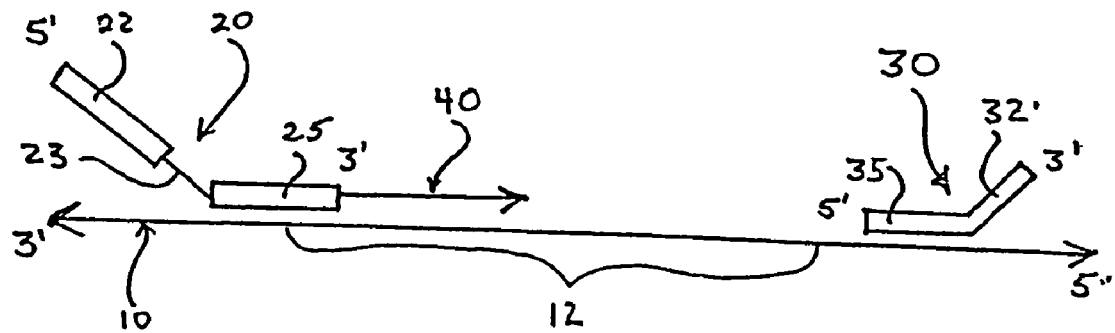
FIG. 1 is a schematic illustration of a primer and boundary oligo annealed to a template.

The present disclosure provides a method of amplifying a target nucleic acid sequence. In particularly useful embodiments, the target nucleic acid sequence is a gene encoding a polypeptide or protein. The disclosure also describes how the products of the amplification may be cloned and expressed in suitable expression systems. In particularly useful embodiments, the techniques described herein are used to amplify a family of related sequences to build a complex library, such as, for example an antibody library.

The target nucleic acid sequence is exponentially amplified through a process that involves only a single primer. The ability to employ a single primer (i.e., without the need for both forward and reverse primers each having different sequences) is achieved by engineering a strand of nucleic acid that contains the target sequence to be amplified. The engineered strand of nucleic acid (sometimes referred to herein as the "engineered template") is prepared from two templates; namely, 1) a starting material that is a natural or synthetic nucleic acid (e.g., DNA or cDNA) containing the sequence to be amplified and 2) a nested oligonucleotide. The starting material can be considered the original template. The nested oligonucleotide is used as a template to extend the nucleotide sequence of the original template during creation of the engineered strand of nucleic acid. The engineered strand of nucleic acid is created from the original template by a series of manipulations that result in the presence of complementary sequences at opposite ends thereof. It is these complementary sequences that allow amplification using only a single primer.

Any nucleic acid, in purified or nonpurified form, can be utilized as the starting material for the processes described herein provided it contains or is suspected of containing the target nucleic acid sequence to be amplified. Thus, the starting material employed in the process may be, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be utilized. The target nucleic acid sequence to be amplified may be a fraction of a larger molecule or can be present initially as a discrete molecule. The starting nucleic acid may contain more than one desired target nucleic acid sequence which may be the same or different. Therefore, the present process may be useful not only for producing large amounts of one target nucleic acid sequence, but also for amplifying simultaneously more than one different target nucleic acid sequence located on the same or different nucleic acid molecules.

The nucleic acids may be obtained from any source, for example: genomic or cDNA libraries, plasmids, cloned DNA or RNA, or from natural DNA or RNA from any source, including bacteria, yeast, viruses, and higher organisms such as plants or animals. The nucleic acids can be naturally occurring or may be synthetic, either totally or in part. Techniques for obtaining and producing the nucleic acids used in the present invention are well known to those skilled in the art. If the nucleic acid contains two strands, it is necessary to separate the strands of the nucleic acid before it can be used as the original template, either as a separate step or simultaneously with the synthesis of the primer extension products. Additionally, if the starting material is first strand DNA, second strand DNA may advantageously be created by processes within the purview of those skilled in the art and used as the original template from which the engineered template is created.

First strand cDNA is a particularly useful original template for the present methods. Suitable methods for generating DNA templates are known to and readily selected by those skilled in the art. In a preferred embodiment, $1^{st}$ strand cDNA is synthesized in a reaction where reverse transcriptase catalyzes the synthesis of DNA complementary to any RNA starting material in the presence of an oligodeoxynucleotide primer and the four deoxynucleoside triphosphates, dATP, dGTP, dCTP, and TTP. The reaction is initiated by annealing of the oligo-deoxynucleotide primer to the 3' end of mRNA followed by stepwise addition of the appropriate deoxynucleotides as determined by base pairing relationships with the mRNA nucleotide sequence, to the 3' end of the growing chain. As those skilled in the art will appreciate, all mRNA in a sample can be used to generate first strand cDNA through the annealing of oligo dT to the polyA tail of the mRNA.

Once the original template is obtained, a primer 20 and a boundary oligonucleotide 30 are annealed to the original template 10. (See FIG. 1.) A strand of nucleic acid complementary to the portion of the original template beginning at the 3' end of the primer up to about the 5' end of the boundary oligonucleotide is polymerized.

The primer 20 that is annealed to the original template includes a first portion 22 of predetermined sequence that preferably does not anneal to the original template and a second portion 25 that anneals to the original template, and optionally includes a restriction site 23 between the first and second portions. The primer anneals to the original template adjacent to the target sequence 12 to be amplified. It is contemplated that the primer can anneal to the original template upstream of the target sequence to be amplified, or that the primer may overlap the beginning of the target sequence 12 to be amplified as shown in FIG. 1. The predetermined sequence of the non-annealing portion 22 of the primer is not native in the original template and is selected so as to provide a sequence to which the single primer used during the amplification process can hybridize as described in detail below. Optionally, the predetermined sequence may include a restriction site useful for insertion of a portion of the engineered template into an expression vector as described more fully hereinbelow.

The boundary oligonucleotide 30 that is annealed to the original template serves to terminate polymerization of the nucleic acid. Any oligonucleotide capable of terminating nucleic acid polymerization may be utilized as the boundary oligonucleotide 30. In a preferred embodiment the boundary oligonucleotide includes a first portion 35 that anneals to the original template 10 and a second portion 32 that is not susceptible to an extension reaction. Techniques to prevent the boundary oligo from acting as a site for extension are within the purview of one skilled in the art. By way of example, portion 32 of the boundary oligo 30 may be designed so that it does not anneal to the original template 10 as shown in FIG. 1. In such embodiments, the boundary oligonucleotide 30 prevents further polymerization but does not serve as a primer for nucleic acid synthesis because the 3' end thereof does not hybridize with the original template 10. Alternatively, the 3' end of the boundary oligo 30 might be designed to include locked nucleic acid to achieve the same effect. Locked nucleic acid is disclosed for example in WO 99/14226, the contents of which are incorporated herein by reference. Those skilled in the art will envision other ways of ensuring that no extension of the 3' end of the boundary oligo occurs.

Primers and oligonucleotides described herein may be synthesized using established methods for oligonucleotide synthesis which are well known in the art. Oligonucleotides, including primers of the present invention include linear oligomers of natural or modified monomers or linkages, such as deoxyribonucleotides, ribonucleotides, and the like, which are capable of specifically binding to a target polynucleotide by way of a regular pattern of monomer-to monomer interactions such as Watson-Crick base pairing. Usually monomers are linked by phosphodiester bonds or their analogs to form oligonucleotides ranging in size from a few monomeric units e.g., 3-4, to several tens of monomeric units. A primer is typically single-stranded, but may be double-stranded. Primers are typically deoxyribonucleic acids, but a wide variety of synthetic and naturally occurring primers known in the art may be useful for the methods of the present disclosure. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., chromogenic, radioactive, or fluorescent moieties and used as detectable moieties.

Polymerization of nucleic acid can be achieved using methods known to those skilled in the art. Polymerization is generally achieved enzymatically, using a DNA polymerase which sequentially adds free nucleotides according to the instructions of the template. Several different DNA polymerases are suitable for use in the present process. In a certain embodiments, the criteria for selection includes lack of exonuclease activity or DNA polymerases which do not possess a strong exonuclease. DNA polymerases with low exonuclease activity for use in the present process may be isolated from natural sources or produced through recombinant DNA techniques. Illustrative examples of polymerases that may be used, are, without limitation, T7 Sequenase v. 2.0, the Klenow Fragment of DNA polymerase I lacking exonuclease activity, the Klenow Fragment of Taq Polymerase, exo.- Pfu DNA polymerase, Vent. (exo.-) DNA polymerase, and Deep Vent. (exo-) DNA polymerase.

Figure 2A:
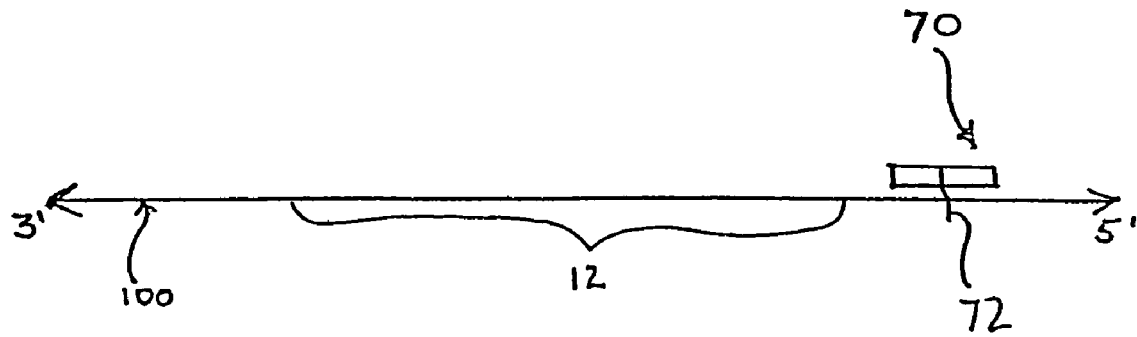
FIG. 2A is a schematic illustration of a restriction oligo annealed to a nucleic acid strand.
Figure 2B:
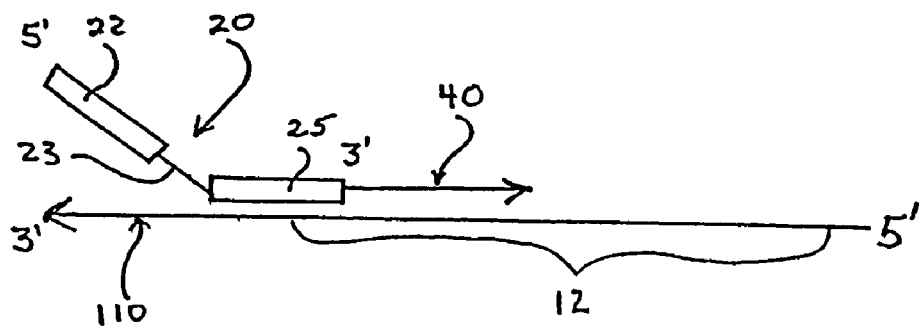
FIG. 2B is a schematic illustration of a primer annealed to a template that has a shortened 5' end.

In a particularly useful embodiment, the use of a boundary oligonucleotide is avoided by removing unneeded portions of the starting material by digestion. In this embodiment, which is shown schematically in FIG. 2A, a restriction oligonucleotide 70 is annealed to the starting material 100 at a preselected location. The restriction oligonucleotide provides a double stranded portion on the starting material containing a restriction site 72. Suitable restriction sites, include, but are not limited to Xho I, Spe I, Nhe1, Hind III, Nco I, Xma I, Bgl II, Bst I, and Pvu I. Upon exposure to a suitable restriction enzyme, the starting material is digested and thereby shortened to remove unnecessary sequence while preserving the desired target sequence 12 (or portion thereof) to be amplified on what will be used as the original template 110. Once the original template 110 is obtained, a primer 20 is annealed to the original template 110 (see FIG. 2B) adjacent to or overlapping with the target sequence 12 as described above in connection with previous embodiments. A strand of nucleic acid 40 complementary to the portion of the original template between the 3' end of the primer 20 and the 5' end of the original template 110 is polymerized. As those skilled in the art will appreciate, in this embodiment where a restriction oligonucleotide is employed to generate the original template, there is no need to use a boundary oligonucleotide, because primer extension can be allowed to proceed all the way to the 5' end of the shortened original template 110.

Once polymerization is complete (i.e., growing strand 40 reaches the boundary oligonucleotide 30 or the 5' end of the shortened original template 110), the newly synthesized complementary strand is separated from the original template by any suitable denaturing method including physical, chemical or enzymatic means. Strand separation may also be induced by an enzyme from the class of enzymes known as helicases or the enzyme RecA, which has helicase activity and in the presence of riboATP is known to denature DNA.

The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63-67, and techniques for using RecA are reviewed in C. Radding, Ann. Rev. Genetics, 16:405-37 (1982).

The newly synthesized complementary strand thus includes sequences provided by the primer 20 (e.g., the predetermined sequence 22, the optional restriction site 23 and the annealing portion 25 of the primer) as well as the newly synthesized portion 45 that is complementary to the portion of the original template 10 between the location at which the primer 20 was annealed to the original template 10 and either the portion of the original template 10 to which the boundary oligonucleotide 30 was annealed or the shortened 5' end of the original template. See FIG. 4.

Optionally, multiple rounds of polymerization (preferably, 15-25 rounds) using the original template and a primer are performed to produce multiple copies of the newly synthesized complementary strand for use in subsequent steps. Making multiple copies of the newly synthesized complementary strand at this point in the process (instead of waiting until the entire engineered template is produced before amplifying) helps ensure that accurate copies of the target sequence are incorporated into the engineered templates ultimately produced. It is believed that multiple rounds of polymerization based on the original template provides a greater likelihood that a better representation of all members of the library will be achieved, therefore providing greater diversity compared to a single round of polymerization.

In an alternative embodiment, newly synthesized strands are produced by annealing primer 20 as described above to original template 10 and performing multiple rounds of polymerization, without either the presence of a blocking oligonucleotide or removing a portion of the original template. In this embodiment, which is shown schematically in FIG. 3, the primer is extended along the full length of the original template to provide a full length newly synthesized strand 140. Next, a restriction oligonucleotide 170 is hybridized to the full length newly synthesized strand. The restriction oligonucleotide provides a double stranded portion on the newly synthesized strand containing a restriction site. Suitable restriction sites, include, but are not limited to Xho I, Spe I, Nhe1, Hind III, Nco I, Xma I, Bgl II, Bst I, Pvu I, Xcm I, BsaJ I, Hpa I, ApaL I, Sac I, Dra III and Sma I. Upon exposure to a suitable restriction enzyme, the newly synthesized strand is digested and thereby shortened. A nested oligonucleotide 50 can then be hybridized to the shortened newly synthesized strand 142 to complete preparation of the engineered template, as described in more detail below.

Figure 4:
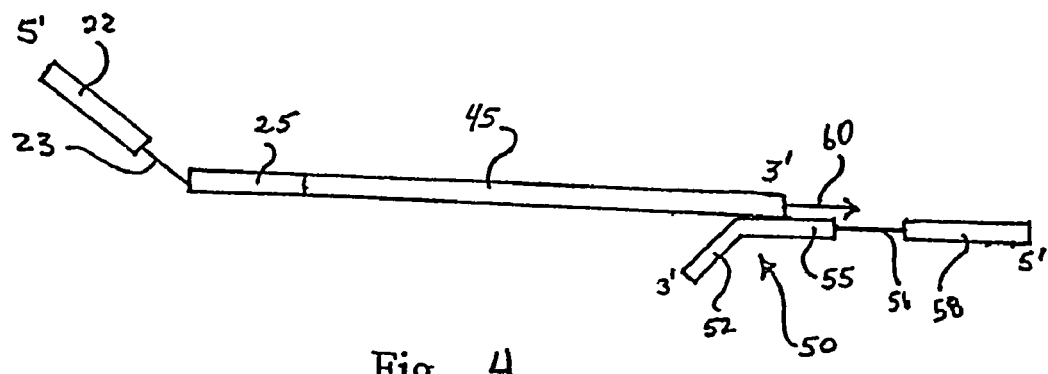
FIG. 4 is a schematic illustration of a nested oligo annealed to a newly synthesized nucleic acid strand.

The next step in preparing the engineered template involves annealing a nested oligonucleotide 50 to the 3' end of the newly synthesized complementary strand, for example as shown in FIG. 4. As seen in FIG. 4, the nested oligonucleotide 50 provides a template for further polymerization necessary to complete the engineered template. Nested oligonucleotide 50 includes a portion 52 that does not hybridize and/or includes modified bases to the newly synthesized complementary strand, thereby preventing the nested oligonucleotide from serving as a primer. Nested oligonucleotide 50 also includes a portion 55 that hybridizes to the 3' end of the newly synthesized complementary strand. Portion 55 may be coterminous with newly synthesized portion 45 or may extend beyond newly synthesized portion 45 as shown in FIG. 4. Nested oligonucleotide 50 may optionally also include a portion 56 defining a restriction site. The final portion 58 of nested oligonucleotide 50 contains the same predetermined sequence as portion 22 of primer 20. From the point at which portion 55 extends beyond the 3' end of the beginning the newly synthesized complementary strand, the nested oligonucleotide serves as a template for further polymerization to form the engineered template. It should be understood that the nested oligo may contain part of the target sequence (if part thereof was truncated in forming the original template) or may include genes that encode a polypeptide or protein (or portion thereof) such as, for example, one or more CDR's or Framework regions or constant regions of an antibody. It is also contemplated that a collection of nested oligonucleotides having different sequences can be employed, thereby providing a variety of templates which results in a library of diverse products. Thus, polymerization will extend the newly synthesized complementary strand by adding additional nucleic acid 60 that is complementary to the nested oligonucleotide as shown in FIG. 4. Techniques for achieving polymerization are within the purview of one skilled in the art. As previously noted, selecting a suitable polymerase, an enzyme lacking exonuclease activity may be preferred in certain embodiments.

Figure 5:
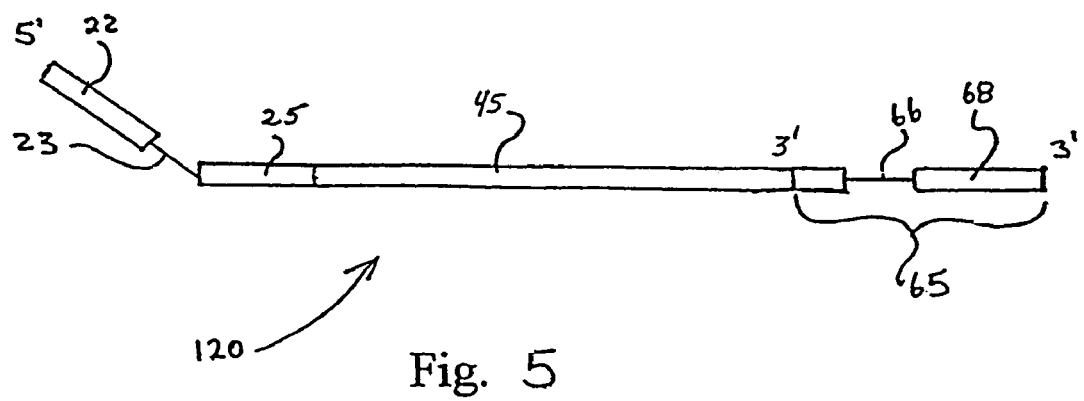
FIG. 5 is a schematic illustration of an engineered template in accordance with this disclosure.

Once polymerization is complete, the engineered template 120 is separated from the nested oligonucleotide 50 by techniques well known to those skilled in the art such as, for example, heat denaturation. The resulting engineered template 120 contains a portion derived from the original primer 20, portion 45 that is complementary to a portion of the original template, and portion 65 that is complementary to a portion of the nested oligonucleotide (see FIG. 5). Significantly, the 3' end of engineered template 120 includes portion 68 containing a sequence that is complementary to the predetermined sequence of portion 22 of primer 20. This allows for amplification of the desired sequence contained within engineered template 120 using a single primer having the same sequence as the predetermined sequence of primer portion 22 using techniques known to those of ordinary skill in the art. During single primer amplification, the presence of a polymerase having exonuclease activity is preferred because such enzymes are known to provide a "proofreading" function and have relatively higher processivity compared to polymerases lacking exonuclease activity.

Figure 6:
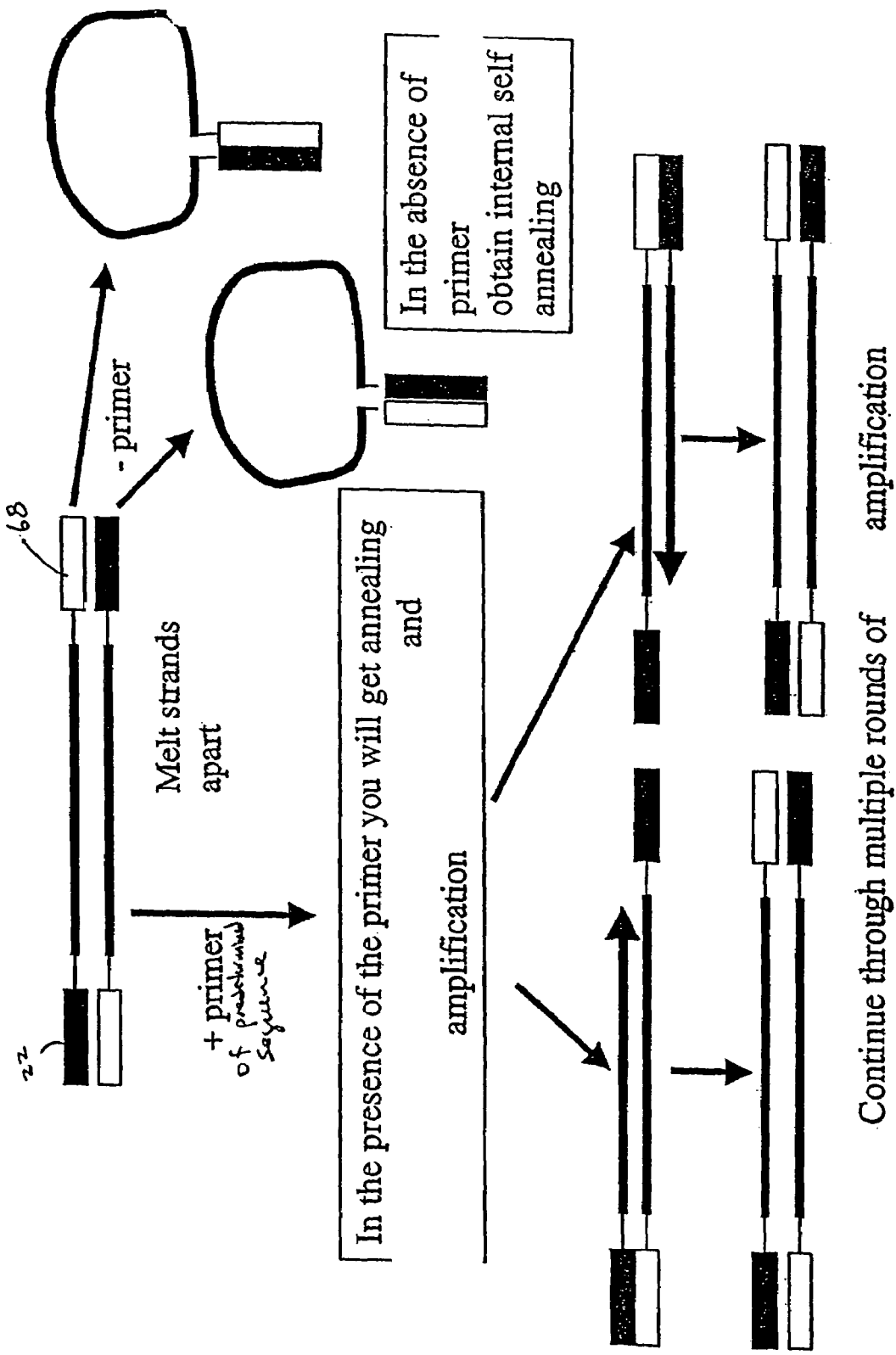
FIG. 6 is a schematic illustration of the single primer amplification of an engineered template.

FIG. 6 illustrates the steps involved in the single primer amplification of the newly synthesized cDNA template. When the primer is present in the reaction mixture it hybridizes to the sequences flanking the template and amplifies the template. When there is no primer present, it is believed that there is internal self annealing between the 5' end predetermined sequence and the 3' end sequence which is complementary to the predetermined sequence. In a preferred embodiment, the predetermined sequence and complementary predetermined sequence may be designed to anneal at higher temperatures in order to avoid miss-priming during the single primer amplification reaction.

After amplification is performed, the products may be detected using any of the techniques known to those skilled in the art. Examples of methods used to detect nucleic acids include, without limitation, hybridization with allele specific oligonucleotides, restriction endonuclease cleavage, single-stranded conformational polymorphism (SSCP), analysis.gel electrophoresis, ethidium bromide staining, fluorescence resonance energy transfer, hairpin FRET essay, and TaqMan assay.

Once the engineered nucleic acid is amplified a desired number of times, restriction sites 23 and 66 or any internal restriction sites can be used to digest the strand so that the target nucleic acid sequence can be ligated into a suitable expression vector. The vector may then be used to transform an appropriate host organism using standard methods to produce the polypeptide or protein encoded by the target sequence.

In particularly useful embodiments, the methods described herein are used to amplify target sequences encoding antibodies or portions thereof, such as, for example the variable regions (either light or heavy chain) using cDNA of an antibody. In this manner, a library of antibodies can be amplified and screened. Thus, for example, starting with antibody mRNA, first strand cDNA can be produced and digested to provide an original template. A primer can be designed to anneal upstream to a selected complementary determining region (CDR) so that the newly synthesized nucleic acid strand includes the CDR. By way of example, if the target sequence is heavy chain CDR3, the primer may be designed to anneal to the heavy chain framework one (FR1) region. Those skilled in the art will readily envision how to design appropriate primers to anneal to other upstream sites or to reproduce other selected targets within the antibody cDNA based on this disclosure.

The following Examples are provided to illustrate, but not limit, the present invention(s):

EXAMPLE 1

Amplification of a Repertoire of IgM Heavy Chain Variable Genes $1^{st}$ Strand cDNA Synthesis and Modification Human peripheral blood lymphocyte (PBL) mRNA was used to generate traditional $1^{st}$ stand cDNA with an oligo dT primer using SuperScript First-Strand Synthesis System for RT-PCR (Invitrogen Life Technologies, Carlsbad, Calif.) essentially according to kit instructions. The first stand cDNA product was cleaned up over a QIAGEN spin column (PCR Purification Kit from QIAGEN, Valencia, Calif.). A restriction oligonucleotide was added to the first strand cDNA in order to generate a double stranded DNA region that could be digested by the restriction endonuclease EcoR I. The sequence of the restriction oligonucleotide (CMEcoR I) was 5' TCC TGT GAG AAT TCC CCG TCG 3' (Seq. ID No. 1). The reaction was set up with $1^{st}$ strand cDNA and 0.1 uM oligonucleotide. The sample was heated to 95° C. for 2 minutes and then held at 64° C. for two minutes to allow specific annealing to occur. An appropriate amount of 10× restriction buffer H (Roche Diagnostics) was added to the sample and further cooled to 37° C. The restriction endonuclease EcoR I (New England Biolabs, Beverly Mass.) was added and incubated at 37° C. for 30 minutes. The restriction enzyme was heat inactivated at 65° C. for 20 minutes and then the sample was cooled to 4° C.

$2^{nd}$ Strand Linear Amplification and Nested Oligo Extension

EcoR I digested $1^{st}$ strand cDNA was used as the original template in a $2^{nd}$ strand cDNA reaction along with primer "TMX24VH3a" (0.4 uM final), dNTPs, AmpliTaq enzyme and its 10× reaction buffer (Applied Biosystems, Foster City, Calif.). The primer was designed to contain the predetermined TMX24 sequence, an Xho I restriction site and a region that anneals to the $1^{st}$ strand cDNA in the framework 1 region of the human antibody heavy chain genes. The sequence of "TMX24VH3a" was 5' GTG CTG GCC GTT GGA AGA GGA GTG CTC GAG GAR GTG CAG CTG GTG GAG 3' (Seq. ID No. 2) where R stands for an equal molar mixture of bases A and G. The sample was heat denatured at 95° C. for 1 minute then cycled 20 times through 95° C. for 5 seconds, 56° C. for 10 seconds and 68° C. for 1 minute. This allows linear amplification of the 2nd strand cDNA. A nested oligo designated "TMX24CM0" was then added on ice to a final concentration of 0.08 uM. The sequence of "TMX24CM0" was 5' GTG CTG GCC GTT GGA AGA GGA GTG ACT AGT AAT TCT CAC AGG AGA CGA GGG GGA 3' (Seq. ID No. 3), which contains a Spe I restriction endonuclease site to be used in subsequent cloning steps. The 3' end of the nested oligo is designed to prevent elongation by incorporation of a reverse linked (3'-3' rather than 3'-5') adenosine. The $2^{nd}$ strand cDNAs were further elongated off the nested oligo by heat denaturing at 94° C. for 5 seconds, then cycled 4 times for annealing and elongating at 68° C. for 10 seconds and 95° for 5 seconds, followed by 68° for 30 seconds and 4° C. The resulting $2^{nd}$ strand cDNA or engineered template was then cleaned up using a QIAGEN spin column (PCR Purification Kit from QIAGEN, Valencia, Calif.). This step removes the oligonucleotides and allows simple buffer exchange for downstream protocols.

Single Primer Amplification (SPA)

The engineered template was amplified using Advantage 2 polymerase mix (Clontech) and its 10× reaction buffer, dNTPs, and a single primer (TMX24) having the sequence of 5' GTG CTG GCC GTT GGA AGA GGA GTG 3' (Seq. ID No. 4). The samples were heat denatured at 95° C. for 1 minute then cycled 35 times through 95° for 5 seconds and 68° C. for 1 minute. This was followed by an additional 3 minutes at 68° C. and a 4° C. hold.

Cloning and Sequencing

Amplification products of approximately 450 bp were gel purified and then digested by Xho I and Spe I and cloned into pBluescript KS+ (Stratagene). Individual clones were picked and their DNA sequence determined. All of the 16 clones analyzed were IgM heavy chain, each possessing a different CDR3 sequences of varying length thereby indicating that a diverse population of antibody chains were amplified by this method (see Table 1).

TABLE 1

|  |  | FR3 | HCDR3 | FR4 |
|---|---|---|---|---|
| CLONE 1 | (Seq. ID No.5) | YYCAR | EGSSSGAFDI | WGQ |
| CLONE 2 | (Seq. ID No.6) | YYCAR | AAFYCSGGSCYFDYYYYGMDV | WGQ |
| CLONE 3 | (Seq. ID No.7) | YYCAK | DIGGLGVLNFDY | WGQ |
| CLONE 5 | (Seq. ID No.8) | YYCAK | GVLAAIRICDY | WGQ |

TABLE 1-continued

|  |  | FR3 | HCDR3 | FR4 |
|---|---|---|---|---|
| CLONE 6 | (Seq. ID No.9) | YYCAR | DPGVYDYVWGSYRYPPDAFDI | WGQ |
| CLONE 7 | (Seq. ID No.10) | YYCAR | GMIVGATSYPDY | WGQ |
| CLONE 8 | (Seq. ID No.11) | YYCLL | GYCSSTSCPDAFDI | WGQ |
| CLONE 9 | (Seq. ID No.12) | YYCVI | GGAVFSGGSYRQQIDY | WGQ |
| CLONE 10 | (Seq. ID No.13) | YYCTR | DRGGSYTSHLGAFDI | WGQ |
| CLONE 11 | (Seq. ID No.14) | YYCAK | DNDLGGDYYYYGMDV | WGQ |
| CLONE 12 | (Seq. ID No.15) | YYCAR | DRRFPTDLFDI | WGQ |
| CLONE 13 | (Seq. ID No.16) | YYCAR | EDGYNSGWSYNWFDP | WGQ |
| CLONE 14 | (Seq. ID No.17) | YYCAK | DCVSGSYHYFDY | WGQ |
| CLONE 16 | (Seq. ID No.18) | YYCAK | DSYCSGGSCYYYYGVDV | WGQ |
| CLONE 17 | (Seq. ID No.19) | YYCAR | EVVPAAIIDYYYGMDV | WGQ |
| CLONE 18 | (Seq. ID No.20) | YYCAK | DLGIAVVVPAH | WGQ |

EXAMPLE 2

In order to clone VH products into a vector so that the native IgM CH1 constant region could be reconstituted, a site other than the EcoR I in CH1 was utilized for the $1^{st}$ strand cDNA endonuclease digestion. As those skilled in the art will appreciate, when Taq polymerase is used for this protocol, a terminal A is added to many of the newly synthesized DNA strands. In order to maximize diversity, the presence of that terminal A was taken into account in the design of the nested oligonucleotide. However, the presence of that extra A results in the loss of the EcoR I recognition site. Analysis of the IgM constant region revealed other native restriction sites that could potentially be used for this method, such as Dra III. The result of using the Dra III native restriction site in the CH1 domain is that the upstream EcoR I site remains unmodified and can be used for cloning the heavy chain repertoire. The heavy chain inserts are cloned by Xho I and EcoR I into an appropriate vector which has the remaining IgM CH1 domain from EcoR I to the CH2 domain.

$1^{st}$ Strand cDNA Synthesis and Modification

Human peripheral blood lymphocyte (PBL) mRNA was used to generate traditional $1^{st}$ stand cDNA with an oligo dT primer. This was done using SuperScript First-Strand Synthesis System for RT-PCR (Invitrogen Life Technologies, Carlsbad, Calif.) according essentially to kit instructions. A restriction oligonucleotide was added to the first strand cDNA in order to generate a double stranded DNA region that could be digested by the restriction endonuclease Dra III. The sequence of the restriction oligonucleotide (CMDra III) was 5' GAC GAA CAC GTG GTG TGC AAA G 3' (Seq. ID No. 21). The reaction was set up with $1^{st}$ strand cDNA and 1 uM oligonucleotide. The sample was heated to 95° C. for 2 minutes and then held at 64° C. for two minutes to allow specific annealing to occur. An appropriate amount of 10× restriction buffer H (Roche Diagnostics) was added to the sample and further cooled to 37° C. The restriction endonuclease Dra III (New England Biolabs, Beverly Mass.) was added and incubated at 37° C. for 30 minutes. The restriction enzyme was heat inactivated at 65° C. for 20 minutes and then the sample was cooled to 4° C.

$2^{nd}$ Strand Linear Amplification and Nested Oligo Extension

Figure 7:
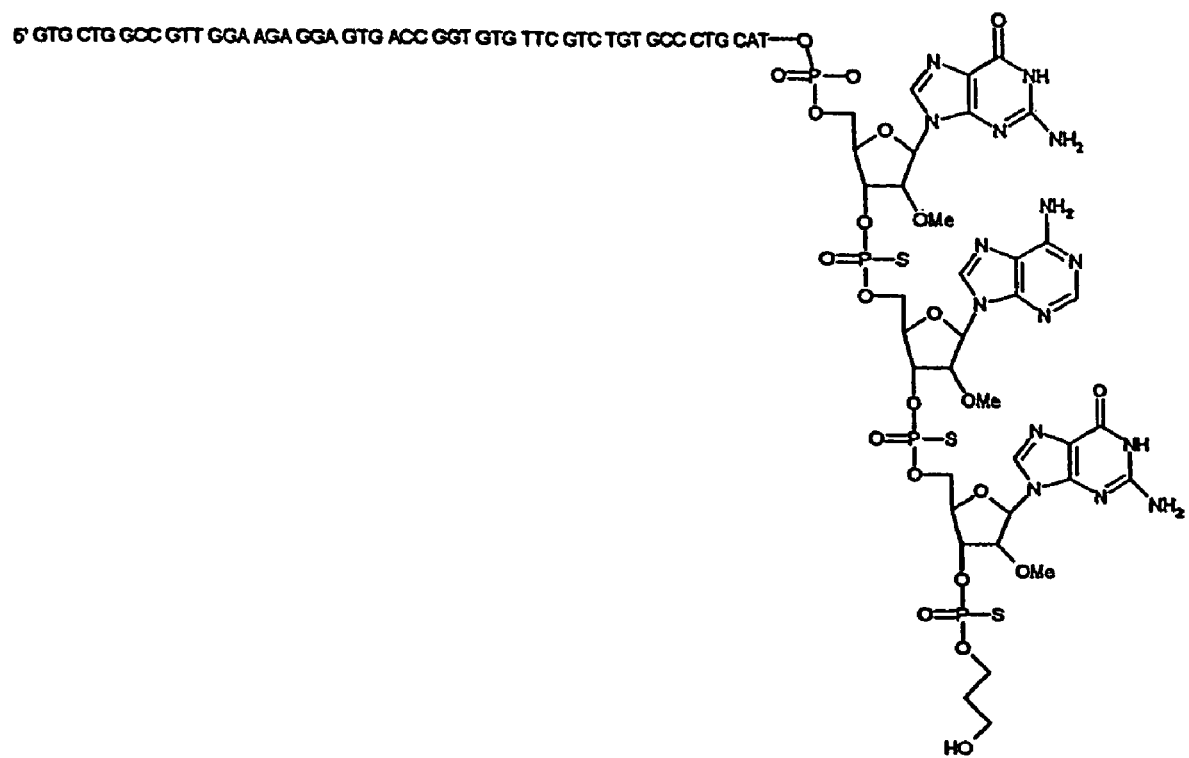
FIG. 7 shows the sequence of the nested oligo designated TMX24CMnpt.

Dra III digested $1^{st}$ strand cDNA was used as the original template in a $2^{nd}$ strand cDNA reaction along with primer "TMX24VH1a" (0.4 uM final), dNTPs, AmpliTaq enzyme and its 10× reaction buffer (Applied Biosystems, Foster City, Calif.). The primer was designed to contain the predetermined TMX24 sequence, an Xho I restriction site and a region that anneals to the $1^{st}$ strand cDNA in the framework 1 region of the human antibody heavy chain genes. The sequence of "TMX24VH1a" was 5'GTGCTGGCCGTTGGAAGAG-GAGTGCTCGAGCAGGTKCAGCTGGTGCAG 3' (Seq. ID No. 22) where K stands for an equal molar mixture of bases G and T. The sample was heat denatured at 94° C. for 1 minute then cycled 20 times through 94° C. for 5 seconds, 56° C. for 10 seconds and 68° C. for 2 minutes. This allowed linear amplification of the 2nd strand cDNA. A nested oligo designated "TMX24CMnpt" was added on ice to a final concentration of 0.2 uM. As shown in FIG. 7, the sequence of "TMX24CMnpt" (Seq. ID No. 23) includes three 3' terminal nucleotides having modified structures which were designed to prevent elongation of the oligonucleotide. Specifically, the nested oligo has three terminal nucleotides modified with phosphorthioate and 2' OMe which is designed to prevent extension and protect against exo- and endonuclease activity. The 3' end nucleotide of this oligo is non-hybridizing (g instead of c). The $2^{nd}$ strand cDNAs were further elongated off the nested oligo by heat denaturing at 94° C. for 1 minute, annealing and elongating at 68° C. for 2 minutes, followed by 4° C. The resulting $2^{nd}$ strand cDNA or engineered template was then cleaned up using a QIAGEN spin column (PCR Purification Kit from QIAGEN, Valencia, Calif.). This step removes the oligonucleotides and allows simple buffer exchange for downstream protocols. This procedure was repeated and extended to the rest of the VH primer panel (see primer list) to generate a library of immunoglobulin products that can be cloned into an appropriate vector.

```
VH Framework 1 Specific Primers:

PRIMER TMX24VH1a (Seq. ID No. 25)
GTGCTGGCCGTTGGAAGAGGAGTGCTCGAGCAGGTKCAGCTGGTGCAG

PRIMER TMX24VH1b (Seq. ID No. 26)
GTGCTGGCCGTTGGAAGAGGAGTGCTCGAGCAGGTCCAGCTTGTGCAG

PRIMER TMX24VH1c (Seq. ID No. 27)
GTGCTGGCCGTTGGAAGAGGAGTGCTCGAGSAGGTCCAAGCTGGTACAG

PRIMER TMX24VH1d (Seq. ID No. 28)
GTGCTGGCCGTTGGAAGAGGAGTGCTCGAGCARATGCAGCTGGTGCAG

PRIMER TMX24VH2a (Seq. ID No. 29)
GTGCTGGCCGTTGGAAGAGGAGTGCTCGAGCAGATCACCTTGAAGGAG

PRIMER TMX24VH2b (Seq. ID No. 30)
GTGCTGGCCGTTGGAAGAGGAGTGCTCGAGCAGGTCACCTTGARGGAG

PRIMER TMX24VH3a (Seq. ID No. 31)
GTGCTGGCCGTTGGAAGAGGAGTGCTCGAGGARGTGCAGCTGGTGGAG

PRIMER TMX24VH3b (Seq. ID No. 32)
GTGCTGGCCGTTGGAAGAGGAGTGCTCGAGCAGGTGCAGCTGGTGGAG

PRIMER TMX24VH3c (Seq. ID No. 33)
GTGCTGGCCGTTGGAAGAGGAGTGCTCGAGGAGGTGCAGCTGTTGGAG

PRIMER TMX24VH4a (Seq. ID No. 34)
GTGCTGGCCGTTGGAAGAGGAGTGCTCGAGCAGSTGCAGCTGCAGGAG

PRIMER TMX24VH4b (Seq. ID No. 35)
GTGCTGGCCGTTGGAAGAGGAGTGCTCGAGCAGGTGCAGCTACAGCAG

PRIMER TMX24VH5a (Seq. ID No. 36)
GTGCTGGCCGTTGGAAGAGGAGTGCTCGAGGARGTGCAGCTGGTGCAG

PRIMER TMX24VH6a (Seq. ID No. 37)
GTGCTGGCCGTTGGAAGAGGAGTGCTCGAGCAGGTACAGCTGCAGCAG

PRIMER TMX24VH7a (Seq. ID No. 38)
GTGCTGGCCGTTGGAAGAGGAGTGCTCGAGCAGGTSCAGCTGGTGCAA
```

In the foregoing sequences, R is an equal mixture of A and G, K is an equal mixture of G and T, and S is an equal mixture of C and G.

Single Primer Amplification (SPA)

The engineered template was amplified using Advantage 2 polymerase mix (Clontech) and its 10× reaction buffer, dNTPs and a single primer (TMX24) having the sequence 5' GTG CTG GCC GTT GGA AGA GGA GTG 3' (Seq. ID No. 4). The samples were heat denatured at 95° C. for 1 minute then cycled 30 times through 95° C. for 5 seconds and 68° C. for 1 minute. This was followed by an additional 3 minutes at 68° C. and a 4° hold.

Cloning and Sequencing

Amplification products of approximately 450 bp are gel purified and digested by Xho I and EcoR I. The inserts are cloned into the any suitable expression vector containing the remaining portion of the IgM CH1 domain from the native EcoR I site up to, or including a portion of, the CH2 domain and a compatible restriction site for cloning the amplified fragments.

EXAMPLE 3

Construction of a Phagmid Display Library From mRNA of a Hepatitis B Positive Donor.

1$^{st}$ Strand cDNA Synthesis and Modification for IgG Heavy and Kappa Light Chains Human peripheral blood lymphocyte (PBL) mRNA from a Hepatitis B vaccinated donor was used to generate traditional 1$^{st}$ stand cDNA with an oligo dT primer. This was done using SuperScript First-Strand Synthesis System for RT-PCR (Invitrogen Life Technologies, Carlsbad, Calif.) according essentially to kit instructions. Restriction oligonucleotide "CGApaL I" for IgG or "CKSac I" for kappa light chain was added to the first strand cDNA in order to generate a double stranded DNA region that could be digested by the restriction endonuclease ApaL I for IgG or Sac I for kappa light chain. "CGApaL I" sequences is 5'CCA GCG GCG TGC ACA CCT TCC3' (Seq ID No. 39). "CKSac I" sequence is 5'AGG GCC TGA GCT CGC CCG TC 3' (Seq ID No. 40). The reaction was set up with 1$^{st}$ strand cDNA, 1 uM oligonucleotide, and appropriate amount of 10× restriction buffer A(Roche Diagnostics). The sample was heated to 95° C. for 2 minutes and then held at 64° C. for two minutes to allow specific annealing to occur and cooled to 37° C. The restriction endonuclease ApaL I or Sac I (New England Biolabs, Beverly Mass.) was added and incubated at 37° C. for 30 minutes. The restriction enzyme was heat inactivated for Sac I at 65° C. for 20 minutes and then the sample was cooled to 4° C.

Digestion of the 1$^{st}$ strand cDNAs by each restriction endonuclease was verified by PCR amplification using techniques known to those skilled in the art. These products were not used for cloning the antibody genes. Positive amplification of the digested 1$^{st}$ strand cDNA was observed in reactions using the 5' VBVH1a and the 3'CG0 internal control primer for IgG and 5' VBVK1a and the 3'CK0 internal control primer for kappa. Good amplification with primers 5'VBVH1a/3'CG0 or 5' VBVK1a/3'CK0 and minimal amplification with primers 5' VBVH1a/3'CG1Z or 5' VK1a/3'CK1dx2 indicate successful digestion of the 1$^{st}$ strand cDNA template with each restriction endonuclease. Sequences of the primers used for check PCR were VBVH1a: 5' GAG CCG CAC GAG CCC CTC GAG CAG GTK CAG CTG GTG CAG 3' (Seq. ID No. 41), CG0: 5' GRG CGC CTG AGT TCC ACG ACA CCG 3' (Seq. ID No. 42), VBVK1a: 5' GAC GCG CAC AAC ACG GAG CTC RAC ATC CAG ATG ACC CAG 3' (Seq. ID No. 43), CK0: 5' GTG ACT TCG CAG GCG TAG ACT T 3' (Seq. ID No.44), CG1z: 5' GCA TGT ACT AGT TTT GTC ACA AGA TTT GGG 3' (Seq. ID No. 45), CK1dx2: 5' AGA CAG TGA GCG CCG TCT AGA ATT AAC ACT CTC CCC TGT TGA AGC TCT TTG TGA CGG GCG AAC TCA G 3' (Seq. ID No. 46).

Light Chain 2$^{nd}$ Strand Linear Amplification and Nested Oligo Extension

Sac I digested 1$^{st}$ strand cDNA was used as the original template to set up multiple 2$^{nd}$ strand cDNA reactions using a framework 1 specific primer (0.4 uM final), dNTPs, AmpliTaq enzyme and its 10× reaction buffer (Applied Biosystems, Foster City, Calif.). The primers were designed to contain predetermined TMX24K sequence 5'GAC GAC CG G CTA CCA AGA GGA GTG3' (Seq. ID No. 47) for kappa, an Xba I restriction site, and a region that annealed to 1$^{st}$ strand cDNA in the framework 1 region of human antibody kappa light chain genes. Those annealing sequences were derived from the VBase database primers (www.mrc-cpe.cam.ac.uk/imt-doc/public/INTRO.html) that were designed based on the known sequences of human antibodies and are reported to cover the entire human antibody repertoire of kappa light chain genes.

```
Kappa light Chain Framework 1 Specific Primers:

TMX24Vk1a (Seq. ID No. 48)
                                Xba I
GACGACCGGCTACCAAGAGGAGTGTCTAGARACATCCAGATGACCCAG
```

-continued

Kappa light Chain Framework 1 Specific Primers:

TMX24Vk1b (Seq. ID No. 49)
GACGACCGGCTACCAAGAGGAGTGTCTAGAGMCATCCAGTTGACCCAG

TMX24Vk1c (Seq. ID No. 50)
GACGACCGGCTACCAAGAGGAGTGTCTAGAGCCATCCRGATGACCCAG

TMX24Vk1d (Seq. ID No. 51)
GACGACCGGCTACCAAGAGGAGTGTCTAGAGTCATCTGGATGACCCAG

TMX24Vk2a (Seq. ID No. 52)
GACGACCGGCTACCAAGAGGAGTGTCTAGAGATATTGTGATGACCCAG

TMX24Vk2b (Seq. ID No. 53)
GACGACCGGCTACCAAGAGGAGTGTCTAGAGATRTTGTGATGACTCAG

TMX24Vk3a (Seq. ID No. 54)
GACGACCGGCTACCAAGAGGAGTGTCTAGAGAAATTGTGTTGACRCAG

TMX24Vk3b (Seq. ID No. 55)
GACGACCGGCTACCAAGAGGAGTGTCTAGAGAAATAGTGATGACGCAG

TMX24Vk3c (Seq. ID No. 56)
GACGACCGGCTACCAAGAGGAGTGTCTAGAGAAATTGTAATGACACAG

TMX24Vk4a (Seq. ID No. 57)
GACGACCGGCTACCAAGAGGAGTGTCTAGAGACATCGTGATGACCCAG

TMX24Vk5a (Seq. ID No. 58)
GACGACCGGCTACCAAGAGGAGTGTCTAGAGAAACGACACTCACGCAG

TMX24Vk6a (Seq. ID No. 59)
GACGACCGGCTACCAAGAGGAGTGTCTAGAGAAATTGTGCTGACTCAG

TMX24Vk6b (Seq. ID No. 60)
GACGACCGGCTACCAAGAGGAGTGTCTAGAGATGTTGTGATGACACAG

In the foregoing sequences, R is an equal mixture of A and G, M is an equal mixture of A and C, Y is an equal mixture of C and T, W is an equal mixture of A and T, and S is an equal mixture of C and G.

The samples were heat denatured at 94° C. for 1 minute then cycled 20 times through 94° C. for 5 seconds, 56° C. for 10 seconds, and 68° C. for 2 minutes. This allowed linear amplification of the 2nd strand cDNA. A nested oligo designated "TMX24CKnpt" for kappa chains was added on ice to a final concentration of 0.2 uM. "TMX24CKnpt" contains predetermined sequence TMX24K and the sequence was 5' GAC GAC CGG CTA CCA AGA GGA GTG CTC GAG CTC AGG CCC TGA TGG GTG ACT TCG CT 3' (Seq. ID No. 61). The $2^{nd}$ strand cDNAs were further elongated off the nested oligo by heat denaturing at 94° C. for 1 minute, annealing and elongating at 68° C. for 2 minutes, followed by 4° C. The resulting $2^{nd}$ strand cDNA (engineered template) were cleaned up using a QIAGEN spin column (PCR Purification Kit from QIAGEN, Valencia, Calif.). This step removes the free oligonucleotides and allows simple buffer exchange for downstream protocols.

Light Chain Single Primer Amplification (SPA)

The engineered template was amplified using Advantage 2 polymerase mix (Clontech) and its 10× reaction buffer, dNTPs, and primer "TMX24K" for kappa chains. The sequence for "TMX24K" is 5'GAC GAC CGG CTA CCA AGA GGA GTG 3' (Seq. ID No. 62). The samples were heat denatured at 95° C. for 1 minute then cycled 30 times through 95° C. for 5 seconds and 68° C. for 1 minute. This was followed by an additional 3 minutes at 68° C. and a 4° C. hold.

Light Chain Cloning

Kappa amplification products were gel purified and then digested by Xba I and Sac I. The inserts were cloned into a suitable expression vector that contains the remaining portion of the kappa light chain constant region. The ligated product was introduced into an *E. coli* by electroporation and grown overnight at 37° C. The following morning a DNA maxi prep (QIAGEN, Valencia, Calif.) was performed to recover the light chain library DNA. The light chain library DNA was then used in subsequent steps to clone in the heavy chain Fd fragments by Xho I/Age I to complete the construction of the library.

Heavy Chain $2^{nd}$ Strand Linear Amplification and Nested Oligo Extension

ApaL I digested $1^{st}$ strand cDNA was used as the original template to set up multiple $2^{nd}$ strand cDNA reactions using a framework 1 specific primer (0.4 uM final), dNTPs, AmpliTaq enzyme and its 10× reaction buffer (Applied Biosystems, Foster City, Calif.). The primers were designed to contain the predetermined TMX24 sequence, an Xho I restriction site, and a region that annealed to $1^{st}$ strand cDNA in the framework 1 region of human antibody heavy chain genes. Those annealing sequences were derived from the VBase database primers that were designed based on the known sequences of human antibodies and are reported to cover the entire human antibody repertoire of heavy chain genes.

Heavy chain Framework 1 Specific Primers:

TMX24VH1a (Seq. ID No. 63)
GTGCTGGCCGTTGGAAGAGGAGTGCTCGAGCAGGTKCAGCTGGTGCAG

TMX24VH1b (Seq. ID No. 64)
GTGCTGGCCGTTGGAAGAGGAGTGCTCGAGCAGGTCCAGCTTGTGCAG

TMX24VH1c (Seq. ID No. 65)
GTGCTGGCCGTTGGAAGAGGAGTGCTCGAGSAGGTCCAGCTGGTACAG

TMX24VH1d (Seq. ID No. 66)
GTGCTGGCCGTTGGAAGAGGAGTGCTCGAGCARATGCAGCTGGTGCAG

TMX24VH2a (Seq. ID No. 67)
GTGCTGGCCGTTGGAAGAGGAGTGCTCGAGCAGATCACCTTGAAGGAG

TMX24VH2b (Seq. ID No. 68)
GTGCTGGCCGTTGGAAGAGGAGTGCTCGAGCAGGTCACCTTGARGGAG

TMX24VH3a (Seq. ID No. 69)
GTGCTGGCCGTTGGAAGAGGAGTGCTCGAGGARGTGCAGCTGGTGGAG

TMX24VH3b (Seq. ID No. 70)
GTGCTGGCCGTTGGAAGAGGAGTGCTCGAGCAGGTGCAGCTGGTGGAG

TMX24VH3c (Seq. ID No. 71)
GTGCTGGCCGTTGGAAGAGGAGTGCTCGAGGAGGTGCAGCTGTTGGAG

TMX24VH4a (Seq. ID No. 72)
GTGCTGGCCGTTGGAAGAGGAGTGCTCGAGCAGSTGCAGCTGCAGGAG

TMX24VH4b (Seq. ID No. 73)
GTGCTGGCCGTTGGAAGAGGAGTGCTCGAGCAGGTGCAGCTACAGCAG

TMX24VH5a (Seq. ID No. 74)
GTGCTGGCCGTTGGAAGAGGAGTGCTCGAGGARGTGCAGCTGGTGCAG

TMX24VH6a (Seq. ID No. 75)
GTGCTGGCCGTTGGAAGAGGAGTGCTCGAGCAGGTACAGCTGCAGCAG

TMX24VH7a (Seq. ID No. 76)
GTGCTGGCCGTTGGAAGAGGAGTGCTCGAGCAGGTSCAGCTGGTGCAA

In the foregoing sequences, R is an equal mixture of A and G, K is an equal mixture of G and T, and S is an equal mixture of C and G.

The samples were heat denatured at 94° C. for 1 minute then cycled 20 times through 94° C. for 5 seconds, 56° C. for 10 seconds, and 68° C. for 2 minutes. This allowed linear amplification of the 2nd strand cDNA. A nested oligonucleotide designated "TMX24CGnpt" (sequence 5' GTG CTG GCC GTT GGA AGA GGA GTG TGT TTG CAC GCC GCT GGT CAG RGC GCC TGA GTT G 3' (Seq. ID No. 77)) was added on ice to a final concentration of 0.2 uM. As shown in FIG. 1 for the IgM nested oligo, the three 3' terminal nucleotides were modified to prevent oligo extension. The $2^{nd}$ strand cDNAs were further elongated off the nested oligo by heat denaturing at 94° C. for 1 minute, annealing and elongating at 68° C. for 2 minutes, followed by 4° C. The resulting $2^{nd}$ strand cDNA (the engineered template) was then cleaned up using a QIAGEN spin column (PCR Purification Kit from QIAGEN, Valencia, Calif.). This step removed the free oligonucleotides and allowed simple buffer exchange for downstream protocols.

Single Primer Amplification (SPA)

The engineered template was amplified using Advantage 2 polymerase mix (Clontech) and its 10× reaction buffer, dNTPs, and primer "TMX24". The samples was heat denatured at 95° C. for 1 minute then cycled 30 times through 95° C. for 5 seconds and 68° C. for 1 minute. This was followed by 3 additional minutes at 68° C. and a 4° C. hold.

Heavy Chain Cloning & Production of the Library

The amplified products were pooled and then gel purified. DNA was recovered with QIAquick PCR purification kit (QIAGEN, Valencia, Calif.). The DNA was sequentially digested with Xho I and Age I restriction enzymes and then gel purified. Age I site is naturally present in the CH1 of IgG constant region upstream of ApaL I site. DNA was recovered with QIAquick Gel extraction Kit (QIAGEN, Valencia, Calif.).

The light chain library DNA was digested sequentially with Xho I and Age I and then gel purified. The light chain library DNA was ligated with the heavy chain fragments. Ligated DNA was placed over a spin column (PCR purification Kit, QIAGEN, Valencia, Calif.) to remove the reaction buffer and to concentrate the DNA. Final transformation was done in electrocompetent XL-1 Blue cells (Stratagene).

Panning and Screening of Library on HBs Ag

The library was panned on immobilized HBs Ag for 4 rounds essentially as described in Barbas III, C F, Burton, D R, Scott, J K, and Silverman, G J (2001) Phage Display: A Laboratory Manual, Cold Spring Harbor Laboratory Press, Cold Spring Harbor, N.Y. Individual clones from the $2^{nd}$, $3^{rd}$, and $4^{th}$ rounds of panning were screened by ELISA on HBs Ag.

$1^{st}$ Strand cDNA Synthesis and Modification for Lambda Light Chain.

Human PBL mRNA from a Hepatitis B vaccinated donor was used to generate traditional $1^{st}$ strand cDNA with an oligo dT primer. This was done using SuperScript First-Strand Synthesis for RT-PCR (Invitrogen Life Technologies, Carlsbad, Calif.) according essentially to kit instructions. Restriction oligonucleotide "CLSma I" was added to the first strand cDNA in order to generate a double stranded DNA region that could be digested by the restriction endonuclease Sma I. "CLSma I" sequence is 5'GAC TTC TAC CCG GGA GCY GTG3' (Seq. ID No. 78) where Y is a mixture of C and T. The reaction was set up with $1^{st}$ strand cDNA, 1 uM oligonucleotide, and appropriate amount of 10× restriction buffer A (Roche Diagnostics). The sample was heated to 95° C. for 2 minutes and then held at 64° C. for two minutes to allow specific annealing to occur and cooled to 37° C. The restriction endonuclease Sma I (New England Biolabs, Beverly Mass.) was added and incubated at 37° C. for 30 minutes. The restriction enzyme was heat inactivated at 65° C. and then the sample was cooled to 4° C.

Digestion of the $1^{st}$ strand cDNA by restriction endonuclease was verified by PCR amplification using techniques known to those skilled in the art. These products were not used for cloning the antibody genes. Positive amplification of the digested $1^{st}$ strand cDNA was observed in reaction using the 5'VBVL1a and 3'CL0 internal control primer. Good amplification with primers 5'VBVL1a/3'CL0 and minimal amplification with primers 5'VBVL1a/3'CL2dx2 indicated successful digestion of the $1^{st}$ strand cDNA template with Sma I. Sequences of the primers for check PCR were VBVL1a 5' GAC GCG CAC A AC ACG GAG CTC CAG TCT GTG CTG ACT CAG 3' (Seq. ID No. 79), CL0 5'CCT CAG AGG AGG GYG GG A ACAG3' (Seq. ID No. 80) and CL2dx2 5' AGA CAG TGA CGC CGT CTA GAA TTA TGA ACA TTC TGT AGG 3' (Seq. ID No. 81).

Lambda Light Chain $2^{nd}$ Strand Linear Amplification and Nested Oligo Extension Sma I digested $1^{st}$ strand cDNA was used as the original template to set up multiple $2^{nd}$ strand cDNA reactions using a framework 1 specific primer (0.4 uM final), dNTPs, AmpliTaq enzyme and its 10× reaction buffer (Applied Biosystems, Foster City, Calif.). The primers are designed to contain predetermined TMX24L sequence, an Xba I site, and a region that anneals to $1^{st}$ strand cDNA in the framework region of human antibody lambda light chain genes. Those annealing sequences are derived from the VBase database primers (www.mrc-cpe.cam.ac.uk/imt-doc/public/INTRO.html) that are designed based on the known sequences of human antibodies and are reported to cover the entire human antibody repertoire of lambda light chain genes. Lambda light chain framework 1 specific primers are those used in Example 4.

The samples were heat denatured at 94° C. for 1 minute and then cycled 20 times through 94° C. for 5 seconds, 56° C. for 10 seconds, and 68° C. for 2 minutes. This allowed linear amplification of the $2^{nd}$ strand cDNA. A nested oligo nucleotide designated "TMX24CLnpt" as shown in Example 4 was added on ice to a final concentration of 0.2 uM. As shown in FIG. 7 for the IgM nested oligonucleotide "TMX24CMnpt", the 3' terminal nucleotides of "TMX24CLnpt" are modified to prevent oligo extension. The $2^{nd}$ strand cDNAs were further elongated off the nested oligonucleotide by heat denaturing at 94° C. for 1 minutes, annealing and elongating at 68° C. for 2 minutes, followed by 4° C. The resulting $2^{nd}$ strand cDNAs (the engineered template) were cleaned up using PCR Purification Kit (QIAGEN, Valencia, Calif.). This step removes the free oligonucleotides and allows simple buffer exchange for downstream protocols.

Lambda Light Chain Single Primer Amplification (SPA)

The engineered template was amplified using Advantage 2 polymerase mix (Clontech) and its 10× reaction buffer, dNTPs, and primer "TMX24L". The predetermined sequence of TMX24L is 5'GAC GAC CGG CTA CCA AGA GGA CAG3' (Seq. ID No. 82). The samples were heat denatured at 95° C. for 1 minutes then cycled 30 times through 95° C. for 5 seconds and 68° C. for 1 minute. This was followed by an additional 3 minutes at 68° C. and a 4° C. hold.

Lambda Light Chain Cloning

Lambda light chain amplification products were cleaned up by PCR purification kit (QIAGEN, Valencia, Calif.) and digested by Xba I and Sac I. The insert was gel purified using a gel extraction kit (QIAGEN, Valencia, Calif.) and cloned into an appropriate vector that contains the remaining portion of the lambda light chain constant region. The ligated product was introduced into an E. coli by electroporation and grown overnight at 37° C. The following morning a DNA maxi prep (QIAGEN, Valencia, Calif.) was performed to recover the lambda light chain library DNA.

Heavy Chain Cloning & Production of the IgG Lambda Library

The lambda light chain library DNA prepared above was sequentially digested by Xho I and Age I for the insertion of the heavy chain Fd fragments prepared also for the IgG kappa library as described previously. The ligated product was then introduced into an E. coli by electroporation and grown overnight at 37° C. The following morning a DNA maxi prep (QIAGEN, Valencia, Calif.) was performed to recover the complete IgG lambda library DNA.

Panning and Screening of Library on HBs Ag

The panning and screening was performed as described previously for IgG kappa library.

DNA Sequencing Analysis and Characterization of Isolated Fabs

Clones that showed specific binding to HBsAg and minimal binding to a non-specific protein, ovalbumin by ELISA screening were analyzed by DNA sequencing. See FIGS. 8a-e. Total of 38 distinct IgG kappa Fabs (25 heavy chains and 37 light chains) and 17 distinct IgG lambda Fabs (13 heavy chains and 16 light chains) to HBsAg were isolated from the libraries made from the PBL mRNA from a Hepatitis B vaccinated donor.

EXAMPLE 4

Construction of a Phage Display Antibody Library From Human PBL mRNA.

$1^{st}$ Strand cDNA Synthesis and Modification for Light Chains

Human PBL mRNA from donor was is to generate traditional $1^{st}$ stand cDNA with an oligo dT primer using SuperScript First-Strand Synthesis System for RT-PCR (Invitrogen Life Technologies, Carlsbad, Calif.) essentially according to kit instructions. Kappa and lambda light chain reactions are set up separately. Restriction oligonucleotide "CKSac I" or "CLSma I" is added to the first strand cDNA in order to generate a double stranded DNA region that could be digested by the restriction endonuclease Sac I for kappa or Sma I for lambda light chains. As there are multiple lambda constant regions (C1, C2, C3, and C6) it is important to note that the Sma I site is conserved among all functional lambda constant domains (C1, C2, C3, and C6). "CKSac I" sequence is 5'AGG GCC TGA GCT CGC CCG TC 3' (Seq ID No. 179), "CLSma I" sequence is 5' GAC TTC TAC CCG GGA GCY GTG 3' (Seq ID No. 180) where Y is a mixture of C and T. The reactions are set up with $1^{st}$ strand cDNA and 1 uM oligonucleotide. The sample is heated to 95° C. for 2 minutes and then held at 64° C. for two minutes to allow specific annealing to occur. An appropriate amount of 10× restriction buffer A (Roche Diagnostics) is added to the samples and further cooled to 37° C. The restriction endonuclease Sac I or Sma I (New England Biolabs, Beverly Mass.) is added and incubated at 37° C. for 30 minutes. The restriction enzyme is heat inactivated at 65° C. for 20 minutes and then the sample is cooled to 4° C.

Light Chain $2^{nd}$ Strand Linear Amplification and Nested Oligo Extension

Sac I digested kappa $1^{st}$ strand cDNA or Sma I digested lambda $1^{st}$ strand cDNA are used as the original templates to set up multiple $2^{nd}$ strand cDNA reactions using a framework 1 specific primer (0.4 uM final), dNTPs, AmpliTaq enzyme and its 10× reaction buffer (Applied Biosystems, Foster City, Calif.). The primers are designed to contain TMX24K (for kappa) or TMX24L (for lambda) sequence, an Xba I restriction site, and a region that annealed to $1^{st}$ strand cDNA in the framework 1 region of human antibody kappa or lambda chain genes. Those annealing sequences are derived from the VBase database primers (www.mrc-cpe.cam.ac.uk/imt-doc/public/INTRO.html) that are designed based on the known sequences of human antibodies and are reported to cover the entire human antibody repertoire of light chain genes. Kappa light chain framework 1 specific primers are those used in Example 3. See the following list of primers for use in lambda amplification.

```
Lambda light chain Framework 1 Specific Primers:

TMX24VL1a (Seq. ID No. 181)
GACGACCGGCTACCAAGAGGACAGTCTAGACAGTCTGTGCTGACTCAG

TMX24VL1b (Seq. ID No. 182)
GACGACCGGCTACCAAGAGGACAGTCTAGACAGTCTGTGYTGACGCAG

TMX24VL1C (Seq. ID No. 183)
GACGACCGGCTACCAAGAGGACAGTCTAGACAGTCTGTCGTGACGCAG

TMX24VL2 (Seq. ID No. 184)
GACGACCGGCTACCAAGAGGACAGTCTAGACAGTCTGCCCTGACTCAG

TMX24VL3a (Seq. ID No. 185)
GACGACCGGCTACCAAGAGGACAGTCTAGATCCTATGWGCTGACTCAG

TMX24VL3b (Seq. ID No. 186)
GACGACCGGCTACCAAGAGGACAGTCTAGATCCTATGAGCTGACACAG

TMX24VL3c (Seq. ID No. 187)
GACGACCGGCTACCAAGAGGACAGTCTAGATCTTCTGAGCTGACTCAG

TMX24VL3d (Seq. ID No. 188)
GACGACCGGCTACCAAGAGGACAGTCTAGATCCTATGAGCTGATGCAG

TMX24VL4 (Seq. ID No. 189)
GACGACCGGCTACCAAGAGGACAGTCTAGACAGCYTGTGCTGACTCAA

TMX24VL5 (Seq. ID No. 190)
GACGACCGGCTACCAAGAGGACAGTCTAGACAGSCTGTGCTGACTCAG

TMX24VL6 (Seq. ID No. 191)
GACGACCGGCTACCAAGAGGACAGTCTAGAAATTTTATGCTGACTCAG

TMX24VL7 (Seq. ID No. 192)
GACGACCGGCTACCAAGAGGACAGTCTAGACAGRCTGTGGTGACTCAG

TMX24VL8 (Seq. ID No. 193)
GACGACCGGCTACCAAGAGGACAGTCTAGACAGACTGTGGTGACCCAG

TMX24VL4/9 (Seq. ID No. 194)
GACGACCGGCTACCAAGAGGACAGTCTAGACWGCCTGTGCTGACTCAG

TMX24VL10 (Seq. ID No. 195)
GACGACCGGCTACCAAGAGGACAGTCTAGACAGGCAGGGCTGACTCAG
```

In the foregoing sequences, R is an equal mixture of A and G, M is an equal mixture of A and C, Y is an equal mixture of C and T, W is an equal mixture of A and T, and S is an equal mixture of C and G.

The samples are heat denatured at 94° C. for 1 minute then cycled 20 times through 94° C. for 5 seconds, 56° C. for 10 seconds, and 68° C. for 2 minutes. This allowed linear amplification of the 2nd strand cDNA. A nested oligonucleotide designated "TMX24CKnpt" for kappa chains or "TMX24CLnpt" for lambda chains are added on ice to a final concentration of 0.2 uM. The nested oligonucleotide sequences are; "TMX24CKnpt" 5' GAC GAC CGG CTA CCA AGA GGA GTG CTC GAG CTC AGG CCC TGA TGG GTG ACT TCG CT 3' (Seq. ID No. 196) and "TMX24CLnpt" 5' GAC GAC CGG CTA CCA AGA GGA CAG AAG AGC TCC TGG GTA GAA GTC ACT KAT SAG RCA CAG 3' (Seq. ID No. 197). As shown in FIG. 7 for the IgM nested oligo, the three 3' terminal nucleotides are modified to prevent oligo extension. The $2^{nd}$ strand cDNAs are further elongated off the nested oligos by heat denaturing at 94° C. 1 minute, annealing and elongating at 68° C. for 2 minutes, followed by 4° C. The resulting $2^{nd}$ strand cDNA (the engineered templates) are purified using a QIAGEN spin column (PCR Purification Kit from QIAGEN, Valencia, Calif.). This step removes the free oligonucleotides and allows simple buffer exchange for downstream protocols.

Light Chain Single Primer Amplification (SPA)

The engineered template is amplified using Advantage 2 polymerase mix (Clontech) and its 10× reaction buffer, dNTPs, and primer "TMX24K" for kappa chains, or "TMX24L" for lambda chains. The sequence for "TMX24K" is 5'GAC GAC CGG CTA CCA AGA GGA GTG 3' (Seq. ID No. 198), and for "TMX24L" it is 5' GAC GAC CGG CTA CCA AGA GGA CAG 3' (Seq. ID No. 199). The samples are heat denatured at 95° C. for 1 minute then cycled 30 times through 95° C. for 5 seconds and 68° C. for 1 minute. This is followed by an additional 3 minutes at 68° C. and a 4° C. hold.

Light Chain Cloning

Kappa and Lambda amplification products were cleaned using a PCR purification kit (QUIAGEN) and were separately gel purified. Those products are digested by Xba I and Sac I. The inserts are cloned into an appropriate vector that contains the remaining portion of the respective light chain constant region. The ligated product is introduced into *E. coli* by electroporation and grown overnight at 37° C. The following morning a DNA maxiprep is performed to recover the light chain library DNA. The light chain library DNA preps are used as the cloning vector for insertion of the heavy chain Fd fragments by Xho I/EcoR I to complete the construction of the library.

$1^{st}$ Strand cDNA Synthesis and Modification for Heavy Chains

Human PBL mRNA from a donor is used to generate traditional $1^{st}$ stand cDNA with an oligo dT primer. This is done using SuperScript First-Strand Synthesis System for RT-PCR (Invitrogen Life Technologies, Carlsbad, Calif.) according essentially to their instructions. Restriction oligonucleotide CMDra III is added to the first strand cDNA in order to generate a double stranded DNA region that could be digested by the restriction endonuclease Dra III. The reaction is set up with $1^{st}$ strand cDNA and 1 uM oligonucleotide. The sample is heated to 95° C. for 2 minutes and then held at 64° C. for two minutes to allow specific annealing to occur. An appropriate amount of 10× restriction buffer H (Roche Diagnostics) is added to the sample and further cooled to 37° C. The restriction endonuclease Dra III (New England Biolabs, Beverly Mass.) is added and incubated at 37° C. for 30 minutes followed by cooling at 4° C.

Digestion of the $1^{st}$ strand cDNAs by Dra III is verified by PCR amplification. Amplification products will not be used for cloning antibody fragments. Positive amplification of the digested $1^{st}$ strand cDNA is observed in reactions using the 5' VBVH1a and the 3'CM0 internal control primer under two different buffer conditions. Good amplification with primers 5'VBVH1a/3'CM0 and minimal amplification with primers 5' VBVH1a/3'CM1 indicate successful Dra III digestion of the $1^{st}$ strand cDNA template.

Heavy Chain $2^{nd}$ Strand Linear Amplification and Nested Oligo Extension

Dra III digested $1^{st}$ strand cDNA is used as the original template to set up multiple $2^{nd}$ strand cDNA reactions using a framework 1 specific primer (0.4 uM final), dNTPs, Ampli-Taq enzyme and its 10× reaction buffer (Applied Biosystems, Foster City, Calif.). The primers are designed to contain the TMX24 sequence, an Xho I restriction site, and a region that annealed to $1^{st}$ strand cDNA in the framework 1 region of human antibody heavy chain genes. Those annealing sequences are derived from the VBase database primers that are designed based on the known sequences of human antibodies and are reported to cover the entire human antibody repertoire of heavy chain genes as described above in example 3. Heavy chain framework 1 specific primers used are those as listed in example 3.

The samples are heat denatured at 94° C. for 1 minute then cycled 20 times through 94° C. for 5 seconds, 56° C. for 10 seconds, and 68° C. for 2 minutes. This allowed linear amplification of the 2nd strand cDNA. A nested oligo nucleotide designated "TMX24CMnpt" (as used in Example 3) is added on ice to a final concentration of 0.2 uM. The $2^{nd}$ strand cDNAs are further elongated off the nested oligo by heat denaturing at 94° C. for 1 minute, annealing and elongating at 68° C. for 2 minutes, followed by 4° C. The resulting $2^{nd}$ strand cDNA (engineered template) is then cleaned up using a QIAGEN spin column (PCR Purification Kit from QIAGEN, Valencia, Calif.). This step removed the free oligonucleotides and allowed simple buffer exchange for downstream protocols.

Heavy Chain Single Primer Amplification (SPA)

The engineered template is amplified using Advantage 2 polymerase mix (Clontech) and its 10× reaction buffer, dNTPs, and primer "TMX24". The samples are heat denatured at 95° C. for 1 minute then cycled 30 times through 95° C. for 5 seconds and 68° C. for 1 minute. This is followed by 3 additional minutes at 68° C. and a 4° C. hold.

Heavy Chain Cloning & Production of the Library

Amplification products of approximately 500 bp are gel purified and then digested by Xho I and EcoR I. The inserts are cloned into an appropriate vector contains the remaining portion of the IgM CH 1 domain. The ligated product containing a Fab library is introduced into *E. coli* by electroporation.

In order to produce the Fab library on the surface of bacteriophage, a suppressor strain of cells such as XL1BLUE (Stratagene) is used. Following electroporation, the cells are shaken for 1 hour at 37° then carbenicillin is added to 20 ug/ml. After one hour shaking at 37° C. the carbenicillin is increased to 50 ug/ml for an additional hour at 37° C. VCS-M13 helper phage (Stratagene) are then added to provide all the necessary components for generation of phagemid particles and the volume of the culture is increased to 100 mls of SB media. After an hour at 37° C. kanamycin is added to 70 ug/ml to select for those bacteria containing helper phage DNA. The culture is shaken at 37° overnight. During that time the bacteria produce new phagemid particles that have Fab displayed on its surface. The following morning the phagemid particles can be isolated by spinning out the bacterial cells and then precipitating the phagemid particles from the supernate with 4% PEG 8000 and 0.5 M NaCl on ice for 30 minutes. Precipitated phage pellet on centrifugation at 14,300×g. The pellet can be resuspended in PBS/1% BSA. The preparation can be filtered to remove bacterial debris. The resulting library is stored at 4°.

EXAMPLE 5

Construction of a Phagemid Display Library From mRNA of Mice Immunized With IgE or a Recombinant IgE Fc CH2~4.

$1^{st}$ Strand cDNA Synthesis and Modification for IgG Heavy and Kappa Light Chains Mouse spleen mRNA from mice immunized with human IgE or recombinant human IgE was used to generate traditional $1^{st}$ strand cDNA with an oligo dT primer. This was done using SuperScript First-Strand Synthesis for RT-PCR (Invitrogen Life Technologies, Carlsbad, Calif.) according essentially to kit instructions. Restriction oligonucleotide "mCG1Xcm I" for IgG1, "mCG2aBsaJ I" for IgG2a, or "mCKHpa I" for kappa light chain was added to the first strand cDNA in order to generate a double stranded DNA region that could be digested by the restriction endonuclease Xcm I for IgG1, BsaJ I for IgG2a, or Hpa I for kappa light chain. "mCG1Xcm I" sequences is 5'CTAACTCCAT GGTGACCCTGGGATG3' (Seq. ID No. 200). "mCG2aBsaJ I" sequence is 5'CAACTGGCTCCTCGGT GACTCTAG3' (Seq. ID No. 201), "mCKHpa I" sequence is 5'CAGTGAGCAGTTAACATCTGGAGG3' (Seq. No. 202). The reaction was set up with $1^{st}$ strand cDNA 1 uM oligonucleotide, and appropriate amount of 10× NEBuffer (New England Biolabs, Beverly Mass.) or 10× restriction buffer A(Roche Diagnostics). The sample was heated to 95° C. for 2 minutes and then held at 64° C. for two minutes to allow specific annealing to occur and cooled to 37° C. for Xcm I and Hpa I and 60° C. for BsaJ I. The restriction endonuclease Xcm I, BsaJ I, or Hpa I (New England Biolabs, Beverly Mass.) was added and incubated at 37° C. for 30 minutes, 60° C. for 30 min, and 37° C. for 10 minutes, respectively. The restriction enzyme was heat inactivated for Xcm I at 65° C. for 20 minutes and for BsaJ I at 80° C. for 20 min and then the sample was cooled to 4° C.

Digestion of the $1^{st}$ strand cDNAs by each restriction endonuclease was verified by PCR amplification using techniques known to those skilled in the art. These products were not used for cloning the antibody genes. Positive amplification of the digested $1^{st}$ strand cDNA was observed in reactions using the 5' TMX24 mVHIIBshort and the 3' mCG1 internal control primer for IgG1, 5' TMX24 mVHIIBshort and the 3' mCG2a internal control primer for IgG2a, and 5' TMX24 mVKIVshort and the 3' mCK0 internal control primer for kappa. Good amplification with primers 5' TMX24 mVHIIBshort/3' mCG1 or primers 5' TMX24 mVHIIBshort/3' mCG2a or 5' TMX24 mVKIVshort/3' mCK0 and minimal amplification with primers 5' TMX24 mVHIIBshort/3' mCG1B or 5' TMX24 mVHIIBshort/3' mCG2aB or 5' TMX24 mVKIVshort/3' mCKB indicate successful digestion of the $1^{st}$ strand cDNA template with each restriction endonuclease. Sequences of the primers used for check PCR were TMX24mVHIIBshort (Seq. ID No. 203)
5'GACGTGGCCGTTGGAAGAGGAGTGCTCGAGGTCCAACTGCAGCAGY
C3' mCG1 (Seq. ID No. 204)
5'CATGGAGTTAGTTTGGGCAGCAG3' mCG1B (Seq. ID No. 205)
5'CAACGTTGCAGGTGACGGTCTC3' mCG2a (Seq. ID No. 206)
5'CGAGGAGCCAGTTGTATCTCCAC3' mCG2aB (Seq. ID No. 207)
5'CCACATTGCAGGTGATGGACTG3'

TMX24mVKIVshort (Seq. ID No. 208)
5'GACGACCGGCTACCAAGAGGAGTGTCTAGAGAAAWTGTGCTCACCC
AGTCTC3' mCK0 (Seq. ID No. 209)
5'CTGCTCACTGGATGGTGGGAAG3' mCKB (Seq. ID No. 210)
5'GAGTGGCCTCACAGGTATAGCTG3'

Light Chain $2^{nd}$ Strand Linear Amplification and Nested Oligo Extension

Hpa I digested $1^{st}$ strand cDNA was used as the original template to set up multiple $2^{nd}$ strand cDNA reactions using a framework 1 specific primer (0.4 uM final), dNTPs, AmpliTaq enzyme and its 10× reaction buffer (Applied Biosystems, Foster City, Calif.). The primers were designed to contain TMX24mK sequence for kappa, and Xba I restriction site, and a region that annealed to $1^{st}$ strand cDNA in the framework 1 region of mouse antibody kappa light chain genes. Those annealing sequences were designed based on the known sequences of mouse antibodies derived from Kabat database (http://immuno.bme.nwu.edu/) to cover the entire mouse antibody repertoire of kappa light chain genes.

D. Kappa Framework 1 Specific Primers:

TMX24mVKIshort (Seq. ID No. 211)
                    Xba I
5'GACGACCGGCTACCAAGAGGAGTGTCTAGAGACATTGTGATGWCAC
AGTCTC3'

TMX24mVKIIashort (Seq. ID No. 212)
5'GACGACCGGCTACCAAGAGGAGTGTCTAGAGATGTTKTGATGACCC
ARACTC3'

TMX24mVKIIbshort (Seq. ID No. 213)
5'GACGACCGGCTACCAAGAGGAGTGTCTAGAGACATTGTGATGACKC
AGGCTG3'

TMX24mVKIIIshort (Seq. ID No. 214)
5'GACGACCGGCTACCAAGAGGAGTGTCTAGAGACAWTGTGCTGACCC
ARTCTC3'

TMX24mVKIVshort (Seq. ID No. 215)
5'GACGACCGGCTACCAAGAGGAGTGTCTAGAGAAAWTGTGCTCACCC
AGTCTC3'

TMX24mVKVashort (Seq. ID No. 216)
5'GACGACCGGCTACCAAGAGGAGTGTCTAGAGACATCCAGATGACMC
AGTCTC3'

TMX24mVKVbshort (Seq. ID No. 217)
5'GACGACCGGCTACCAAGAGGAGTGTCTAGAGATATCCAGATGACAC
AGACTAC3'

D. Kappa Framework 1 Specific Primers:

TMX24mVKVcshort (Seq. ID No. 218)
5'GACGACCGGCTACCAAGAGGAGTG<u>TCTAGA</u>GACATTGTSATGACCC
AGTC3'

TMX24mVKVIshort (Seq. ID No. 219)
5'GACGACCGGCTACCAAGAGGAGTG<u>TCTAGA</u>CAAATTGTTCTCACCC
AGTCTC3'

Wherein (R is and equal mixture of A and G, M is and equal mixture of A and C, K is and equal mixture of G and T, W is and equal mixture of A and T, and S is and equal mixture of C and G).

The samples were heat denatured at 94° C. for 1 minute then cycled 20 times through 94° C. for 5 seconds, 56° C. for 10 seconds, and 68° C. for 2 minutes. This allowed linear amplification of the $2^{nd}$ strand cDNA. A nested oligo designated "TMX24mCKnoer" for kappa chains was added on ice to a final concentration of 0.2 uM. The sequence of; "TM24CKnpt" was 5'GACGACCGGCTACCAAGAG-GAGTGTCCG GATGTTAACTGCTCACTGGATGGTGG GAAGATGG2'OMe[A(ps)U(ps)U(ps)] (propyl) 3' (Seq. ID No. 220). The $2^{nd}$ strand cDNAs were further elongated off the nested oligo by heat denaturing at 94° C. for 1 minute, annealing and elongating at 68° C. for 2 minutes, followed by 4° C. The resulting $2^{nd}$ strand cDNA (engineered template) were cleaned up using a QIAGEN spin column (PCR Purification Kit from QIAGEN, Valencia, Calif.). This step removes the free oligonucleotides and allows simple buffer exchange for downstream protocols.

Light Chain Single Primer Amplification (SPA)

The engineered template was amplified using Advantage 2 polymerase mix (Clontech) and its 10x reaction buffer, dNTPs, and primer "TMX24mK" for kappa chains. The sequence for "TMX24mK" is 5'GACGACCGGCTACCAA-GAGGAGTG3' (Seq. ID No. 221). The samples were heat denatured at 95° C. for 1 minute then cycled 25 times through 95° C. for 5 seconds and 68° C. for 1 minute. This was followed by an additional 3 minutes at 68° C. and a 4° hold.

Light Chain Cloning

Kappa amplification products were gel purified and then digested by Xba I and BspE I. The inserts were cloned into a suitable expression vector that contains the remaining portion of the kappa light chain constant region. The ligated product was introduced into *E. coli* by electroporation and grown overnight at 37° C. The following morning a DNA maxiprep was performed to recover the light chain library DNA. The light chain library DNA was used in subsequent steps to clone in the heavy chain Fd fragments by Xho I/Bln I to complete the construction of the library as described below in Heavy Chain Cloning.

Heavy Chain $2^{nd}$ Strand Linear Amplification and Nested Oligo Extension

Xcm I and BsaJ I digested $1^{st}$ strand cDNAs were used to set up multiple $2^{nd}$ strand cDNA reactions using framework 1 specific primer (0.4 uM final), dNTPs, AmpliTaq enzyme and its 10x reaction buffer (Applied Biosystems, Foster City, Calif.). The primers were designed to contain the TMX24mH sequence, an Xho I restriction site, and a region that annealed to $1^{st}$ strand cDNA in the framework 1 region of mouse antibody heavy chain genes. Those annealing sequences were designed based on the known sequences of mouse antibodies derived from Kabat database (http://immuno.bme.nwu.edu/) to cover the entire mouse antibody repertoire of heavy chain genes.

Heavy Chain Framework 1 Specific Primers:

TMX24mVHIAshorter (Seq. ID No. 222)
Xho I
5'GACGTGGCCGTTGGAAGAGGAGTG<u>CTCGAG</u>GTGCAGCTTCAGSAGT
C3'

TMX24mVHIBshorter (Seq. ID No. 223)
5'GACGTGGCCGTTGGAAGAGGAGTG<u>CTCGAG</u>GTGCAGCTGAAGSAGT
C3'

TMX24mVHIIAshorter (Seq. ID No. 224)
5'GACGTGGCCGTTGGAAGAGGAGTG<u>CTCGAG</u>GTYCAGCTGCARCART
C3'

TMX24mVHIIBshorter (Seq. ID No. 225)
5'GACGTGGCCGTTGGAAGAGGAGTG<u>CTCGAG</u>GTCCAACTGCAGCAGY
C3'

TMX24mVHIICshorter (Seq. ID No. 226)
5'GACGTGGCCGTTGGAAGAGGAGTG<u>CTCGAG</u>GTTCAGCTGCAGCAGT
C3'

TMX24mVHIIIAshorter (Seq. ID No. 227)
5'GACGTGGCCGTTGGAAGAGGAGTG<u>CTCGAG</u>GTGAAGCTGGTGGAGW
C3'

TMX24mVHIIIBshorter (Seq. ID No. 228)
5'GACGTGGCCGTTGGAAGAGGAGTG<u>CTCGAG</u>GTGAAGCTTCTGGAGT
C3'

TMX24mVHIIIDshorter (Seq. ID No. 229)
5'GACGTGGCCGTTGGAAGAGGAGTG<u>CTCGAG</u>GTGMAGCTGGTGGAGT
C3'

Wherein (R is an equal mixture of A and G, M is an equal mixture of A and C, Y is an equal mixture of C and T, and S is an equal mixture of C and G).

The samples were heat denatured at 94° C. for 1 minute then cycled 20 times through 94° C. for 5 seconds, 56° C. for 10 seconds, and 68° C. for 2 minutes. This allowed linear amplification of the $2^{nd}$ strand cDNA. A nested oligo designated "TMX24mCG1noer" for IgG1 and "TMX24mCG2anoer" for IgG2a was added on ice to a final concentration of 0.2 uM. The sequence of; "TMX24mCG1noer" was 5'GACGTGGCCGTTGGAA-GAGGAGTGCCTAGGGTTACCATGGAGTTAGTTTGG GCAGCAGA2'OMe[U(ps)C(ps)A(ps)](propyl) 3' (Seq. ID No. 230) and "TMX24mCG2anoer" was 5'GACGTGGC-CGTTGGAAGAGGAGTGCCTAGGGTCATC-GAGGAGCCAGTTGTA TCTCCACA2'OMe[C(ps)A(ps) U(ps)](propyl) 3' (Seq. ID No. 231).

The $2^{nd}$ strand cDNAs were further elongated off the nested oligo by heat denaturing at 94° C. for 1 minute, annealing and elongating at 68° C. for 2 minutes, followed by 4° C. The resulting $2^{nd}$ strand cDNA (engineered template) were cleaned up using a QIAGEN spin column (PCR Purification Kit from QIAGEN, Valencia, Calif.). This step removes the free oligonucleotides and allows simple buffer exchange for downstream protocols.

Heavy Chain Single Primer Amplification (SPA)

The engineered template was amplified using Advantage 2 polymerase mix (Clontech) and its 10x reaction buffer, dNTPs, and primer "TMX24mH" for heavy chains. The sequence for "TMX24mH" is 5' GACGTGGCCGTTGGAA- GAGGAGTG 3' (Seq. ID No. 232). The samples were heat denatured at 95° C. for 1 minute then cycled 28 times for IgG1 and 30 times for IgG2a through 95° C. for 5 seconds and 68° C. for 1 minute. This was followed by an additional 3 minutes at 68° C. and a 4° hold.

Heavy Chain Cloning

Heavy chain amplification products were gel purified and then digested by Xho I and Bln I. The inserts were cloned into kappa chain library DNAs that contain the remaining portion of the heavy chain constant region for IgG1 and IgG2a. The ligated product was introduced into E. coli by electroporation and grown overnight at 37° C. The following morning a DNA maxiprep was performed to recover the IgG1 kappa or IgG2a kappa library DNA.

Panning and Screening of Libraries on Recombinant IgE Fc CH2~4

The libraries panned on recombinant IgE Fc CH2~4 for 4 rounds essentially as described in Barbas III, C F Burton, D R, Scott, J K, and Silverman, G J (2001) Phage Display: A Laboratory Manual, Cold Spring Harbor Laboratory Press, Cold Spring Harbor, N.Y. Individual clones from the $2^{nd}$, $3^{rd}$, and $4^{th}$ rounds of panning were screened by ELISA on recombinant IgE Fc CH2~4.

Clones that showed specific binding to IgE IgE Fc CH2~4 and minimal binding to a non-specific protein, ovalbumin by ELISA were analyzed by DNA sequencing. A total of 31 distinct Fabs to IgE Fc CH2~4 were isolated from mice libraries. See FIGS. 9a-d.

EXAMPLE 6

Construction of IgA Antibody Libraries $1^{st}$ Strand cDNA Synthesis and Modification Human peripheral blood lymphocyte (PBL) mRNA are used to generate traditional $1^{st}$ stand cDNA with an oligo dT primer. This is done using SuperScript II RT cDNA Synthesis Kit (Invitrogen Life Technologies, Carlsbad, Calif.) according essentially to their instructions. Restriction oligonucleotide "CABsrG I" is added to the first strand cDNA in order to generate a double stranded DNA region that can be digested by the restriction endonuclease BsrG I. The sequence of "CABsrG I" is 5' TCC GGG GAC CTG TAC ACC ACG AGC AG 3' (SEQ ID NO 279). The reaction is set up with $1^{st}$ strand cDNA and 0.1 μM oligonucleotide. The sample is heated to 95° C. for 2 minutes and then held at 64° C. for 2 minutes to allow specific annealing to occur. An appropriate amount of 10× restriction buffer 2 (New England Biolabs, Beverly Mass.) is added to the sample and further cooled to 37° C. The restriction endonuclease BsrG I (New England Biolabs, Beverly Mass.) is added and incubated at 37° C. for 30 minutes. The restriction enzyme is heat inactivated at 80° C. for 20 minutes and then the sample is cooled to 4° C.

$2^{nd}$ Strand cDNA Synthesis and Nested Oligonucleotide Extension Reaction (NOER)

BsrG I digested $1^{st}$ strand cDNA is used to set up multiple $2^{nd}$ strand cDNA reactions using framework 1 specific primers (0.4 μM final), dNTPs, AmpliTaq enzyme and its 10× reaction buffer (Applied Biosystems, Foster City, Calif.). The primers, which are listed below in Table A, are designed to contain the TMX24 sequence, an Xho I restriction site, and a region that anneals to $1^{st}$ strand cDNA in the framework 1 region of human antibody heavy chain genes. Those annealing sequences are derived from the Vbase database primers that were designed based on the known sequences of human antibodies and are reported to cover the entire human repertoire of heavy chain genes.

TABLE A

Framework 1 Specific Primers:

TMX24VH1a (SEQ ID NO 280)
GTGCTGGCCGTTGGAAGAGGAGTGCTCGAGCAGGTKCAGCTGGTGCAG

TMX24VH1b (SEQ ID NO 281)
GTGCTGGCCGTTGGAAGAGGAGTGCTCGAGCAGGTCCAGCTTGTGCAG

TMX24VH1c (SEQ ID NO 282)
GTGCTGGCCGTTGGAAGAGGAGTGCTCGAGSAGGTCCAGCTGGTACAG

TMX24VH1d (SEQ ID NO 283)
GTGCTGGCCGTTGGAAGAGGAGTGCTCGAGCARATGCAGCTGGTGCAG

TMX24VH2a (SEQ ID NO 284)
GTGCTGGCCGTTGGAAGAGGAGTGCTCGAGCAGATCACCTTGAAGGAG

TMX24VH2b (SEQ ID NO 285)
GTGCTGGCCGTTGGAAGAGGAGTGCTCGAGCAGGTCACCTTGARGGAG

TMX24VH3a (SEQ ID NO 286)
GTGCTGGCCGTTGGAAGAGGAGTGCTCGAGGARGTGCAGCTGGTGGAG

TMX24VH3b (SEQ ID NO 287)
GTGCTGGCCGTTGGAAGAGGAGTGCTCGAGCAGGTGCAGCTGGTGGAG

TMX24VH3c (SEQ ID NO 288)
GTGCTGGCCGTTGGAAGAGGAGTGCTCGAGGAGGTGCAGCTGTTGGAG

TMX24VH4a (SEQ ID NO 289)
GTGCTGGCCGTTGGAAGAGGAGTGCTCGAGCAGSTGCAGCTGCAGGAG

TMX24VH4b (SEQ ID NO 290)
GTGCTGGCCGTTGGAAGAGGAGTGCTCGAGCAGGTGCAGCTACAGCAG

TMX24VH5a (SEQ ID NO 291)
GTGCTGGCCGTTGGAAGAGGAGTGCTCGAGGARGTGCAGCTGGTGCAG

TMX24VH6a (SEQ ID NO 292)
GTGCTGGCCGTTGGAAGAGGAGTGCTCGAGCAGGTACAGCTGCAGCAG

TMX24VH7a (SEQ ID NO 293)
GTGCTGGCCGTTGGAAGAGGAGTGCTCGAGCAGGTSCAGCTGGTGCAA

In each of the foregoing sequences, R is A or G, K is G or T, and S is C or G.

The sample is heat denatured at 94° C. for 1 minute then cycled 20 times through 94° C. for 5 seconds, 56° C. for 10 seconds, and 68° C. for 2 minutes. This allows linear amplification of the 2nd strand cDNA. The extension oligonucleotide "TMX24CAnpt" is then added on ice to a final concentration of 0.2 μM. The sequence of "TMX24CAnpt" is 5' GTG CTG GCC GTT GGA AGA GGA GTG CCT GTA CAG GTC CCC GGA GGC ATC CTC 3' (SEQ ID NO 294), wherein R is A or G. The three 3' terminal nucleotides are modified to prevent oligo extension. The $2^{nd}$ strand cDNAs is further elongated off the oligonucleotide by heat denaturing at 94° C. for 1 minute, elongating at 68° C. for 2 minutes, followed by 4° C. The $2^{nd}$ strand cDNA is then cleaned up using a QIAGEN spin column (PCR Purification Kit from QIAGEN, Valencia, Calif.). This step removes the oligonucleotides and allows simple buffer exchange for downstream protocols.

Single Primer PCR Amplification

PCR amplification of the $2^{nd}$ strand cDNA is performed using Advantage 2 polymerase mix (Clontech, Palo Alto, Calif.) and its 10× reaction buffer, dNTPs, and primer "TMX24". The sequence of "TMX24" is 5' GTG CTG GCC GTT GGA AGA GGA GTG 3' (SEQ ID NO 295). The samples is heat denatured at 95° C. for 1 minute then cycled 30 times through 95° C. for 5 seconds and 68° C. for 1 minute. This is followed by an additional 3 minutes at 68° C. and a 4° C. hold.

Cloning and Sequencing

PCR products of approximately 560 bp are purified using a PCR purification kit (QIAGEN, Valencia, Calif.), digested by Xho I and BsrG I, gel purified and cloned into a suitable Fab expression vector with the rest of the IgA CH1 constant region.

It will be understood that various modifications may be made to the embodiments described herein. Therefore, the above description should not be construed as limiting, but merely as exemplifications of preferred embodiments. Those skilled in the art will envision other modifications within the scope and spirit of this disclosure.

What is claimed is:

1. A library of IgA antibodies prepared in accordance with a method, said method comprising:
   a) providing a diverse population of templates that encode at least a portion of an IgA antibody;
   b) contacting the diverse population of templates with at least one primer, the at least one primer having a first portion which anneals to the templates and a second portion of predetermined sequence which does not anneal to the templates;
   c) synthesizing polynucleotides that are complementary to the portion of the templates between the location at which the first portion of the primer anneals to the template and the end of the templates, each of the polynucleotides having a primer at a first end thereof and a second end;
   d) separating the polynucleotides synthesized in step (c) from the templates;
   e) annealing at least one template oligonucleotide to the second end of the polynucleotides synthesized in step (c), the at least one template oligonucicotide having a first portion that anneals to the second end of the polynucleotides and a second portion having the same predetermined sequence as the second portion of the primer;

f) extending the polynucleotides synthesized in step (c) to provide a terminal portion thereof that is complementary to the predetermined sequence; and g) amplifying the extended polynucleotides using only a single primer, wherein the single primer has the predetermined sequence.

2. The library of igA antibodies of claim 1, wherein at least one-primer of step (b) comprises a sequence selected from the group consisting of:

| | |
|---|---|
| CTCGAGCAGGTKCAGCTGGTGCAG, | (SEQ ID NO 296) |
| CTCGAGCAGGTCCAGCTTGTGCAG, | (SEQ ID NO 297) |
| CTCGAGSAGGTCCAGCTGGTACAG, | (SEQ ID NO 298) |
| CTCGAGCARATGCAGCTGGTGCAG, | (SEQ ID NO 299) |
| CTCGAGCAGATCACCTTGAAGGAG, | (SEQ ID NO 300) |
| CTCGAGCAGGTCACCTTGARGGAG, | (SEQ ID NO 301) |
| CTCGAGGARGTGCAGCTGGTGGAG, | (SEQ ID NO 302) |
| CTCGAGCAGGTGCAGCTGGTGGAG, | (SEQ ID NO 303) |
| CTCGAGGAGGTGCAGCTGTTGGAG, | (SEQ ID NO 304) |
| CTCGAGCAGSTGCAGCTGCAGGAG, | (SEQ ID NO 305) |
| CTCGAGCAGGTGCAGCTACAGCAG, | (SEQ ID NO 306) |
| CTCGAGGARGTGCAGCTGGTGCAG, | (SEQ ID NO 307) |
| CTCGAGCAGGTACAGCTGCAGCAG | (SEQ ID NO 308) | and

| | |
|---|---|
| CTCGAGCAGGTSCAGCTGGTGCAA, | (SEQ ID NO 309) | wherein R is A or G, K is G or T, and S is C or G.

* * * * *

UNITED STATES PATENT AND TRADEMARK OFFICE
CERTIFICATE OF CORRECTION

| | | |
|---|---|---|
| PATENT NO. | : 7,414,111 B2 | Page 1 of 1 |
| APPLICATION NO. | : 10/737252 | |
| DATED | : August 19, 2008 | |
| INVENTOR(S) | : Toshiaki et al. | |

It is certified that error appears in the above-identified patent and that said Letters Patent is hereby corrected as shown below:

Col. 189 in Claim 1, line 63, delete the word "oligonucicotide" and replace it with --oligonucleotide--

Col. 191 in Claim 2, line 7, delete the word "igA" and replace it with --IgA--

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,414,111 B2 | Page 1 of 1 |
| APPLICATION NO. | : 10/737252 | |
| DATED | : August 19, 2008 | |
| INVENTOR(S) | : Maruyama et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 549 days Delete the phrase "by 549 days" and insert -- by 815 days --

Signed and Sealed this

Fourth Day of May, 2010

David J. Kappos
*Director of the United States Patent and Trademark Office*

SEQUENCE LISTING

```
<160> NUMBER OF SEQ ID NOS: 309

<210> SEQ ID NO 1
<211> LENGTH: 21
<212> TYPE: DNA
<213> ORGANISM: artificial sequence
<220> FEATURE:
<223> OTHER INFORMATION: restriction oligonucleotide

<400> SEQUENCE: 1
tcctgtgaga attccccgtc g                                         21

<210> SEQ ID NO 2
<211> LENGTH: 48
<212> TYPE: DNA
<213> ORGANISM: artificial sequence
<220> FEATURE:
<223> OTHER INFORMATION: primer

<400> SEQUENCE: 2
gtgctggccg ttggaagagg agtgctcgag gargtgcagc tggtggag            48

<210> SEQ ID NO 3
<211> LENGTH: 54
<212> TYPE: DNA
<213> ORGANISM: artificial sequence
<220> FEATURE:
<223> OTHER INFORMATION: nested oligo

<400> SEQUENCE: 3
gtgctggccg ttggaagagg agtgactagt aattctcaca ggagacgagg ggga     54

<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4
gtgctggccg ttggaagagg agtg                                      24

<210> SEQ ID NO 5
<211> LENGTH: 18
<212> TYPE: PRT
<213> ORGANISM: human

<400> SEQUENCE: 5

Tyr Tyr Cys Ala Arg Glu Gly Ser Ser Ser Gly Ala Phe Asp Ile Trp
1               5                   10                  15

Gly Gln

<210> SEQ ID NO 6
<211> LENGTH: 29
<212> TYPE: PRT
<213> ORGANISM: human
```

-continued

<400> SEQUENCE: 6

Tyr Tyr Cys Ala Arg Ala Ala Phe Tyr Cys Ser Gly Gly Ser Cys Tyr
1               5                   10                  15
Phe Asp Tyr Tyr Tyr Gly Met Asp Val Trp Gly Gln
            20                  25

<210> SEQ ID NO 7
<211> LENGTH: 20
<212> TYPE: PRT
<213> ORGANISM: human

<400> SEQUENCE: 7

Tyr Tyr Cys Ala Lys Asp Ile Gly Gly Leu Gly Val Leu Asn Phe Asp
1               5                   10                  15
Tyr Trp Gly Gln
            20

<210> SEQ ID NO 8
<211> LENGTH: 19
<212> TYPE: PRT
<213> ORGANISM: human

<400> SEQUENCE: 8

Tyr Tyr Cys Ala Lys Gly Val Leu Ala Ala Ile Arg Ile Cys Asp Tyr
1               5                   10                  15
Trp Gly Gln

<210> SEQ ID NO 9
<211> LENGTH: 29
<212> TYPE: PRT
<213> ORGANISM: human

<400> SEQUENCE: 9

Tyr Tyr Cys Ala Arg Asp Pro Gly Val Tyr Asp Tyr Val Trp Gly Ser
1               5                   10                  15
Tyr Arg Tyr Pro Pro Asp Ala Phe Asp Ile Trp Gly Gln
            20                  25

<210> SEQ ID NO 10
<211> LENGTH: 20
<212> TYPE: PRT
<213> ORGANISM: human

<400> SEQUENCE: 10

Tyr Tyr Cys Ala Arg Gly Met Ile Val Gly Ala Thr Ser Tyr Pro Asp
1               5                   10                  15
Tyr Trp Gly Gln
            20

<210> SEQ ID NO 11
<211> LENGTH: 22
<212> TYPE: PRT
<213> ORGANISM: human

<400> SEQUENCE: 11

Tyr Tyr Cys Leu Leu Gly Tyr Cys Ser Ser Thr Ser Cys Pro Asp Ala
1               5                   10                  15
Phe Asp Ile Trp Gly Gln
            20

-continued

```
<210> SEQ ID NO 12
<211> LENGTH: 24
<212> TYPE: PRT
<213> ORGANISM: human

<400> SEQUENCE: 12

Tyr Tyr Cys Val Ile Gly Gly Ala Val Phe Ser Gly Gly Ser Tyr Arg
1               5                   10                  15

Gln Gln Ile Asp Tyr Trp Gly Gln
            20

<210> SEQ ID NO 13
<211> LENGTH: 23
<212> TYPE: PRT
<213> ORGANISM: human

<400> SEQUENCE: 13

Tyr Tyr Cys Thr Arg Asp Arg Gly Gly Ser Tyr Thr Ser His Leu Gly
1               5                   10                  15

Ala Phe Asp Ile Trp Gly Gln
            20

<210> SEQ ID NO 14
<211> LENGTH: 23
<212> TYPE: PRT
<213> ORGANISM: human

<400> SEQUENCE: 14

Tyr Tyr Cys Ala Lys Asp Asn Asp Leu Gly Gly Asp Tyr Tyr Tyr Tyr
1               5                   10                  15

Gly Met Asp Val Trp Gly Gln
            20

<210> SEQ ID NO 15
<211> LENGTH: 19
<212> TYPE: PRT
<213> ORGANISM: human

<400> SEQUENCE: 15

Tyr Tyr Cys Ala Arg Asp Arg Arg Phe Pro Thr Asp Leu Phe Asp Ile
1               5                   10                  15

Trp Gly Gln

<210> SEQ ID NO 16
<211> LENGTH: 23
<212> TYPE: PRT
<213> ORGANISM: human

<400> SEQUENCE: 16

Tyr Tyr Cys Ala Arg Glu Asp Gly Tyr Asn Ser Gly Trp Ser Tyr Asn
1               5                   10                  15

Trp Phe Asp Pro Trp Gly Gln
            20

<210> SEQ ID NO 17
<211> LENGTH: 20
<212> TYPE: PRT
<213> ORGANISM: human

<400> SEQUENCE: 17

Tyr Tyr Cys Ala Lys Asp Cys Val Ser Gly Ser Tyr His Tyr Phe Asp
1               5                   10                  15
```

Tyr Trp Gly Gln
        20

<210> SEQ ID NO 18
<211> LENGTH: 25
<212> TYPE: PRT
<213> ORGANISM: human

<400> SEQUENCE: 18

Tyr Tyr Cys Ala Lys Asp Ser Tyr Cys Ser Gly Gly Ser Cys Tyr Tyr
1               5                   10                  15

Tyr Tyr Gly Val Asp Val Trp Gly Gln
            20                  25

<210> SEQ ID NO 19
<211> LENGTH: 24
<212> TYPE: PRT
<213> ORGANISM: human

<400> SEQUENCE: 19

Tyr Tyr Cys Ala Arg Glu Val Val Pro Ala Ala Ile Ile Asp Tyr Tyr
1               5                   10                  15

Tyr Gly Met Asp Val Trp Gly Gln
            20

<210> SEQ ID NO 20
<211> LENGTH: 19
<212> TYPE: PRT
<213> ORGANISM: human

<400> SEQUENCE: 20

Tyr Tyr Cys Ala Lys Asp Leu Gly Ile Ala Val Val Val Pro Ala His
1               5                   10                  15

Trp Gly Gln

<210> SEQ ID NO 21
<211> LENGTH: 22
<212> TYPE: DNA
<213> ORGANISM: artificial sequence
<220> FEATURE:
<223> OTHER INFORMATION: restriction oligonucleotide

<400> SEQUENCE: 21
gacgaacacg tggtgtgcaa ag                                          22

<210> SEQ ID NO 22
<211> LENGTH: 48
<212> TYPE: DNA
<213> ORGANISM: artificial sequence
<220> FEATURE:
<223> OTHER INFORMATION: primer

<400> SEQUENCE: 22
gtgctggccg ttggaagagg agtgctcgag caggtkcagc tggtgcag              48

<210> SEQ ID NO 23
<211> LENGTH: 51
<212> TYPE: DNA
<213> ORGANISM: artificial sequence
<220> FEATURE:
<223> OTHER INFORMATION: oligonucleotide

<400> SEQUENCE: 23
gtgctggccg ttggaagagg agtgaccggt gtgttcgtct gtgccctgca t          51

<210> SEQ ID NO 24

<400> SEQUENCE: 24

000

<210> SEQ ID NO 25
<211> LENGTH: 48
<212> TYPE: DNA
<213> ORGANISM: artificial sequence
<220> FEATURE:
<223> OTHER INFORMATION: primer

<400> SEQUENCE: 25
gtgctggccg ttggaagagg agtgctcgag caggtkcagc tggtgcag        48

<210> SEQ ID NO 26
<211> LENGTH: 48
<212> TYPE: DNA
<213> ORGANISM: artificial sequence
<220> FEATURE:
<223> OTHER INFORMATION: primer

<400> SEQUENCE: 26
gtgctggccg ttggaagagg agtgctcgag caggtccagc ttgtgcag        48

<210> SEQ ID NO 27
<211> LENGTH: 48
<212> TYPE: DNA
<213> ORGANISM: artificial sequence
<220> FEATURE:
<223> OTHER INFORMATION: primer

<400> SEQUENCE: 27
gtgctggccg ttggaagagg agtgctcgag saggtccagc tggtacag        48

<210> SEQ ID NO 28
<211> LENGTH: 48
<212> TYPE: DNA
<213> ORGANISM: artificial sequence
<220> FEATURE:
<223> OTHER INFORMATION: primer

<400> SEQUENCE: 28
gtgctggccg ttggaagagg agtgctcgag caratgcagc tggtgcag        48

<210> SEQ ID NO 29
<211> LENGTH: 48
<212> TYPE: DNA
<213> ORGANISM: artificial sequence
<220> FEATURE:
<223> OTHER INFORMATION: primer

<400> SEQUENCE: 29
gtgctggccg ttggaagagg agtgctcgag cagatcacct tgaaggag        48

<210> SEQ ID NO 30
<211> LENGTH: 48
<212> TYPE: DNA
<213> ORGANISM: artificial sequence
<220> FEATURE:
<223> OTHER INFORMATION: primer

<400> SEQUENCE: 30
gtgctggccg ttggaagagg agtgctcgag caggtcacct tgarggag        48

<210> SEQ ID NO 31
<211> LENGTH: 48
<212> TYPE: DNA
<213> ORGANISM: artificial sequence
<220> FEATURE:
<223> OTHER INFORMATION: primer

<400> SEQUENCE: 31
gtgctggccg ttggaagagg agtgctcgag gargtgcagc tggtggag        48

<210> SEQ ID NO 32
<211> LENGTH: 48
<212> TYPE: DNA
<213> ORGANISM: artificial sequence
<220> FEATURE:
<223> OTHER INFORMATION: primer

<400> SEQUENCE: 32
gtgctggccg ttggaagagg agtgctcgag caggtgcagc tggtggag        48

<210> SEQ ID NO 33
<211> LENGTH: 48
<212> TYPE: DNA
<213> ORGANISM: artificial sequence
<220> FEATURE:
<223> OTHER INFORMATION: primer

<400> SEQUENCE: 33
gtgctggccg ttggaagagg agtgctcgag gaggtgcagc tgttggag        48

<210> SEQ ID NO 34
<211> LENGTH: 48
<212> TYPE: DNA
<213> ORGANISM: artificial sequence
<220> FEATURE:
<223> OTHER INFORMATION: primer

<400> SEQUENCE: 34
gtgctggccg ttggaagagg agtgctcgag cagstgcagc tgcaggag        48

<210> SEQ ID NO 35
<211> LENGTH: 48
<212> TYPE: DNA
<213> ORGANISM: artificial sequence
<220> FEATURE:
<223> OTHER INFORMATION: primer

<400> SEQUENCE: 35
gtgctggccg ttggaagagg agtgctcgag caggtgcagc tacagcag        48

<210> SEQ ID NO 36
<211> LENGTH: 48
<212> TYPE: DNA
<213> ORGANISM: artificial sequence
<220> FEATURE:
<223> OTHER INFORMATION: primer

<400> SEQUENCE: 36
gtgctggccg ttggaagagg agtgctcgag gargtgcagc tggtgcag        48

<210> SEQ ID NO 37
<211> LENGTH: 48
<212> TYPE: DNA
<213> ORGANISM: artificial sequence
<220> FEATURE:

```
<223> OTHER INFORMATION: primer

<400> SEQUENCE: 37
gtgctggccg ttggaagagg agtgctcgag caggtacagc tgcagcag                    48

<210> SEQ ID NO 38
<211> LENGTH: 48
<212> TYPE: DNA
<213> ORGANISM: artificial sequence
<220> FEATURE:
<223> OTHER INFORMATION: primer

<400> SEQUENCE: 38
gtgctggccg ttggaagagg agtgctcgag caggtscagc tggtgcaa                    48

<210> SEQ ID NO 39
<211> LENGTH: 21
<212> TYPE: DNA
<213> ORGANISM: artificial sequence
<220> FEATURE:
<223> OTHER INFORMATION: restriction oligonucleotide

<400> SEQUENCE: 39
ccagcggcgt gcacaccttc c                                                 21

<210> SEQ ID NO 40
<211> LENGTH: 20
<212> TYPE: DNA
<213> ORGANISM: artificial sequence
<220> FEATURE:
<223> OTHER INFORMATION: restriction oligonucleotide

<400> SEQUENCE: 40
agggcctgag ctcgcccgtc                                                   20

<210> SEQ ID NO 41
<211> LENGTH: 39
<212> TYPE: DNA
<213> ORGANISM: artificial sequence
<220> FEATURE:
<223> OTHER INFORMATION: primer

<400> SEQUENCE: 41
gagccgcacg agcccctcga gcaggtkcag ctggtgcag                              39

<210> SEQ ID NO 42
<211> LENGTH: 24
<212> TYPE: DNA
<213> ORGANISM: artificial sequence
<220> FEATURE:
<223> OTHER INFORMATION: primer

<400> SEQUENCE: 42
grgcgcctga gttccacgac accg                                              24

<210> SEQ ID NO 43
<211> LENGTH: 39
<212> TYPE: DNA
<213> ORGANISM: artificial sequence
<220> FEATURE:
<223> OTHER INFORMATION: primer

<400> SEQUENCE: 43
gacgcgcaca acacggagct cracatccag atgacccag                              39
```

```
<210> SEQ ID NO 44
<211> LENGTH: 22
<212> TYPE: DNA
<213> ORGANISM: artificial sequence
<220> FEATURE:
<223> OTHER INFORMATION: primer

<400> SEQUENCE: 44
gtgacttcgc aggcgtagac tt                                             22

<210> SEQ ID NO 45
<211> LENGTH: 30
<212> TYPE: DNA
<213> ORGANISM: artificial sequence
<220> FEATURE:
<223> OTHER INFORMATION: primer

<400> SEQUENCE: 45
gcatgtacta gttttgtcac aagatttggg                                     30

<210> SEQ ID NO 46
<211> LENGTH: 67
<212> TYPE: DNA
<213> ORGANISM: artificial sequence
<220> FEATURE:
<223> OTHER INFORMATION: primer

<400> SEQUENCE: 46
agacagtgag cgccgtctag aattaacact ctcccctgtt gaagctcttt gtgacgggcg    60
aactcag                                                              67

<210> SEQ ID NO 47
<211> LENGTH: 24
<212> TYPE: DNA
<213> ORGANISM: artificial sequence
<220> FEATURE:
<223> OTHER INFORMATION: primer

<400> SEQUENCE: 47
gacgaccggc taccaagagg agtg                                           24

<210> SEQ ID NO 48
<211> LENGTH: 48
<212> TYPE: DNA
<213> ORGANISM: artificial sequence
<220> FEATURE:
<223> OTHER INFORMATION: primer

<400> SEQUENCE: 48
gacgaccggc taccaagagg agtgtctaga racatccaga tgacccag                 48

<210> SEQ ID NO 49
<211> LENGTH: 48
<212> TYPE: DNA
<213> ORGANISM: artificial sequence
<220> FEATURE:
<223> OTHER INFORMATION: primer

<400> SEQUENCE: 49
gacgaccggc taccaagagg agtgtctaga gmcatccagt tgacccag                 48

<210> SEQ ID NO 50
<211> LENGTH: 48
<212> TYPE: DNA
<213> ORGANISM: artificial sequence
<220> FEATURE:
```

<223> OTHER INFORMATION: primer

<400> SEQUENCE: 50
gacgaccggc taccaagagg agtgtctaga gccatccrga tgacccag         48

<210> SEQ ID NO 51
<211> LENGTH: 48
<212> TYPE: DNA
<213> ORGANISM: artificial sequence
<220> FEATURE:
<223> OTHER INFORMATION: primer

<400> SEQUENCE: 51
gacgaccggc taccaagagg agtgtctaga gtcatctgga tgacccag         48

<210> SEQ ID NO 52
<211> LENGTH: 48
<212> TYPE: DNA
<213> ORGANISM: artificial sequence
<220> FEATURE:
<223> OTHER INFORMATION: primer

<400> SEQUENCE: 52
gacgaccggc taccaagagg agtgtctaga gatattgtga tgacccag         48

<210> SEQ ID NO 53
<211> LENGTH: 48
<212> TYPE: DNA
<213> ORGANISM: artificial sequence
<220> FEATURE:
<223> OTHER INFORMATION: primer

<400> SEQUENCE: 53
gacgaccggc taccaagagg agtgtctaga gatrttgtga tgactcag         48

<210> SEQ ID NO 54
<211> LENGTH: 48
<212> TYPE: DNA
<213> ORGANISM: artificial sequence
<220> FEATURE:
<223> OTHER INFORMATION: primer

<400> SEQUENCE: 54
gacgaccggc taccaagagg agtgtctaga gaaattgtgt tgacrcag         48

<210> SEQ ID NO 55
<211> LENGTH: 48
<212> TYPE: DNA
<213> ORGANISM: artificial sequence
<220> FEATURE:
<223> OTHER INFORMATION: primer

<400> SEQUENCE: 55
gacgaccggc taccaagagg agtgtctaga gaaatagtga tgacgcag         48

<210> SEQ ID NO 56
<211> LENGTH: 48
<212> TYPE: DNA
<213> ORGANISM: artificial sequence
<220> FEATURE:
<223> OTHER INFORMATION: primer

<400> SEQUENCE: 56
gacgaccggc taccaagagg agtgtctaga gaaattgtaa tgacacag         48

<210> SEQ ID NO 57
<211> LENGTH: 48
<212> TYPE: DNA
<213> ORGANISM: artificial sequence
<220> FEATURE:
<223> OTHER INFORMATION: primer

<400> SEQUENCE: 57
gacgaccggc taccaagagg agtgtctaga gacatcgtga tgacccag                 48

<210> SEQ ID NO 58
<211> LENGTH: 48
<212> TYPE: DNA
<213> ORGANISM: artificial sequence
<220> FEATURE:
<223> OTHER INFORMATION: primer

<400> SEQUENCE: 58
gacgaccggc taccaagagg agtgtctaga gaaacgacac tcacgcag                 48

<210> SEQ ID NO 59
<211> LENGTH: 48
<212> TYPE: DNA
<213> ORGANISM: artificial sequence
<220> FEATURE:
<223> OTHER INFORMATION: primer

<400> SEQUENCE: 59
gacgaccggc taccaagagg agtgtctaga gaaattgtgc tgactcag                 48

<210> SEQ ID NO 60
<211> LENGTH: 48
<212> TYPE: DNA
<213> ORGANISM: artificial sequence
<220> FEATURE:
<223> OTHER INFORMATION: primer

<400> SEQUENCE: 60
gacgaccggc taccaagagg agtgtctaga gatgttgtga tgacacag                 48

<210> SEQ ID NO 61
<211> LENGTH: 56
<212> TYPE: DNA
<213> ORGANISM: artificial sequence
<220> FEATURE:
<223> OTHER INFORMATION: nested oligo

<400> SEQUENCE: 61
gacgaccggc taccaagagg agtgctcgag ctcaggccct gatgggtgac ttcgct        56

<210> SEQ ID NO 62
<211> LENGTH: 24
<212> TYPE: DNA
<213> ORGANISM: artificial sequence
<220> FEATURE:
<223> OTHER INFORMATION: primer

<400> SEQUENCE: 62
gacgaccggc taccaagagg agtg                                           24

<210> SEQ ID NO 63
<211> LENGTH: 48
<212> TYPE: DNA
<213> ORGANISM: artificial sequence
<220> FEATURE:
<223> OTHER INFORMATION: primer

<400> SEQUENCE: 63
gtgctggccg ttggaagagg agtgctcgag caggtkcagc tggtgcag         48

<210> SEQ ID NO 64
<211> LENGTH: 48
<212> TYPE: DNA
<213> ORGANISM: artificial sequence
<220> FEATURE:
<223> OTHER INFORMATION: primer

<400> SEQUENCE: 64
gtgctggccg ttggaagagg agtgctcgag caggtccagc ttgtgcag         48

<210> SEQ ID NO 65
<211> LENGTH: 48
<212> TYPE: DNA
<213> ORGANISM: artificial sequence
<220> FEATURE:
<223> OTHER INFORMATION: primer

<400> SEQUENCE: 65
gtgctggccg ttggaagagg agtgctcgag saggtccagc tggtacag         48

<210> SEQ ID NO 66
<211> LENGTH: 48
<212> TYPE: DNA
<213> ORGANISM: artificial sequence
<220> FEATURE:
<223> OTHER INFORMATION: primer

<400> SEQUENCE: 66
gtgctggccg ttggaagagg agtgctcgag caratgcagc tggtgcag         48

<210> SEQ ID NO 67
<211> LENGTH: 48
<212> TYPE: DNA
<213> ORGANISM: artificial sequence
<220> FEATURE:
<223> OTHER INFORMATION: primer

<400> SEQUENCE: 67
gtgctggccg ttggaagagg agtgctcgag cagatcacct tgaaggag         48

<210> SEQ ID NO 68
<211> LENGTH: 48
<212> TYPE: DNA
<213> ORGANISM: artificial sequence
<220> FEATURE:
<223> OTHER INFORMATION: primer

<400> SEQUENCE: 68
gtgctggccg ttggaagagg agtgctcgag caggtcacct tgarggag         48

<210> SEQ ID NO 69
<211> LENGTH: 48
<212> TYPE: DNA
<213> ORGANISM: artificial sequence
<220> FEATURE:
<223> OTHER INFORMATION: primer

<400> SEQUENCE: 69
gtgctggccg ttggaagagg agtgctcgag gargtgcagc tggtggag         48

<210> SEQ ID NO 70
<211> LENGTH: 48

```
<212> TYPE: DNA
<213> ORGANISM: artificial sequence
<220> FEATURE:
<223> OTHER INFORMATION: primer

<400> SEQUENCE: 70
gtgctggccg ttggaagagg agtgctcgag caggtgcagc tggtggag        48

<210> SEQ ID NO 71
<211> LENGTH: 48
<212> TYPE: DNA
<213> ORGANISM: artificial sequence
<220> FEATURE:
<223> OTHER INFORMATION: primer

<400> SEQUENCE: 71
gtgctggccg ttggaagagg agtgctcgag gaggtgcagc tgttggag        48

<210> SEQ ID NO 72
<211> LENGTH: 48
<212> TYPE: DNA
<213> ORGANISM: artificial sequence
<220> FEATURE:
<223> OTHER INFORMATION: primer

<400> SEQUENCE: 72
gtgctggccg ttggaagagg agtgctcgag cagstgcagc tgcaggag        48

<210> SEQ ID NO 73
<211> LENGTH: 48
<212> TYPE: DNA
<213> ORGANISM: artificial sequence
<220> FEATURE:
<223> OTHER INFORMATION: primer

<400> SEQUENCE: 73
gtgctggccg ttggaagagg agtgctcgag caggtgcagc tacagcag        48

<210> SEQ ID NO 74
<211> LENGTH: 48
<212> TYPE: DNA
<213> ORGANISM: artificial sequence
<220> FEATURE:
<223> OTHER INFORMATION: primer

<400> SEQUENCE: 74
gtgctggccg ttggaagagg agtgctcgag gargtgcagc tggtgcag        48

<210> SEQ ID NO 75
<211> LENGTH: 48
<212> TYPE: DNA
<213> ORGANISM: artificial sequence
<220> FEATURE:
<223> OTHER INFORMATION: primer

<400> SEQUENCE: 75
gtgctggccg ttggaagagg agtgctcgag caggtacagc tgcagcag        48

<210> SEQ ID NO 76
<211> LENGTH: 48
<212> TYPE: DNA
<213> ORGANISM: artificial sequence
<220> FEATURE:
<223> OTHER INFORMATION: primer

<400> SEQUENCE: 76
```

```
gtgctggccg ttggaagagg agtgctcgag caggtscagc tggtgcaa                    48
```

<210> SEQ ID NO 77
<211> LENGTH: 58
<212> TYPE: DNA
<213> ORGANISM: artificial sequence
<220> FEATURE:
<223> OTHER INFORMATION: nested oligonucleotide

<400> SEQUENCE: 77

```
gtgctggccg ttggaagagg agtgtgtttg cacgccgctg gtcagrgcgc ctgagttg        58
```

<210> SEQ ID NO 78
<211> LENGTH: 21
<212> TYPE: DNA
<213> ORGANISM: artificial sequence
<220> FEATURE:
<223> OTHER INFORMATION: restriction oligonucleotide

<400> SEQUENCE: 78

```
gacttctacc cgggagcygt g                                                 21
```

<210> SEQ ID NO 79
<211> LENGTH: 39
<212> TYPE: DNA
<213> ORGANISM: artificial sequence
<220> FEATURE:
<223> OTHER INFORMATION: primer

<400> SEQUENCE: 79

```
gacgcgcaca acacggagct ccagtctgtg ctgactcag                              39
```

<210> SEQ ID NO 80
<211> LENGTH: 22
<212> TYPE: DNA
<213> ORGANISM: artificial sequence
<220> FEATURE:
<223> OTHER INFORMATION: primer

<400> SEQUENCE: 80

```
cctcagagga gggygggaac ag                                                22
```

<210> SEQ ID NO 81
<211> LENGTH: 39
<212> TYPE: DNA
<213> ORGANISM: artificial sequence
<220> FEATURE:
<223> OTHER INFORMATION: primer

<400> SEQUENCE: 81

```
agacagtgac gccgtctaga attatgaaca ttctgtagg                              39
```

<210> SEQ ID NO 82
<211> LENGTH: 24
<212> TYPE: DNA
<213> ORGANISM: artificial sequence
<220> FEATURE:
<223> OTHER INFORMATION: primer

<400> SEQUENCE: 82

```
gacgaccggc taccaagagg acag                                              24
```

<210> SEQ ID NO 83
<211> LENGTH: 122
<212> TYPE: PRT
<213> ORGANISM: human

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Thr Met Asn Trp Val Arg Gln Ala Pro Gly Lys Gly Leu Glu Trp Ile
        35                  40                  45

Ser Tyr Ile Ser Thr Thr Ser Ser Ile Tyr Tyr Ala Asp Ser Val
    50                  55                  60

Lys Gly Arg Phe Ser Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Phe Phe Val Glu Gly Ser Tyr Trp Ser Phe Asp Leu Trp
            100                 105                 110

Gly Arg Gly Thr Leu Val Thr Val Ser Ser
            115                 120

<210> SEQ ID NO 84
<211> LENGTH: 122
<212> TYPE: PRT
<213> ORGANISM: human

<400> SEQUENCE: 84

Gln Val Gln Leu Leu Glu Ser Gly Gly Val Val Gln Pro Gly Thr
1               5                   10                  15

Ser Leu Thr Leu Ser Cys Thr Ala Ser Gly Phe Thr Phe Gly Ser Tyr
            20                  25                  30

Thr Met Asn Trp Val Arg Gln Ala Pro Gly Lys Gly Leu Glu Trp Ile
        35                  40                  45

Ser Tyr Ile Ser Thr Thr Ser Ser Ile Tyr Tyr Ala Asp Ser Val
    50                  55                  60

Lys Gly Arg Phe Ser Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Phe Phe Val Glu Gly Ser Tyr Trp Ser Phe Asp Leu Trp
            100                 105                 110

Gly Arg Gly Thr Leu Val Thr Val Ser Ser
            115                 120

<210> SEQ ID NO 85
<211> LENGTH: 122
<212> TYPE: PRT
<213> ORGANISM: human

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Thr Met Asn Trp Val Arg Gln Ala Pro Gly Lys Gly Leu Glu Trp Ile
        35                  40                  45

Ser Tyr Ile Ser Thr Thr Ser Ser Ile Tyr Tyr Ala Asp Ser Val
    50                  55                  60

```
Lys Gly Arg Phe Ser Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
             85                  90                  95

Ala Arg Val Phe Phe Val Glu Gly Ser Tyr Trp Ser Phe Asp Leu Trp
            100                 105                 110

Gly Arg Gly Thr Leu Val Thr Val Ser Ser
        115                 120

<210> SEQ ID NO 86
<211> LENGTH: 122
<212> TYPE: PRT
<213> ORGANISM: human

<400> SEQUENCE: 86

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Tyr
             20                  25                  30

Thr Met Asn Trp Val Arg Gln Ala Pro Gly Lys Gly Leu Glu Trp Ile
             35                  40                  45

Ser Tyr Ile Ser Thr Ser Ser Ser Ile Tyr Tyr Ala Asp Ser Val
         50                  55                  60

Lys Gly Arg Phe Ser Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
             85                  90                  95

Ala Arg Val Phe Phe Val Glu Gly Ser Tyr Trp Ser Phe Asp Leu Trp
            100                 105                 110

Gly Arg Gly Thr Leu Val Thr Val Ser Ser
        115                 120

<210> SEQ ID NO 87
<211> LENGTH: 122
<212> TYPE: PRT
<213> ORGANISM: human

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Ser
             20                  25                  30

Ala Met Ser Trp Val Arg Gln Ala Pro Gly Lys Gly Leu Glu Trp Val
             35                  40                  45

Ser Val Asn Ser Gly Asn Gly Phe Ser Thr Tyr Tyr Ala Asp Ser Val
         50                  55                  60

Lys Gly Arg Phe Ser Ile Ser Arg Asp Asn Ser Lys Asn Thr Val Tyr
 65                  70                  75                  80

Leu Glu Met Ser Ser Leu Arg Ala Glu Asp Thr Ala Lys Tyr Tyr Cys
             85                  90                  95

Val Lys Val Lys Tyr Gly Ser Arg Ser His Phe Phe Phe Asp Arg Trp
            100                 105                 110

Gly Gln Gly Thr Leu Val Thr Val Ser Ser
        115                 120

<210> SEQ ID NO 88
<211> LENGTH: 122
```

```
<212> TYPE: PRT
<213> ORGANISM: human

<400> SEQUENCE: 88

Gln Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Leu Ser Ser Ser
            20                  25                  30

Ala Met Ser Trp Val Arg Gln Ala Pro Gly Lys Gly Leu Glu Trp Val
        35                  40                  45

Ser Val Ser Ser Gly Asn Gly Phe Ser Thr Tyr Tyr Ala Asp Ser Val
    50                  55                  60

Lys Gly Arg Phe Ser Ile Ser Arg Asp Asn Ser Lys Asn Thr Val Tyr
65                  70                  75                  80

Leu Glu Met Ser Ser Leu Arg Ala Glu Asp Thr Ala Lys Tyr Tyr Cys
                85                  90                  95

Val Lys Val Lys Tyr Gly Ser Arg Ser His Phe Phe Phe Asp Arg Trp
            100                 105                 110

Gly Gln Gly Thr Leu Val Thr Val Ser Ser
        115                 120

<210> SEQ ID NO 89
<211> LENGTH: 122
<212> TYPE: PRT
<213> ORGANISM: human

<400> SEQUENCE: 89

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Ser
            20                  25                  30

Ala Met Ser Trp Val Arg Gln Ala Pro Gly Lys Gly Leu Glu Trp Val
        35                  40                  45

Ser Val Asn Ser Gly Asn Gly Phe Ser Thr Tyr Tyr Ala Asp Ser Val
    50                  55                  60

Lys Gly Arg Phe Ser Ile Ser Arg Asp Asn Ser Lys Asn Thr Val Tyr
65                  70                  75                  80

Leu Glu Met Ser Ser Leu Arg Ala Glu Asp Thr Ala Lys Tyr Tyr Cys
                85                  90                  95

Val Lys Val Lys Tyr Gly Ser Arg Ser His Phe Phe Phe Asp Arg Trp
            100                 105                 110

Gly Gln Gly Thr Leu Val Thr Val Ser Ser
        115                 120

<210> SEQ ID NO 90
<211> LENGTH: 122
<212> TYPE: PRT
<213> ORGANISM: human

<400> SEQUENCE: 90

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Ser
            20                  25                  30

Ala Met Ser Trp Val Arg Gln Ala Pro Gly Lys Gly Leu Glu Trp Val
        35                  40                  45

Ser Val Asn Ser Gly Asn Gly Phe Ser Thr Tyr Tyr Ala Asp Ser Val
```

```
            50                  55                  60
Lys Gly Arg Phe Ser Ile Ser Arg Asp Asn Ser Lys Asn Thr Val Tyr
 65                  70                  75                  80

Leu Glu Met Ser Ser Leu Arg Ala Glu Asp Thr Ala Lys Tyr Tyr Cys
                 85                  90                  95

Val Lys Val Lys Tyr Gly Ser Arg Ser His Phe Phe Phe Asp Arg Trp
                100                 105                 110

Gly Gln Gly Thr Leu Val Thr Val Ser Ser
            115                 120

<210> SEQ ID NO 91
<211> LENGTH: 122
<212> TYPE: PRT
<213> ORGANISM: human

<400> SEQUENCE: 91

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Leu Ser Ser Ser
                 20                  25                  30

Ala Met Ser Trp Val Arg Gln Ala Pro Gly Asx Gly Leu Glu Trp Val
                 35                  40                  45

Ser Val Asn Ser Gly Asn Gly Phe Ser Thr Tyr Tyr Ala Asp Ser Val
             50                  55                  60

Lys Gly Arg Phe Ser Ile Ser Arg Asp Asn Ser Lys Asn Thr Val Tyr
 65                  70                  75                  80

Leu Glu Met Ser Ser Leu Arg Ala Glu Asp Thr Ala Lys Tyr Tyr Cys
                 85                  90                  95

Val Lys Val Lys Tyr Gly Ser Arg Ser His Phe Phe Phe Asp Arg Trp
                100                 105                 110

Gly Gln Gly Thr Leu Val Thr Val Ser Ser
            115                 120

<210> SEQ ID NO 92
<211> LENGTH: 122
<212> TYPE: PRT
<213> ORGANISM: human

<400> SEQUENCE: 92

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Ser
                 20                  25                  30

Ala Met Ser Trp Val Arg Gln Ala Pro Gly Lys Gly Leu Glu Trp Val
                 35                  40                  45

Ser Val Ile Ser Gly Asn Gly Phe Ser Thr Tyr Tyr Ala Asp Ser Val
             50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Glu Tyr Tyr Cys
                 85                  90                  95

Ala Asn Val Lys Tyr Gly Ser Gly Ser His Phe Trp Phe Asp Pro Trp
                100                 105                 110

Gly Gln Gly Thr Leu Val Thr Val Ser Ser
            115                 120
```

<210> SEQ ID NO 93
<211> LENGTH: 122
<212> TYPE: PRT
<213> ORGANISM: human

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Val Ile Ser Gly Asn Gly Phe Ser Thr Tyr Tyr Ala Asp Ser Val
    50                  55                  60

Lys Gly Arg Phe Ser Ile Ser Arg Asp Asn Lys Asn Thr Leu Tyr
65                  70                  75                  80

Leu Gln Met Asn Ser Leu Arg Ala Glu Asp Thr Ala Glu Tyr Tyr Cys
                85                  90                  95

Thr Lys Val Lys Tyr Gly Ser Gly Ser His Phe Trp Phe Asp Pro Trp
            100                 105                 110

Gly Gln Gly Thr Leu Val Thr Val Ser Ser
        115                 120

<210> SEQ ID NO 94
<211> LENGTH: 121
<212> TYPE: PRT
<213> ORGANISM: human

<400> SEQUENCE: 94

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Phe Met His Trp Val Arg Gln Ala Pro Gly Glu Gly Leu Glu Trp Met
        35                  40                  45

Gly Leu Val Asn Pro Thr Asn Gly Tyr Thr Ala Tyr Ala Pro Lys Phe
    50                  55                  60

Gln Gly Arg Val Thr Met Thr Arg Gln Arg Phe Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Val Arg Ser Ser Asp Ser Ile Asp Ala Phe Asp Ile Trp Gly
            100                 105                 110

Gln Gly Thr Met Val Ile Val Ser Ser
        115                 120

<210> SEQ ID NO 95
<211> LENGTH: 121
<212> TYPE: PRT
<213> ORGANISM: human

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Phe Met His Trp Val Arg Gln Ala Pro Gly Gln Gly Leu Glu Trp Met
        35                  40                  45

Gly Leu Val Asn Pro Thr Asn Gly Tyr Thr Ala Tyr Ala Pro Lys Phe
            50                  55                  60

Gln Gly Arg Val Thr Met Thr Arg Gln Arg Phe Thr Ser Thr Val Tyr
 65                  70                  75                  80

Met Glu Leu Ser Ser Leu Arg Ser Glu Asp Thr Ala Val Tyr Phe Cys
                 85                  90                  95

Ala Arg Val Lys Ser Ser Asp Ser Ile Asp Ala Phe Asp Ile Trp Gly
            100                 105                 110

Gln Gly Thr Met Val Ile Val Ser Ser
            115                 120

<210> SEQ ID NO 96
<211> LENGTH: 127
<212> TYPE: PRT
<213> ORGANISM: human

<400> SEQUENCE: 96

Gln Val Gln Val Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Cys Trp Val Arg Gln Ala Pro Gly Gln Gly Leu Glu Trp Met
         35                  40                  45

Gly Trp Ile Ser Thr Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Trp Pro Pro Arg Gly Ser Ser Gln Leu Asp Arg Gly Gln
            100                 105                 110

Tyr Phe Gln His Trp Gly Gln Gly Thr Leu Val Thr Val Ser Ser
            115                 120                 125

<210> SEQ ID NO 97
<211> LENGTH: 131
<212> TYPE: PRT
<213> ORGANISM: human

<400> SEQUENCE: 97

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Asn Tyr
             20                  25                  30

Ala Met Ser Trp Val Arg Gln Pro Pro Gly Lys Gly Leu Glu Trp Val
         35                  40                  45

Thr Ala Ile Ser Gly Asp Val Val Asp Thr Tyr Tyr Ala Asp Ser Val
     50                  55                  60

Gln Gly Arg Phe Ile Ile Ser Arg Asp Asn Ser Lys Asn Met Leu Tyr
 65                  70                  75                  80

Leu Glu Met Lys Ser Leu Arg Ala Glu Asp Thr Ala Val Tyr Tyr Cys
                 85                  90                  95

Ala Lys Asp Tyr Gly Ala Tyr Asp Ile Leu Thr Gly Lys Leu Leu Asp
            100                 105                 110

Tyr Tyr Gln Tyr Gly Met Asp Val Trp Gly Gln Gly Thr Thr Val Thr
            115                 120                 125

-continued

```
Val Ser Ser
    130

<210> SEQ ID NO 98
<211> LENGTH: 131
<212> TYPE: PRT
<213> ORGANISM: human

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Leu
            20                  25                  30

Met Tyr Phe Trp Gly Trp Ile Arg Gln Pro Pro Gly Lys Gly Leu Glu
        35                  40                  45

Trp Ile Gly Ser Ile Tyr Tyr Ser Gly Thr Ala Tyr Tyr Asn Pro Ser
    50                  55                  60

Leu Arg Ser Arg Ala Thr Ile Ser Val Asp Thr Ser Lys Asn Gln Leu
65                  70                  75                  80

Ser Leu Lys Leu Met Ser Val Thr Ala Ala Asp Thr Ala Val Tyr Tyr
                85                  90                  95

Cys Ala Arg Pro Ser Ser Phe Tyr Phe Asn Gly Arg Thr Ser Tyr Tyr
            100                 105                 110

Pro Gly Glu Thr Ala Phe Glu Ile Trp Gly Gln Gly Thr Thr Val Ala
        115                 120                 125

Val Ser Ser
    130

<210> SEQ ID NO 99
<211> LENGTH: 131
<212> TYPE: PRT
<213> ORGANISM: human

<400> SEQUENCE: 99

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Val
            20                  25                  30

Met Tyr Phe Trp Ala Trp Ile Arg Gln Ser Pro Gly Lys Gly Leu Glu
        35                  40                  45

Trp Ile Gly Ser Ile Tyr Tyr Ser Gly Thr Ala Tyr Tyr Asn Pro Ser
    50                  55                  60

Leu Arg Ser Arg Val Thr Met Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Pro Thr Ser Tyr Tyr Phe Ser Gly Thr Thr Ser Tyr Tyr
            100                 105                 110

Pro Gly Glu Ala Ala Phe Asp Ile Trp Gly Gln Gly Thr Thr Val Thr
        115                 120                 125

Val Ser Ser
    130

<210> SEQ ID NO 100
<211> LENGTH: 131
<212> TYPE: PRT
<213> ORGANISM: human
```

<400> SEQUENCE: 100

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Leu
            20                  25                  30

Met Tyr Phe Trp Gly Trp Ile Arg Gln Pro Pro Gly Lys Gly Leu Glu
        35                  40                  45

Trp Ile Gly Ser Ile Tyr Tyr Ser Gly Thr Thr Tyr Tyr Asn Pro Ser
50                  55                  60

Leu Arg Ser Arg Val Ser Ile Ser Val Asp Thr Ser Lys Asn Gln Leu
65                  70                  75                  80

Ser Leu Arg Leu Ile Ser Val Thr Ala Ala Asp Thr Ala Val Tyr Tyr
                85                  90                  95

Cys Ala Arg Pro Ala Ser Phe Tyr Phe Asn Gly Arg Thr Ser Tyr Tyr
            100                 105                 110

Pro Gly Glu Thr Ala Phe Glu Val Trp Gly Gln Gly Thr Val Ala
        115                 120                 125

Val Ser Ser
    130

<210> SEQ ID NO 101
<211> LENGTH: 131
<212> TYPE: PRT
<213> ORGANISM: human

<400> SEQUENCE: 101

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Val
            20                  25                  30

Met Tyr Phe Trp Gly Trp Ile Arg Gln Ser Pro Gly Lys Gly Leu Glu
        35                  40                  45

Trp Ile Gly Ser Ile Tyr Tyr Ser Gly Thr Ala Tyr Tyr Asn Pro Ser
50                  55                  60

Leu Arg Ser Arg Val Thr Met Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Pro Ser Ser Phe Tyr Phe Gly Gly Thr Thr Ser Tyr Tyr
            100                 105                 110

Pro Gly Glu Ala Ala Phe Asp Ile Trp Gly Gln Gly Thr Met Val Thr
        115                 120                 125

Val Ser Ser
    130

<210> SEQ ID NO 102
<211> LENGTH: 131
<212> TYPE: PRT
<213> ORGANISM: human

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Leu
            20                  25                  30

-continued

Met Tyr Phe Trp Gly Trp Ile Arg Gln Pro Pro Gly Lys Gly Leu Glu
            35                  40                  45

Trp Ile Gly Ser Ile Tyr Tyr Ser Gly Thr Ala Tyr Tyr Asn Pro Ser
        50                  55                  60

Leu Arg Ser Arg Val Thr Ile Ser Val Asp Thr Ser Lys Asn Gln Leu
65                  70                  75                  80

Ser Leu Lys Leu Met Ser Val Thr Ala Ala Asp Thr Ala Val Tyr Tyr
                85                  90                  95

Cys Ala Arg Pro Ser Ser Phe Tyr Phe Asn Gly Arg Thr Ser Tyr Tyr
            100                 105                 110

Pro Gly Glu Thr Ala Phe Glu Ile Trp Gly Gln Gly Thr Thr Val Ala
            115                 120                 125

Val Ser Ser
    130

<210> SEQ ID NO 103
<211> LENGTH: 124
<212> TYPE: PRT
<213> ORGANISM: human

<400> SEQUENCE: 103

Gln Met Gln Leu Val Gln Ser Gly Gly Val Leu Ala Glu Val Gly Gly
1               5                   10                  15

Ser Leu Arg Leu Ser Cys Ala Val Ser Gly Leu Thr Phe Asn Asn Ala
            20                  25                  30

Trp Met Asn Trp Val Arg Gln Ala Pro Gly Arg Gly Leu Glu Cys Val
        35                  40                  45

Gly Arg Ile Lys Ser Lys Ile Asp Gly Gly Thr Thr Asp Tyr Ala Thr
    50                  55                  60

Pro Val Lys Gly Arg Phe Thr Ile Ser Arg Asp Asp Ser Lys Asn Met
65                  70                  75                  80

Val Tyr Leu Gln Met Asn Ser Leu Arg Ile Glu Asp Thr Ala Val Tyr
                85                  90                  95

Tyr Cys Thr Thr Arg Pro Asn Pro Trp Gln Ser Pro Ala Pro Trp Asp
            100                 105                 110

Phe Trp Gly Gln Gly Thr Leu Val Thr Val Ser Ser
        115                 120

<210> SEQ ID NO 104
<211> LENGTH: 124
<212> TYPE: PRT
<213> ORGANISM: human

<400> SEQUENCE: 104

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Arg Tyr
            20                  25                  30

Thr Leu Ser Trp Val Arg Gln Ala Pro Gly Lys Gly Leu Glu Trp Val
        35                  40                  45

Ser Tyr Ile Ser Thr Asp Gly Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Ile Ser Leu Arg Asp Glu Asp Thr Ala Val Tyr Tyr Cys
                85                  90                  95

```
Ala Arg Val Phe Phe Gly Gly Asn Phe Arg Ala His Trp Tyr Phe Asp
            100                 105                 110

Leu Trp Gly Arg Gly Thr Leu Val Thr Val Ser Ser
        115                 120

<210> SEQ ID NO 105
<211> LENGTH: 124
<212> TYPE: PRT
<213> ORGANISM: human

<400> SEQUENCE: 105

Gln Val Gln Leu Val Glu Ser Gly Gly Leu Val Arg Pro Gly Gly
1               5                   10                  15

Ser Leu Arg Leu Ser Cys Ala Ala Ser Gly Phe Thr Phe Ser Arg Tyr
            20                  25                  30

Thr Leu Ser Trp Val Arg Gln Ala Pro Gly Lys Gly Leu Glu Trp Val
            35                  40                  45

Ser Tyr Ile Ser Thr Asp Gly Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Ile Ser Leu Arg Asp Glu Asp Thr Ala Val Tyr Tyr Cys
                85                  90                  95

Ala Arg Val Phe Phe Gly Gly Asn Phe Arg Ala His Trp Tyr Phe Asp
            100                 105                 110

Leu Trp Gly Arg Gly Thr Leu Val Thr Val Ser Ser
        115                 120

<210> SEQ ID NO 106
<211> LENGTH: 118
<212> TYPE: PRT
<213> ORGANISM: human

<400> SEQUENCE: 106

Glu Val Gln Leu Val Gln Ser Gly Ala Glu Val Gly Lys Pro Gly Ala
1               5                   10                  15

Ser Val Lys Val Ser Cys Gly Ala Ser Gly Tyr Ser Phe Thr Ala Tyr
            20                  25                  30

Tyr Met His Trp Val Arg Gln Ala Pro Gly Gln Gly Leu Gln Trp Met
            35                  40                  45

Gly Trp Ile Thr Pro Asp Asn Gly Arg Thr Asn Tyr Ala Gln Gln Phe
    50                  55                  60

Gln Arg Arg Ile Thr Leu Thr Ser Asp Thr Ser Ile Asn Thr Val Tyr
65                  70                  75                  80

Leu Glu Met Lys Ser Leu Lys Ser Asp Asp Thr Ala Val Tyr Tyr Cys
                85                  90                  95

Val Arg Ser Gly Trp Ser Gln Pro Leu Asp Tyr Trp Gly Gln Gly Thr
            100                 105                 110

Leu Val Thr Val Ser Ser
        115

<210> SEQ ID NO 107
<211> LENGTH: 120
<212> TYPE: PRT
<213> ORGANISM: human

<400> SEQUENCE: 107

Gln Val Gln Leu Val Glu Ser Gly Gly Val Val Gln Pro Gly Gly
1               5                   10                  15
```

```
1               5                   10                  15
Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
            35                  40                  45

Ser Leu Ile Ser Trp Asp Ala Ile Ser Thr Tyr Tyr Ala Asp Ser Val
            50                  55                  60

Lys Gly Arg Phe Thr Thr Ser Arg Asp Asn Lys Asn Phe Leu Tyr
 65                  70                  75                  80

Leu Gln Met Asp Ser Leu Thr Pro Glu Asp Thr Ala Leu Tyr Tyr Cys
            85                  90                  95

Gly Lys Asp Gln Gly Gly Arg Phe Arg Leu Val Asp Tyr Trp Gly Gln
            100                 105                 110

Gly Thr Leu Val Thr Val Ser Ser
            115                 120

<210> SEQ ID NO 108
<211> LENGTH: 107
<212> TYPE: PRT
<213> ORGANISM: human

<400> SEQUENCE: 108

Glu Ile Val Met Thr Gln Ser Pro Ala Ala Leu Ser Val Ser Pro Gly
 1               5                   10                  15

Glu Arg Ala Thr Leu Ser Cys Arg Ala Ser Gln Ser Ile Ser Ser Ser
            20                  25                  30

Leu Ala Trp Tyr Gln Gln Lys Pro Gly Gln Ala Pro Arg Leu Leu Ile
            35                  40                  45

Tyr Ala Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Val Val Tyr Tyr Cys Gln Gln Tyr Asn Asn Trp Pro Ile
            85                  90                  95

Thr Phe Gly Gln Gly Thr Arg Leu Glu Ile Arg
            100                 105

<210> SEQ ID NO 109
<211> LENGTH: 107
<212> TYPE: PRT
<213> ORGANISM: human

<400> SEQUENCE: 109

Glu Ile Val Met Thr Gln Ser Pro Ala Thr Leu Ser Val Ser Pro Gly
 1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Ile
            85                  90                  95

Thr Phe Gly Gln Gly Thr Arg Leu Glu Ile Lys
            100                 105
```

-continued

<210> SEQ ID NO 110
<211> LENGTH: 107
<212> TYPE: PRT
<213> ORGANISM: human

<400> SEQUENCE: 110

Glu Ile Val Met Thr Gln Phe Pro Ala Thr Leu Ser Ala Ser Pro Gly
1               5                   10                  15

Glu Arg Ala Thr Leu Ser Cys Arg Ala Ser Gln Thr Ile Asn Asn Asp
            20                  25                  30

Val Ala Trp Tyr Gln Gln Arg Pro Gly Gln Gly Pro Arg Leu Leu Ile
        35                  40                  45

Phe Gly Thr Ser Thr Arg Ala Pro Gly Ile Pro Ala Arg Phe Ser Gly
    50                  55                  60

Ser Gly Ser Gly Thr Asp Tyr Thr Leu Ser Ile Ser Ser Leu Gln Ser
65                  70                  75                  80

Glu Asp Phe Ala Val Tyr Tyr Cys Gln Gln Tyr Thr Tyr Trp Pro Gly
                85                  90                  95

Thr Phe Gly Pro Gly Thr Arg Val Asp Phe Arg
            100                 105

<210> SEQ ID NO 111
<211> LENGTH: 107
<212> TYPE: PRT
<213> ORGANISM: human

<400> SEQUENCE: 111

Glu Ile Val Met Thr Gln Ser Pro Ala Thr Leu Ser Val Ser Pro Gly
1               5                   10                  15

Glu Arg Ala Ser Leu Ser Cys Arg Ala Ser Gln Asn Ile Arg Ser Asn
            20                  25                  30

Leu Ala Trp Tyr Gln Gln Ser Pro Gly Gln Ala Pro Arg Leu Leu Ile
        35                  40                  45

Tyr Gly Ala Ser Thr Arg Ala Ser Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Leu
                85                  90                  95

Thr Phe Gly Gly Gly Thr Lys Val Glu Ile Arg
            100                 105

<210> SEQ ID NO 112
<211> LENGTH: 107
<212> TYPE: PRT
<213> ORGANISM: human

<400> SEQUENCE: 112

Glu Ile Val Met Thr Gln Ser Pro Ala Thr Leu Ser Val Ser Pro Gly
1               5                   10                  15

Glu Thr Thr Thr Leu Ser Cys Arg Ala Ser His Ser Val Thr Ser Asp
            20                  25                  30

Leu Ala Trp Tyr Gln Gln Lys Pro Gly Gln Ala Pro Arg Leu Leu Ile
        35                  40                  45

Tyr Ala Thr Ser Thr Arg Ala Ala Gly Val Pro Ala Arg Phe Ser Gly
    50                  55                  60

-continued

```
Ser Gly Ser Gly Thr Glu Phe Thr Leu Thr Ile Ser Ser Leu Gln Ser
 65                  70                  75                  80

Glu Asp Phe Ala Val Tyr His Cys Gln Gln Tyr Asn Lys Trp Pro Val
                 85                  90                  95

Thr Phe Gly Gly Gly Thr Lys Val Asp Leu Arg
            100                 105

<210> SEQ ID NO 113
<211> LENGTH: 107
<212> TYPE: PRT
<213> ORGANISM: human

<400> SEQUENCE: 113

Glu Ile Val Met Thr Gln Ser Pro Ala Thr Leu Ser Val Ser Pro Gly
  1               5                  10                  15

Glu Arg Ala Thr Leu Ser Cys Arg Ala Gly Gln Ser Val Ser Ser Asn
                 20                  25                  30

Leu Ala Trp Tyr Gln Gln Lys Pro Gly Gln Ala Pro Arg Leu Leu Ile
             35                  40                  45

His Ala Ala Ser Thr Arg Ala Thr Gly Ala Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Tyr Asp Lys Trp Pro Pro
                 85                  90                  95

Thr Phe Gly Gln Gly Thr Asn Leu Glu Ile Lys
            100                 105

<210> SEQ ID NO 114
<211> LENGTH: 107
<212> TYPE: PRT
<213> ORGANISM: human

<400> SEQUENCE: 114

Glu Ile Val Met Thr Gln Ser Pro Ala Thr Leu Ser Val Ser Pro Gly
  1               5                  10                  15

Glu Arg Ala Thr Leu Ser Cys Trp Ala Ser Gln Ser Val Ser Ser Asp
                 20                  25                  30

Leu Ala Trp Tyr Gln Gln Lys Pro Gly Gln Ala Pro Arg Leu Leu Ile
             35                  40                  45

His Ala Ala Ser Thr Arg Ala Thr Gly Ala Pro Ala Arg Phe Ser Gly
         50                  55                  60

Ser Gly Ser Gly Thr Asp Phe Thr Leu Thr Ile Ser Ser Leu Gln Ser
 65                  70                  75                  80

Glu Asp Phe Ala Val Tyr Phe Cys Gln Gln Tyr Asn Lys Trp Pro Pro
                 85                  90                  95

Thr Phe Gly Gln Gly Thr Asn Leu Glu Ile Lys
            100                 105

<210> SEQ ID NO 115
<211> LENGTH: 107
<212> TYPE: PRT
<213> ORGANISM: human

<400> SEQUENCE: 115

Glu Ile Val Met Thr Gln Ser Pro Ala Thr Leu Ser Val Ser Pro Gly
  1               5                  10                  15
```

```
Glu Arg Ala Thr Leu Ser Cys Arg Ala Ser Gln Ser Ile Ser Gly Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Ala Phe Gly Gln Gly Thr Lys Val Glu Ile Lys
            100                 105
```

<210> SEQ ID NO 116
<211> LENGTH: 107
<212> TYPE: PRT
<213> ORGANISM: human

<400> SEQUENCE: 116

```
Glu Ile Val Met Thr Gln Ser Leu Ala Thr Leu Ser Ala Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Gly Gly
    50                  55                  60

Ser Glu Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Asn Trp Pro Pro
                85                  90                  95

Thr Phe Gly Gln Gly Thr Lys Val Glu Ile Lys
            100                 105
```

<210> SEQ ID NO 117
<211> LENGTH: 107
<212> TYPE: PRT
<213> ORGANISM: human

<400> SEQUENCE: 117

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Pro Gly Thr Lys Val Asp Ile Lys
            100                 105
```

<210> SEQ ID NO 118
<211> LENGTH: 107

```
<212> TYPE: PRT
<213> ORGANISM: human

<400> SEQUENCE: 118

Glu Ile Val Met Thr Gln Ser Pro Ala Thr Leu Ser Val Ser Pro Gly
1               5                   10                  15

Glu Arg Val Thr Leu Ser Cys Gly Ala Ser Gln Ser Val Ser Ser Asn
            20                  25                  30

Leu Ala Trp Tyr Gln Gln Lys Pro Gly Gln Ala Pro Arg Leu Leu Met
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Ala Trp Pro Leu
                85                  90                  95

Thr Phe Gly Gly Gly Thr Lys Val Glu Ile Lys
            100                 105

<210> SEQ ID NO 119
<211> LENGTH: 107
<212> TYPE: PRT
<213> ORGANISM: human

<400> SEQUENCE: 119

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Pro Gly Thr Lys Val Asp Ile Lys
            100                 105

<210> SEQ ID NO 120
<211> LENGTH: 107
<212> TYPE: PRT
<213> ORGANISM: human

<400> SEQUENCE: 120

Glu Ile Val Met Thr Gln Ser Pro Ala Thr Leu Ser Val Ser Pro Gly
1               5                   10                  15

Asp Arg Ala Thr Leu Ser Cys Arg Ala Ser Gln Ser Val Ser Thr Asn
            20                  25                  30

Val Ala Trp Tyr Gln Gln Lys Pro Gly Gln Ala Pro Arg Leu Leu Ile
        35                  40                  45

Tyr Gly Ser Ser Thr Arg Ala Thr Gly Ile Pro Ala Thr Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro His
```

```
                    85                  90                  95

Ala Phe Gly Gln Gly Thr Arg Leu Glu Ile Lys
            100                 105

<210> SEQ ID NO 121
<211> LENGTH: 107
<212> TYPE: PRT
<213> ORGANISM: human

<400> SEQUENCE: 121

Glu Ile Val Met Thr Gln Ser Pro Ala Leu Ser Val Ser Pro Gly
 1               5                  10                  15

Glu Arg Ala Thr Leu Ser Cys Arg Ala Ser Gln Ser Ile Ser Ser
                20                  25                  30

Leu Ala Trp Tyr Gln Gln Lys Pro Gly Gln Ala Pro Arg Leu Leu Ile
            35                  40                  45

Tyr Ala Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Arg
            100                 105

<210> SEQ ID NO 122
<211> LENGTH: 107
<212> TYPE: PRT
<213> ORGANISM: human

<400> SEQUENCE: 122

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Phe Gly Gln Gly Thr Lys Val Glu Ile Lys
            100                 105

<210> SEQ ID NO 123
<211> LENGTH: 107
<212> TYPE: PRT
<213> ORGANISM: human

<400> SEQUENCE: 123

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45
```

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Asn
                85                  90                  95

Thr Phe Gly Pro Gly Thr Lys Val Asp Ile Lys
            100                 105

<210> SEQ ID NO 124
<211> LENGTH: 107
<212> TYPE: PRT
<213> ORGANISM: human

<400> SEQUENCE: 124

Glu Ile Val Met Thr Gln Ser Pro Ala Thr Leu Ser Val Ser Pro Glu
1               5                   10                  15

Gln Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Met
            35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Met Ser Gly Leu Gln Ser
65                  70                  75                  80

Glu Asp Phe Ala Val Tyr Tyr Cys Gln Gln Tyr Asp Asn Trp Pro Ser
                85                  90                  95

Thr Phe Gly Gln Gly Thr Arg Leu Glu Ile Lys
            100                 105

<210> SEQ ID NO 125
<211> LENGTH: 107
<212> TYPE: PRT
<213> ORGANISM: human

<400> SEQUENCE: 125

Glu Ile Val Met Thr Gln Ser Pro Ala Ala Leu Ser Val Ser Pro Gly
1               5                   10                  15

Glu Arg Ala Thr Leu Ser Cys Arg Ala Ser Gln Ser Ile Ser Ser Ser
                20                  25                  30

Leu Ala Trp Tyr Gln Gln Lys Pro Gly Gln Ala Pro Arg Leu Leu Ile
            35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Arg
            100                 105

<210> SEQ ID NO 126
<211> LENGTH: 107
<212> TYPE: PRT
<213> ORGANISM: human

<400> SEQUENCE: 126
```

-continued

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Gly
                85                  90                  95

Thr Phe Gly Gln Gly Thr Lys Val Glu Ile Lys
            100                 105

<210> SEQ ID NO 127
<211> LENGTH: 107
<212> TYPE: PRT
<213> ORGANISM: human

<400> SEQUENCE: 127

Glu Ile Val Met Thr Gln Ser Pro Val Ser Leu Pro Leu Ser Pro Gly
1               5                   10                  15

Glu Arg Val Thr Leu Ser Cys Arg Ala Ser Gln Ser Val Arg Gly Asp
            20                  25                  30

Leu Ala Trp Tyr Gln Gln Lys Pro Gly Gln Ala Pro Arg Leu Leu Ile
        35                  40                  45

Phe Asn Ala Ser Thr Arg Ala Thr Gly Ile Ser Asp Arg Phe Ser Gly
50                  55                  60

Ser Gly Ser Gly Thr Glu Phe Thr Leu Thr Ile Ala Ser Leu Gln Pro
65                  70                  75                  80

Asp Asp Phe Ala Val Tyr Ser Cys Gln Gln Tyr Asn Asp Trp Pro Leu
                85                  90                  95

Thr Phe Gly Gly Gly Thr Lys Val Glu Ile Arg
            100                 105

<210> SEQ ID NO 128
<211> LENGTH: 107
<212> TYPE: PRT
<213> ORGANISM: human

<400> SEQUENCE: 128

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

His Ala Ala Ser Thr Arg Ala Thr Gly Ala Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Glu Trp Pro Pro
                85                  90                  95

Thr Phe Gly Gln Gly Thr Asn Leu Glu Ile Lys
            100                 105
```

<210> SEQ ID NO 129
<211> LENGTH: 107
<212> TYPE: PRT
<213> ORGANISM: human

<400> SEQUENCE: 129

Asp Ile Val Met Thr Gln Ser Pro Ala Thr Leu Ser Val Ser Pro Glu
1               5                   10                  15

Ala Arg Ala Thr Leu Ser Cys Arg Ala Ser Gln Ser Val Ser Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asp Asn Trp Pro Ile
                85                  90                  95

Thr Phe Gly Gln Gly Thr Arg Leu Glu Ile Lys
            100                 105

<210> SEQ ID NO 130
<211> LENGTH: 107
<212> TYPE: PRT
<213> ORGANISM: human

<400> SEQUENCE: 130

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Ser
            20                  25                  30

Leu Ala Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Tyr Ser Tyr Gly
                85                  90                  95

Pro Phe Gly Leu Gly Thr Lys Val Glu Ile Lys
            100                 105

<210> SEQ ID NO 131
<211> LENGTH: 104
<212> TYPE: PRT
<213> ORGANISM: human

<400> SEQUENCE: 131

Asp Ile Gln Leu Thr Gln Ser Pro Ser Thr Leu Ser Ala Ser Val Gly
1               5                   10                  15

Asp Arg Val Thr Ile Thr Cys Arg Ala Ser Arg Asp Ile Lys Thr Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Asp Asp Ser Ala Thr Tyr Tyr Cys Gln Gln Tyr Asn Tyr Tyr Phe Gly
                    85                  90                  95

Gln Gly Thr Lys Leu Glu Ile Lys
            100

<210> SEQ ID NO 132
<211> LENGTH: 108
<212> TYPE: PRT
<213> ORGANISM: human

<400> SEQUENCE: 132

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Trp Thr Phe Gly Gln Gly Thr Lys Val Glu Ile Lys
            100                 105

<210> SEQ ID NO 133
<211> LENGTH: 109
<212> TYPE: PRT
<213> ORGANISM: human

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Arg Tyr Thr Phe Gly Gln Gly Thr Lys Leu Glu Ile Lys
            100                 105

<210> SEQ ID NO 134
<211> LENGTH: 109
<212> TYPE: PRT
<213> ORGANISM: human

<400> SEQUENCE: 134

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Lys
            20                  25                  30
```

Phe Leu Ala Trp Tyr Gln Gln Lys Arg Gly Gln Pro Arg Leu Leu
            35                  40                  45

Ile Tyr Gly Ala Ser Asn Thr Ala Thr Gly Ile Pro Asp Arg Phe Ser
     50                  55                  60

Gly Ser Gly Ser Gly Thr Glu Phe Thr Leu Thr Ile Ser Arg Leu Glu
 65                  70                  75                  80

Pro Glu Asp Phe Ala Leu Tyr Tyr Cys Gln His Tyr Gly Ser Ser Pro
                 85                  90                  95

Gly Val Thr Phe Gly Gln Gly Thr Arg Leu Asp Val Lys
                100                 105

<210> SEQ ID NO 135
<211> LENGTH: 109
<212> TYPE: PRT
<213> ORGANISM: human

<400> SEQUENCE: 135

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Ile Thr Phe Gly Gln Gly Thr Arg Leu Glu Ile Lys
                100                 105

<210> SEQ ID NO 136
<211> LENGTH: 106
<212> TYPE: PRT
<213> ORGANISM: human

<400> SEQUENCE: 136

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ile Ile Ser Tyr Leu
                20                  25                  30

Ala Trp Tyr Gln Gln Lys Pro Gly Gln Ala Pro Arg Leu Leu Ile Tyr
            35                  40                  45

Ser Thr Ser Thr Arg Ala Thr Gly Ile Pro Asp Arg Phe Ser Gly Ser
     50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Tyr Gly Gly Ser Pro Phe Thr
                 85                  90                  95

Phe Gly Pro Gly Thr Lys Val Glu Phe Lys
                100                 105

<210> SEQ ID NO 137
<211> LENGTH: 108
<212> TYPE: PRT
<213> ORGANISM: human

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Gly Asn Asn
            20                  25                  30

Asn Leu Ala Trp Tyr Gln Gln Arg Leu Gly Gln Ala Pro Arg Leu Leu
        35                  40                  45

Ile Tyr Gly Ala Ser Ser Arg Ala Thr Ala Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Pro Pro
                85                  90                  95

Ile Thr Phe Gly Gly Gly Thr Lys Val Glu Ile Lys
            100                 105

<210> SEQ ID NO 138
<211> LENGTH: 113
<212> TYPE: PRT
<213> ORGANISM: human

<400> SEQUENCE: 138

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Asn Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Ala Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 139
<211> LENGTH: 107
<212> TYPE: PRT
<213> ORGANISM: human

<400> SEQUENCE: 139

Glu Ile Val Met Thr Gln Ser Pro Ala Ser Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Asn Thr Arg Ala Thr Asp Phe Pro Ala Arg Phe Ser Gly
    50                  55                  60

Ser Gly Ser Gly Thr Gln Phe Thr Leu Thr Ile Ser Gly Leu Gln Ser
65                  70                  75                  80

Glu Asp Ser Ala Val Tyr Tyr Cys Gln Gln Tyr His Asp Trp Pro Gln

```
                    85                  90                  95
Thr Phe Gly Gln Gly Thr Lys Val Glu Phe Lys
            100                 105

<210> SEQ ID NO 140
<211> LENGTH: 113
<212> TYPE: PRT
<213> ORGANISM: human

<400> SEQUENCE: 140

Asp Ile Val Met Thr Gln Ser Pro Asp Ser Leu Ser Val Ser Leu Gly
1               5                   10                  15

Glu Arg Ala Thr Leu Asn Cys Lys Ser Ser Gln Asn Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 141
<211> LENGTH: 107
<212> TYPE: PRT
<213> ORGANISM: human

<400> SEQUENCE: 141

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Asn
                85                  90                  95

Thr Phe Gly Gly Gly Thr Lys Val Glu Ile Lys
            100                 105

<210> SEQ ID NO 142
<211> LENGTH: 107
<212> TYPE: PRT
<213> ORGANISM: human

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65              70                  75                      80

Glu Asp Phe Ala Val Tyr Tyr Cys Gln Gln Arg Ser Asn Trp Pro Pro
                 85                  90                  95

Thr Phe Gly Gly Gly Thr Lys Val Glu Ile Lys
            100                 105
```

<210> SEQ ID NO 143
<211> LENGTH: 107
<212> TYPE: PRT
<213> ORGANISM: human

<400> SEQUENCE: 143

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65              70                  75                      80

Glu Asp Phe Ala Val Tyr Tyr Cys Gln Gln Arg Ser Asn Trp Pro Leu
                 85                  90                  95

Thr Phe Gly Gln Gly Thr Arg Leu Glu Ile Lys
            100                 105
```

<210> SEQ ID NO 144
<211> LENGTH: 113
<212> TYPE: PRT
<213> ORGANISM: human

<400> SEQUENCE: 144

```
Asp Ile Met Met Thr Gln Ser Pro Glu Ser Leu Ala Val Ser Leu Gly
 1               5                  10                  15

Glu Arg Ala Thr Ile Tyr Cys Lys Ser Ser Gln Thr Ile Leu Ser Ser
            20                  25                  30

Arg Asn Asn Gln Lys Tyr Leu Ala Trp Tyr Gln Gln Lys Ala Gly His
            35                  40                  45

Pro Pro Lys Leu Leu Ile Tyr Asx Ala Ser Ser Arg Glu Ser Gly Val
 50                  55                  60

Pro Ser Arg Phe Ser Gly Ser Gly Ser Gly Thr Glu Phe Thr Leu Thr
 65              70                  75                      80

Ile Ser Ser Leu Gln Ala Glu Asp Val Ala Val Tyr Tyr Cys Gln Gln
                 85                  90                  95

Tyr Tyr Thr Thr Pro Ser Thr Phe Gly Gly Gly Thr Lys Val Glu Ile
            100                 105                 110

Lys
```

<210> SEQ ID NO 145
<211> LENGTH: 107
<212> TYPE: PRT

<213> ORGANISM: human

<400> SEQUENCE: 145

Asp Ile Gln Leu Thr Gln Ser Pro Ser Leu Ser Ala Ser Val Gly
1               5                   10                  15

Asp Arg Val Ser Ile Thr Cys Arg Ala Ser Gln Asp Ile Ser Asn Tyr
            20                  25                  30

Leu Val Trp Phe Gln Gln Lys Pro Gly Lys Ala Pro Lys Ser Leu Ile
        35                  40                  45

Tyr Ala Ala Ser Ser Leu Gln Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Lys Asn Tyr Pro Leu
                85                  90                  95

Thr Phe Gly Gly Gly Thr Lys Val Glu Ile Lys
            100                 105

<210> SEQ ID NO 146
<211> LENGTH: 125
<212> TYPE: PRT
<213> ORGANISM: human

<400> SEQUENCE: 146

Leu Glu Glu Val Gln Leu Leu Glu Ser Gly Gly Gly Leu Val His Pro
1               5                   10                  15

Gly Gly Ser Leu Arg Leu Ser Cys Ala Ala Ser Gly Phe Arg Phe Gly
            20                  25                  30

Ser Tyr Ala Met Ser Trp Val Arg Gln Ala Pro Gly Lys Gly Leu Glu
        35                  40                  45

Trp Val Ser Ser Ile Ser Gly Ser Gly Asp Thr Ile Tyr Tyr Ala Asp
50                  55                  60

Ser Val Arg Gly Arg Phe Thr Ile Ser Lys Asp Ser Arg Asn Thr
65                  70                  75                  80

Leu Phe Leu Gln Leu Asn Ser Leu Arg Val Asp Asp Thr Ala Val Tyr
                85                  90                  95

Tyr Cys Ala Lys Gly Ser Ile Phe Gly Thr Ala Lys Val Tyr Gly Val
            100                 105                 110

Asp Tyr Trp Gly Gln Gly Ala Leu Val Thr Val Ser Ser
        115                 120                 125

<210> SEQ ID NO 147
<211> LENGTH: 125
<212> TYPE: PRT
<213> ORGANISM: human

<400> SEQUENCE: 147

Leu Glu Glu Val Gln Leu Leu Glu Ser Gly Gly Gly Leu Val His Pro
1               5                   10                  15

Gly Gly Ser Leu Arg Leu Ser Cys Ala Ala Ser Gly Phe Arg Phe Gly
            20                  25                  30

Ser Tyr Ala Met Ser Trp Val Arg Gln Ala Pro Gly Lys Gly Leu Glu
        35                  40                  45

Trp Val Ser Ser Ile Ser Gly Ser Gly Asp Thr Ile Tyr Tyr Ala Asp
50                  55                  60

Ser Val Arg Gly Arg Phe Thr Ile Ser Lys Asp Ser Arg Asn Thr
65                  70                  75                  80

```
Leu Phe Leu Gln Leu Asn Ser Leu Arg Val Asp Asp Thr Ala Val Tyr
                85                  90                  95

Tyr Cys Ala Lys Gly Ser Ile Phe Gly Thr Ala Lys Val Tyr Gly Val
            100                 105                 110

Asp Tyr Trp Gly Gln Gly Thr Leu Val Thr Val Ser Ser
            115                 120                 125
```

<210> SEQ ID NO 148
<211> LENGTH: 125
<212> TYPE: PRT
<213> ORGANISM: human

<400> SEQUENCE: 148

```
Leu Glu Glu Val Gln Leu Leu Glu Ser Gly Gly Gly Leu Val His Pro
1               5                   10                  15

Gly Gly Ser Leu Arg Leu Ser Cys Ala Ala Ser Gly Phe Arg Phe Gly
            20                  25                  30

Ser Tyr Ala Met Ser Trp Val Arg Gln Ala Pro Gly Lys Gly Leu Glu
            35                  40                  45

Trp Val Ser Ser Ile Ser Gly Ser Gly Asp Thr Ile Tyr Tyr Ala Asp
            50                  55                  60

Ser Val Arg Gly Arg Phe Thr Ile Ser Lys Asp Ser Ser Arg Asn Thr
65                  70                  75                  80

Leu Phe Leu Gln Leu Asn Ser Leu Arg Val Asp Asp Thr Ala Val Tyr
                85                  90                  95

Tyr Cys Ala Lys Gly Ser Ile Phe Gly Thr Ala Lys Val Tyr Gly Val
            100                 105                 110

Asp Tyr Trp Gly Gln Gly Thr Leu Val Thr Val Ser Ser
            115                 120                 125
```

<210> SEQ ID NO 149
<211> LENGTH: 125
<212> TYPE: PRT
<213> ORGANISM: human

<400> SEQUENCE: 149

```
Leu Glu Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Arg Phe Ser
            20                  25                  30

Ser Tyr Gly Met Ser Trp Val Arg Gln Ala Pro Gly Lys Gly Leu Glu
            35                  40                  45

Trp Val Ser Gly Ile Ser Gly Ser Gly Ser Thr His Tyr Ala Asp
            50                  55                  60

Ser Val Lys Gly Arg Phe Ile Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Gly Tyr Tyr Gly Ser Gly Leu Phe Tyr Gly Met
            100                 105                 110

Asp Val Trp Gly Gln Gly Thr Thr Val Thr Val Ser Ser
            115                 120                 125
```

<210> SEQ ID NO 150
<211> LENGTH: 125
<212> TYPE: PRT
<213> ORGANISM: human

-continued

<400> SEQUENCE: 150

Leu Glu Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Arg Phe Thr
            20                  25                  30

Ser Tyr Gly Met Ser Trp Val Arg Gln Ala Pro Gly Lys Gly Leu Glu
        35                  40                  45

Trp Val Ser Gly Ile Ser Gly Asn Gly Gly Arg Ile Tyr Tyr Ala Asp
    50                  55                  60

Ser Val Lys Gly Arg Phe Ile Ile Ser Arg Asp Asn Ser Lys Asn Thr
65                  70                  75                  80

Leu Tyr Leu Gln Met Asp Ser Leu Arg Ala Asp Asp Thr Ala Val Tyr
                85                  90                  95

Tyr Cys Ala Lys Asp Gly Tyr Tyr Gly Ser Gly Val Phe Tyr Gly Met
            100                 105                 110

Asp Val Trp Gly Gln Gly Thr Thr Val Thr Val Ser Ser
        115                 120                 125

<210> SEQ ID NO 151
<211> LENGTH: 125
<212> TYPE: PRT
<213> ORGANISM: human

<400> SEQUENCE: 151

Leu Glu Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Arg Phe Thr
            20                  25                  30

Ser Tyr Gly Met Ser Trp Val Arg Gln Ala Pro Gly Lys Gly Leu Glu
        35                  40                  45

Trp Val Ser Gly Ile Ser Gly Asn Gly Gly Arg Ile Tyr Tyr Ala Asp
    50                  55                  60

Ser Val Lys Gly Arg Phe Ile Ile Ser Arg Asp Asn Ser Lys Asn Thr
65                  70                  75                  80

Leu Tyr Leu Gln Met Asp Ser Leu Arg Ala Asp Asp Thr Ala Val Tyr
                85                  90                  95

Tyr Cys Ala Lys Asp Gly Tyr Tyr Gly Ser Gly Val Phe Tyr Gly Met
            100                 105                 110

Asp Val Trp Gly Gln Gly Thr Thr Val Thr Val Ser Ser
        115                 120                 125

<210> SEQ ID NO 152
<211> LENGTH: 125
<212> TYPE: PRT
<213> ORGANISM: human

<400> SEQUENCE: 152

Leu Glu Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Arg Phe Ser
            20                  25                  30

Ser Tyr Gly Met Ser Trp Val Arg Gln Val Pro Gly Lys Gly Leu Glu
        35                  40                  45

Trp Val Ala Gly Ile Thr Gly Asn Ser Gly Lys Ile Tyr Tyr Ala Asp
    50                  55                  60

```
Ser Val Lys Gly Arg Phe Ile Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Gly Tyr Tyr Gly Ser Gly Ser Phe Tyr Gly Ile
            100                 105                 110

Asp Val Trp Gly Gln Gly Thr Thr Val Thr Val Ser Ser
        115                 120                 125

<210> SEQ ID NO 153
<211> LENGTH: 125
<212> TYPE: PRT
<213> ORGANISM: human

<400> SEQUENCE: 153

Leu Glu Glu Val Gln Leu Leu Glu Ser Gly Gly Gly Leu Val Gln Pro
 1               5                  10                  15

Gly Gly Ser Leu Arg Leu Ser Cys Ala Ala Ser Gly Phe Arg Phe Ser
            20                  25                  30

Ser Tyr Gly Met Ser Trp Val Arg Gln Ala Pro Gly Lys Gly Leu Glu
        35                  40                  45

Trp Val Ser Gly Leu Ser Gly Ser Ser Gly Arg Ile Tyr Tyr Ala Asp
    50                  55                  60

Ser Val Lys Gly Arg Phe Ile Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Gly Tyr Tyr Gly Ser Gly Leu Leu Tyr Gly Ile
            100                 105                 110

Asp Val Trp Gly Gln Gly Thr Thr Val Ala Val Ser Ser
        115                 120                 125

<210> SEQ ID NO 154
<211> LENGTH: 125
<212> TYPE: PRT
<213> ORGANISM: human

<400> SEQUENCE: 154

Leu Glu Gln Val Gln Leu Val Glu Ser Gly Gly Gly Val Val Gln Pro
 1               5                  10                  15

Gly Gly Ser Gln Arg Leu Ser Cys Ala Ala Ser Gly Phe Thr Phe Arg
            20                  25                  30

Asn Tyr Gly Met His Trp Val Arg Gln Ala Pro Gly Lys Gly Leu Glu
        35                  40                  45

Trp Val Ala Tyr Ile Leu Tyr Asp Gly Ser Lys Lys Tyr Tyr Val Asp
    50                  55                  60

Ser Val Lys Gly Arg Phe Thr Val Ser Arg Asp Asn Ser Gln Asn Thr
 65                  70                  75                  80

Leu Tyr Leu Gln Met Asn Ser Leu Arg Pro Glu Asp Thr Ala Val Tyr
                 85                  90                  95

Tyr Cys Val Lys Asp Gly Leu Leu Ala Gly Tyr Glu Gly Gly Phe
            100                 105                 110

Asp Tyr Trp Gly Gln Gly Thr Leu Val Thr Val Ser Ser
        115                 120                 125

<210> SEQ ID NO 155
<211> LENGTH: 125
```

```
<212> TYPE: PRT
<213> ORGANISM: human

<400> SEQUENCE: 155

Leu Glu Gln Val Gln Leu Val Glu Ser Gly Gly Gly Val Val Gln Pro
1               5                   10                  15

Gly Arg Ser Leu Arg Leu Ser Cys Ala Ala Ser Gly Val Arg Phe Ser
            20                  25                  30

Ser Tyr Gly Met His Trp Val Arg Gln Ala Pro Gly Lys Gly Leu Glu
        35                  40                  45

Trp Val Ala Ser Ile Ser Ser Asp Ala Thr Lys Lys Asn Tyr Ala Asp
    50                  55                  60

Ser Val Lys Gly Arg Phe Thr Ile Ser Arg Asp Asn Ser Lys Asn Thr
65                  70                  75                  80

Leu His Leu Gln Met Val Thr Leu Arg Pro Glu Asp Thr Ala Val Tyr
                85                  90                  95

Tyr Cys Ala Lys Thr Asp Ile Leu Gly Pro Ala Ile Glu Phe Gly Leu
            100                 105                 110

Asp Tyr Trp Gly Gln Gly Thr Leu Val Thr Val Ser Pro
        115                 120                 125

<210> SEQ ID NO 156
<211> LENGTH: 125
<212> TYPE: PRT
<213> ORGANISM: human

<400> SEQUENCE: 156

Leu Glu Gln Val Gln Leu Val Glu Ser Gly Gly Gly Val Val Gln Pro
1               5                   10                  15

Gly Arg Ser Leu Arg Leu Ser Cys Ala Ala Ser Gly Val Arg Phe Ser
            20                  25                  30

Ser Tyr Gly Met His Trp Val Arg Gln Ala Pro Gly Lys Gly Leu Glu
        35                  40                  45

Trp Val Ala Ser Ile Ser Ser Asp Ala Thr Lys Lys Asn Tyr Ala Asp
    50                  55                  60

Ser Val Lys Gly Arg Phe Thr Ile Ser Arg Asp Asn Ser Lys Asn Thr
65                  70                  75                  80

Leu His Leu Gln Met Val Thr Leu Arg Pro Glu Asp Thr Ala Val Tyr
                85                  90                  95

Tyr Cys Ala Lys Thr Asp Ile Leu Gly Pro Ala Ile Glu Phe Gly Leu
            100                 105                 110

Asp Tyr Trp Gly Gln Gly Thr Leu Val Thr Val Ser Pro
        115                 120                 125

<210> SEQ ID NO 157
<211> LENGTH: 125
<212> TYPE: PRT
<213> ORGANISM: human

<400> SEQUENCE: 157

Leu Glu Gln Val Gln Leu Val Glu Ser Gly Gly Gly Val Val Gln Pro
1               5                   10                  15

Gly Gly Ser Leu Arg Leu Ser Cys Ala Ala Ser Gly Val Thr Phe Arg
            20                  25                  30

Ser Tyr Gly Met His Trp Val Arg Gln Ala Pro Gly Lys Gly Leu Glu
        35                  40                  45

Trp Val Ala Phe Val Ser Ser Asp Gly Asn Lys Lys Asn Tyr Ala Asp
```

-continued

```
                50                  55                  60
Ser Val Lys Gly Arg Phe Thr Ile Ser Arg Asp Asn Ser Lys Asn Thr
 65                  70                  75                  80

Leu Tyr Leu Gln Met Ile Ser Leu Arg Arg Glu Asp Thr Ala Val Tyr
                 85                  90                  95

Tyr Cys Ala Lys Thr Asp Ile Leu Gly Pro Ala Ile Glu Phe Gly Leu
                100                 105                 110

Asp Tyr Trp Gly Gln Gly Thr Leu Val Thr Val Ser Pro
            115                 120                 125
```

<210> SEQ ID NO 158
<211> LENGTH: 125
<212> TYPE: PRT
<213> ORGANISM: human

<400> SEQUENCE: 158

```
Leu Glu Glu Val Gln Leu Val Glu Ser Gly Gly Val Val Gln Pro
  1               5                  10                  15

Gly Arg Ser Leu Arg Leu Ser Cys Ala Ala Ser Arg Leu Ser Phe Thr
                 20                  25                  30

Ser Tyr Gly Met His Trp Val Arg Gln Ala Pro Gly Lys Gly Leu Glu
                 35                  40                  45

Trp Val Ala Ser Ile Ser Ser Asp Gly Asn Lys Lys Asn Tyr Ala Asp
             50                  55                  60

Ser Val Lys Gly Arg Phe Thr Ile Ser Arg Asp Asn Ser Lys Asn Thr
 65                  70                  75                  80

Leu Ser Leu Gln Met Ile Gly Leu Arg Arg Glu Asp Thr Ala Val Tyr
                 85                  90                  95

Tyr Cys Ala Lys Thr Asp Ile Leu Gly Pro Ala Ile Glu Phe Gly Leu
                100                 105                 110

Asp Tyr Trp Gly Gln Gly Thr Leu Val Thr Val Ser Pro
            115                 120                 125
```

<210> SEQ ID NO 159
<211> LENGTH: 125
<212> TYPE: PRT
<213> ORGANISM: human

<400> SEQUENCE: 159

```
Leu Glu Gln Val Gln Leu Val Glu Ser Gly Gly Val Val Gln Pro
  1               5                  10                  15

Gly Arg Ser Leu Arg Leu Ser Cys Ala Ala Ser Gly Leu Thr Phe Ser
                 20                  25                  30

Ser Tyr Gly Met His Trp Val Arg Gln Ala Pro Gly Lys Gly Leu Glu
                 35                  40                  45

Trp Val Ala Phe Ile Ser Tyr Asp Gly Asn Asn Lys Lys Tyr Ala Asp
             50                  55                  60

Ser Val Lys Gly Arg Phe Thr Ile Ser Arg Asp Asn Ser Lys Asn Arg
 65                  70                  75                  80

Leu Phe Leu Gln Met Val Ser Leu Arg Arg Glu Asp Thr Ala Val Tyr
                 85                  90                  95

Tyr Cys Ala Lys Thr Asp Ile Leu Gly Pro Ala Ile Glu Tyr Gly Leu
                100                 105                 110

Asp Tyr Trp Gly Gln Gly Thr Leu Val Thr Val Ser Ser
            115                 120                 125
```

```
<210> SEQ ID NO 160
<211> LENGTH: 125
<212> TYPE: PRT
<213> ORGANISM: human

<400> SEQUENCE: 160

Leu Glu Glu Val Gln Leu Leu Glu Ser Gly Gly Gly Leu Val Gln Pro
1               5                   10                  15

Gly Gly Ser Leu Arg Ile Ser Cys Ala Gly Ser Gly Phe Arg Phe Gly
            20                  25                  30

Ser Tyr Ala Met Ser Trp Val Arg Gln Ala Pro Gly Lys Gly Leu Glu
        35                  40                  45

Trp Ile Ser Gly Ile Val Gly Thr Gly Gly Asp Thr Lys Tyr Gly Asp
    50                  55                  60

Ser Val Lys Gly Arg Phe Thr Ile Ser Arg Asp Asn Ser Lys Asn Val
65                  70                  75                  80

Val Tyr Leu Gln Met Asn Gly Leu Arg Val Glu Asp Thr Ala Val Tyr
                85                  90                  95

Tyr Cys Ala Lys Ser Ala Tyr Tyr Val Ser Gly Ser Tyr Tyr Gly Phe
            100                 105                 110

Asp Tyr Trp Gly Gln Gly Thr Arg Val Thr Val Ser Ser
        115                 120                 125

<210> SEQ ID NO 161
<211> LENGTH: 125
<212> TYPE: PRT
<213> ORGANISM: human

<400> SEQUENCE: 161

Leu Glu Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Ser Ser Ser
            20                  25                  30

Ala Tyr Ala Leu Ser Trp Val Arg Gln Ile Pro Gly Lys Gly Leu Glu
        35                  40                  45

Trp Val Ser Ala Ile Ser Gly Gly Gly Ser Thr Tyr Tyr Ala Asp
    50                  55                  60

Ser Val Glu Gly Arg Phe Thr Ile Ser Arg Asp Asn Ser Lys Asn Thr
65                  70                  75                  80

Leu Tyr Leu Gln Met Asn Ser Leu Arg Gly Glu Asp Thr Ala Ala Tyr
                85                  90                  95

Tyr Cys Ala Thr Gly Asn Tyr Gly Arg Asn Val Gln Asn Trp Tyr Phe
            100                 105                 110

Asp Leu Trp Gly Arg Gly Thr Leu Val Thr Val Ser Pro
        115                 120                 125

<210> SEQ ID NO 162
<211> LENGTH: 125
<212> TYPE: PRT
<213> ORGANISM: human

<400> SEQUENCE: 162

Leu Glu Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Arg Tyr Asp Ile His Trp Val Arg Gln Ala Pro Gly Lys Gly Leu Glu
        35                  40                  45
```

Trp Val Ala Leu Ile Ser Tyr Asp Gly Met Tyr Lys Ser Ser Ala Asp
            50                  55                  60

Ser Val Lys Gly Arg Phe Thr Val Ser Arg Glu Asn Ser Arg Asn Thr
 65                  70                  75                  80

Val Phe Leu Gln Met Ser Gly Leu Arg Pro Glu Asp Thr Ala Val Tyr
                 85                  90                  95

Phe Cys Ala Lys Ser Asp Val Met Ala Arg Ala Arg Gly Ser Gly Phe
                100                 105                 110

Asp Val Trp Gly Gln Gly Thr Thr Val Thr Val Ser Ser
            115                 120                 125

<210> SEQ ID NO 163
<211> LENGTH: 110
<212> TYPE: PRT
<213> ORGANISM: human

<400> SEQUENCE: 163

Ser Arg Ser Tyr Glu Leu Thr Gln Pro Pro Ser Val Ser Val Ala Pro
 1               5                   10                  15

Gly Gln Thr Ala Arg Ile Thr Cys Gly Gly Asn Thr Ile Gly Ser Gln
                20                  25                  30

Ser Val His Trp Tyr Gln Gln Lys Pro Gly Gln Ala Pro Val Leu Val
                35                  40                  45

Val Tyr Asp Asp Ser Asp Arg Pro Ser Gly Ile Pro Glu Arg Phe Ser
            50                  55                  60

Gly Ser Asn Ser Gly Asn Thr Ala Thr Leu Thr Ile Ser Arg Val Glu
 65                  70                  75                  80

Ala Gly Asp Glu Ala Asp Tyr Tyr Cys Gln Val Trp Asp Ser Ser Ser
                 85                  90                  95

Asp His Val Val Phe Gly Gly Gly Thr Arg Leu Thr Val Leu
                100                 105                 110

<210> SEQ ID NO 164
<211> LENGTH: 112
<212> TYPE: PRT
<213> ORGANISM: human

<400> SEQUENCE: 164

Ser Arg Ser Tyr Val Leu Thr Gln Pro Pro Ser Val Ser Val Ala Pro
 1               5                   10                  15

Gly Gln Thr Ala Ser Ile Ala Cys Gly Gly Asn Asn Ile Gly Ser Lys
                20                  25                  30

Ser Val His Trp Tyr Gln Gln Lys Pro Gly Gln Ala Pro Val Leu Val
                35                  40                  45

Val Tyr Asp Asp Thr Asp Arg Pro Ser Gly Ile Pro Glu Arg Phe Ser
            50                  55                  60

Gly Ser Asn Ser Gly Asn Thr Ala Thr Leu Thr Val Ser Arg Ala Glu
 65                  70                  75                  80

Ala Gly Asp Glu Ala Asp Tyr Tyr Cys Gln Val Trp Asp Ala Ser Ser
                 85                  90                  95

Asp Gln Pro Tyr Val Val Phe Gly Gly Gly Thr Arg Leu Thr Val Leu
                100                 105                 110

<210> SEQ ID NO 165
<211> LENGTH: 110
<212> TYPE: PRT
<213> ORGANISM: human

<400> SEQUENCE: 165

Ser Arg Ser Tyr Glu Leu Thr Gln Pro Pro Ser Val Ser Val Ala Pro
1               5                   10                  15

Arg Thr Asp Gly Gln Ile Thr Cys Gly Glu Asp Lys Ile Glu Ser Lys
            20                  25                  30

Ser Val His Trp Tyr Gln Gln Lys Pro Gly Gln Ala Pro Val Leu Val
        35                  40                  45

Val Tyr Asp Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser Ser
                85                  90                  95

His His Val Val Phe Gly Gly Gly Thr Lys Leu Thr Val Leu
            100                 105                 110

<210> SEQ ID NO 166
<211> LENGTH: 110
<212> TYPE: PRT
<213> ORGANISM: human

<400> SEQUENCE: 166

Ser Arg Leu Pro Val Leu Thr Gln Pro Pro Ser Val Ser Val Ala Pro
1               5                   10                  15

Gly Gln Thr Ala Thr Ile Thr Cys Gly Gly Asn Asn Ile Gly Ser Lys
            20                  25                  30

Ser Val His Trp Phe Gln Gln Lys Pro Gly Gln Ala Pro Val Leu Val
        35                  40                  45

Val Tyr Asp Asp Asn Glu Arg Pro Ser Gly Ile Pro Glu Arg Ile Ser
    50                  55                  60

Gly Ser Asn Ser Gly Asn Thr Ala Thr Leu Thr Ile Ser Arg Val Gly
65                  70                  75                  80

Ala Gly Asp Glu Ala Asp Tyr Tyr Cys Gln Val Trp Asp Ser Ser Ser
                85                  90                  95

Asp His Val Val Phe Gly Gly Gly Thr Lys Leu Thr Val Leu
            100                 105                 110

<210> SEQ ID NO 167
<211> LENGTH: 112
<212> TYPE: PRT
<213> ORGANISM: human

<400> SEQUENCE: 167

Ser Arg Ser Tyr Val Leu Thr Gln Pro Pro Ser Val Ser Val Ala Pro
1               5                   10                  15

Gly Gln Thr Ala Arg Ile Thr Cys Gly Gly Asp Ser Ile Gly Ser Lys
            20                  25                  30

Ser Val His Trp Tyr Gln Gln Lys Pro Gly Gln Ala Pro Val Leu Val
        35                  40                  45

Val Tyr Asp Asp Ser Asp Arg Pro Ser Gly Ile Pro Asx Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp His Ile Thr Ser
                85                  90                  95

-continued

```
Asp His Pro Asn Val Ile Phe Gly Gly Gly Thr Arg Leu Thr Val Leu
            100                 105                 110
```

<210> SEQ ID NO 168
<211> LENGTH: 110
<212> TYPE: PRT
<213> ORGANISM: human

<400> SEQUENCE: 168

```
Ser Arg Ser Tyr Val Leu Thr Gln Pro Pro Ser Val Ser Val Ala Pro
1               5                   10                  15

Gly Gln Thr Ala Arg Ile Thr Cys Gly Gly Asn Asn Ile Gly Ser Lys
            20                  25                  30

Ser Val His Trp Tyr Gln Gln Lys Pro Gly Gln Ala Pro Val Leu Val
        35                  40                  45

Val Tyr Asp Asp Ser Asp Arg Pro Ser Gly Ile Pro Glu Arg Phe Ser
50                  55                  60

Gly Ser Asn Ser Gly Asn Thr Ala Thr Leu Ser Ile Ser Arg Val Glu
65                  70                  75                  80

Ala Gly Asp Glu Ala Asp Tyr His Cys Gln Leu Trp Asp Thr Asn Asn
                85                  90                  95

Asp His Val Val Phe Gly Gly Gly Thr Lys Leu Thr Val Leu
            100                 105                 110
```

<210> SEQ ID NO 169
<211> LENGTH: 112
<212> TYPE: PRT
<213> ORGANISM: human

<400> SEQUENCE: 169

```
Ser Arg Ser Tyr Glu Leu Thr Gln Pro Pro Ser Val Thr Val Val Pro
1               5                   10                  15

Gly Gln Thr Ala Arg Ile Ala Cys Gly Gly Asn Asn Ile Gly Ser Arg
            20                  25                  30

Ser Val His Trp Tyr Gln Gln Lys Pro Gly Gln Ala Pro Leu Leu Leu
        35                  40                  45

Val Tyr Asp Asp Ser Asp Arg Pro Ser Gly Ile Pro Glu Arg Phe Ser
50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys His Val Trp Asp Ser Ser Gly
                85                  90                  95

Asp Leu Pro Asp Val Val Phe Gly Gly Gly Ser Lys Leu Thr Val Leu
            100                 105                 110
```

<210> SEQ ID NO 170
<211> LENGTH: 110
<212> TYPE: PRT
<213> ORGANISM: human
<220> FEATURE:
<221> NAME/KEY: MISC_FEATURE
<222> LOCATION: (26)..(26)
<223> OTHER INFORMATION: Xaa= encoding DNA had a "tga" stop condon in
      CDR1

<400> SEQUENCE: 170

```
Ser Arg Leu Pro Val Leu Thr Gln Pro Pro Ser Val Ser Val Ala Pro
1               5                   10                  15

Gly Gln Thr Ala Arg Ile Thr Cys Gly Xaa Asn Asn Ile Gly Ser Lys
            20                  25                  30
```

```
Ser Val His Trp Tyr Gln Gln Lys Pro Gly Gln Ala Pro Val Leu Val
        35                  40                  45

Val His Asp Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser
                85                  90                  95

Asp His Val Val Phe Gly Gly Gly Thr Lys Leu Thr Val Leu
            100                 105                 110

<210> SEQ ID NO 171
<211> LENGTH: 110
<212> TYPE: PRT
<213> ORGANISM: human

<400> SEQUENCE: 171

Ser Arg Ser Tyr Val Leu Thr Gln Pro Pro Ser Val Ser Val Ala Pro
1               5                   10                  15

Gly Gln Thr Ala Lys Ile Ile Cys Gly Gly Asn Asn Ile Gly Ala Lys
            20                  25                  30

Ser Val Gln Trp Tyr Gln Gln Arg Pro Gly Gln Ala Pro Leu Met Val
        35                  40                  45

Val Tyr Asp Asp Thr Glu Arg Pro Ser Ala Ile Pro Glu Arg Phe Ser
    50                  55                  60

Gly Ser Asn Ser Gly Asn Thr Ala Thr Leu Thr Ile Ser Arg Ala Glu
65                  70                  75                  80

Ala Gly Asp Glu Ala Asp Tyr Tyr Cys Gln Val Trp Asp Asp Ser Ser
                85                  90                  95

Asp His Val Val Phe Gly Gly Gly Thr Lys Leu Ala Val Leu
            100                 105                 110

<210> SEQ ID NO 172
<211> LENGTH: 110
<212> TYPE: PRT
<213> ORGANISM: human

<400> SEQUENCE: 172

Ser Arg Gln Ser Val Leu Thr Gln Pro Pro Ser Val Ser Val Ala Pro
1               5                   10                  15

Gly Gln Thr Ala Arg Ile Thr Cys Gly Gly Asn Asn Ile Gly Ser Lys
            20                  25                  30

Ser Val His Trp Tyr Gln Gln Lys Pro Gly Gln Ala Pro Val Leu Ala
        35                  40                  45

Val Tyr Asp Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser
                85                  90                  95

Asp Pro Val Val Phe Gly Gly Gly Thr Lys Leu Thr Val Leu
            100                 105                 110

<210> SEQ ID NO 173
<211> LENGTH: 110
<212> TYPE: PRT
<213> ORGANISM: human
```

<400> SEQUENCE: 173

Ser Arg Ser Tyr Val Leu Thr Gln Pro Pro Ser Val Ser Val Ala Pro
1               5                   10                  15

Gly Gln Thr Ala Arg Ile Ala Cys Gly Gly Asp Asn Ile Gly Ile Lys
            20                  25                  30

Thr Val Gln Trp Tyr Gln Gln Lys Pro Gly Gln Ala Pro Val Leu Val
        35                  40                  45

Val His Asp Asp Ser Asp Arg Pro Ser Gly Ile Pro Glu Arg Leu Ser
    50                  55                  60

Gly Ser Asn Ser Gly Asn Thr Ala Thr Leu Thr Val Thr Arg Val Glu
65                  70                  75                  80

Ala Gly Asp Glu Ala Asp Tyr Tyr Cys Gln Val Trp Asp Ser Ser Gly
                85                  90                  95

Asp His Pro Val Phe Gly Gly Gly Thr Lys Leu Thr Val Leu
            100                 105                 110

<210> SEQ ID NO 174
<211> LENGTH: 110
<212> TYPE: PRT
<213> ORGANISM: human

<400> SEQUENCE: 174

Ser Arg Gln Pro Val Leu Thr Gln Pro Pro Ser Val Ser Val Ala Pro
1               5                   10                  15

Gly Gln Met Ala Arg Ile Thr Cys Gly Gly Asn Asn Ile Gly Arg Gln
            20                  25                  30

Ser Val Asn Trp Tyr Gln Gln Arg Pro Gly Gln Ala Pro Val Leu Val
        35                  40                  45

Val Tyr Asp Asp Ser Asp Arg Pro Ser Gly Ile Ala Glu Arg Phe Ser
    50                  55                  60

Gly Ser Asn Ser Gly Asn Thr Ala Thr Leu Thr Ile Ser Arg Ala Glu
65                  70                  75                  80

Ala Gly Asp Glu Ala Glu Tyr Tyr Cys Gln Val Trp Asp Ser Ser Ser
                85                  90                  95

Asp His Val Val Phe Gly Gly Gly Thr Thr Leu Thr Val Leu
            100                 105                 110

<210> SEQ ID NO 175
<211> LENGTH: 111
<212> TYPE: PRT
<213> ORGANISM: human

<400> SEQUENCE: 175

Ser Arg Ser Tyr Glu Leu Thr Gln Pro Pro Ser Val Ser Val Ala Pro
1               5                   10                  15

Gly Gln Thr Ala Arg Ile Thr Cys Gly Gly Asn Asn Ile Gly Ser Lys
            20                  25                  30

Ser Val His Trp Tyr Gln Gln Lys Pro Gly Gln Ala Pro Val Leu Val
        35                  40                  45

Val Tyr Asp Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser Ser
                85                  90                  95

```
Asp His Leu Val Val Phe Gly Gly Gly Thr Lys Leu Thr Val Leu
            100                 105                 110
```

<210> SEQ ID NO 176
<211> LENGTH: 112
<212> TYPE: PRT
<213> ORGANISM: human

<400> SEQUENCE: 176

```
Ser Arg Leu Pro Val Leu Thr Gln Pro Pro Ser Val Ser Val Ala Pro
 1               5                  10                  15

Gly Gln Thr Ala Ser Ile Ala Cys Gly Gly Asp Asn Ile Gly Ser Lys
            20                  25                  30

Ser Val His Trp Tyr Gln Gln Lys Ala Gly Gln Ala Pro Val Leu Val
        35                  40                  45

Val Tyr Asp Asp Asn Asp Arg Pro Ser Gly Thr Pro Glu Arg Phe Ser
    50                  55                  60

Gly Ser Asn Ser Gly Asn Thr Ala Thr Leu Thr Val Ser Arg Val Glu
 65                  70                  75                  80

Ala Gly Asp Glu Ala Asp Tyr Phe Cys Gln Val Trp Asp Ser Thr Ser
                85                  90                  95

Asp His Pro Tyr Val Val Phe Gly Gly Gly Thr Lys Leu Thr Val Leu
            100                 105                 110
```

<210> SEQ ID NO 177
<211> LENGTH: 110
<212> TYPE: PRT
<213> ORGANISM: human

<400> SEQUENCE: 177

```
Ser Arg Ser Tyr Val Leu Thr Gln Pro Pro Ser Val Ser Val Ala Pro
 1               5                  10                  15

Gly Gln Thr Ala Arg Ile Thr Cys Gly Gly Asn Ser Ile Gly Ser Lys
            20                  25                  30

Ser Val His Trp Tyr Gln Gln Lys Pro Gly Gln Ala Pro Val Leu Val
        35                  40                  45

Val Tyr Asp Asp Ser Asp Arg Pro Ser Gly Ile Pro Glu Arg Phe Ser
    50                  55                  60

Gly Ser Asn Ser Gly Thr Thr Ala Thr Leu Thr Ile Ser Arg Val Glu
 65                  70                  75                  80

Ala Gly Asp Glu Ala Asp Tyr Tyr Cys Gln Val Trp Asp Ser Thr Gly
                85                  90                  95

Asp Arg Val Val Phe Gly Gly Gly Thr Lys Leu Thr Val Leu
            100                 105                 110
```

<210> SEQ ID NO 178
<211> LENGTH: 111
<212> TYPE: PRT
<213> ORGANISM: human

<400> SEQUENCE: 178

```
Ser Arg Gln Ala Val Leu Thr Gln Pro Pro Ser Val Ser Val Ala Pro
 1               5                  10                  15

Gly Gln Thr Ala Arg Ile Thr Cys Gly Gly Asn Asn Ile Gly Ser Lys
            20                  25                  30

Ser Ala His Trp Tyr Gln Gln Arg Pro Gly Gln Ala Pro Leu Leu Val
        35                  40                  45

Val Tyr Asp Asp Ser Asp Arg Pro Ser Gly Ile Pro Glu Arg Phe Ser
```

```
                50                  55                  60
Gly Ser Asn Ser Gly Asn Ala Ala Thr Leu Thr Ile Thr Arg Val Glu
 65                  70                  75                  80

Ala Gly Asp Glu Ala Asp Tyr Tyr Cys Gln Val Trp Gly Asp Thr Gly
                 85                  90                  95

Asp His Pro Val Val Phe Gly Gly Gly Thr Lys Leu Thr Val Leu
                100                 105                 110
```

<210> SEQ ID NO 179
<211> LENGTH: 20
<212> TYPE: DNA
<213> ORGANISM: artificial sequence
<220> FEATURE:
<223> OTHER INFORMATION: restriction oligonucleotide

<400> SEQUENCE: 179
agggcctgag ctcgcccgtc                                              20

<210> SEQ ID NO 180
<211> LENGTH: 21
<212> TYPE: DNA
<213> ORGANISM: artificial sequence
<220> FEATURE:
<223> OTHER INFORMATION: restriction oligonucleotide

<400> SEQUENCE: 180
gacttctacc cgggagcygt g                                            21

<210> SEQ ID NO 181
<211> LENGTH: 48
<212> TYPE: DNA
<213> ORGANISM: artificial sequence
<220> FEATURE:
<223> OTHER INFORMATION: primer

<400> SEQUENCE: 181
gacgaccggc taccaagagg acagtctaga cagtctgtgc tgactcag               48

<210> SEQ ID NO 182
<211> LENGTH: 48
<212> TYPE: DNA
<213> ORGANISM: artificial sequence
<220> FEATURE:
<223> OTHER INFORMATION: primer

<400> SEQUENCE: 182
gacgaccggc taccaagagg acagtctaga cagtctgtgy tgacgcag               48

<210> SEQ ID NO 183
<211> LENGTH: 48
<212> TYPE: DNA
<213> ORGANISM: artificial sequence
<220> FEATURE:
<223> OTHER INFORMATION: primer

<400> SEQUENCE: 183
gacgaccggc taccaagagg acagtctaga cagtctgtcg tgacgcag               48

<210> SEQ ID NO 184
<211> LENGTH: 48
<212> TYPE: DNA
<213> ORGANISM: artificial sequence
<220> FEATURE:
<223> OTHER INFORMATION: primer

<400> SEQUENCE: 184
gacgaccggc taccaagagg acagtctaga cagtctgccc tgactcag            48

<210> SEQ ID NO 185
<211> LENGTH: 48
<212> TYPE: DNA
<213> ORGANISM: artificial sequence
<220> FEATURE:
<223> OTHER INFORMATION: primer

<400> SEQUENCE: 185
gacgaccggc taccaagagg acagtctaga tcctatgwgc tgactcag            48

<210> SEQ ID NO 186
<211> LENGTH: 48
<212> TYPE: DNA
<213> ORGANISM: artificial sequence
<220> FEATURE:
<223> OTHER INFORMATION: primer

<400> SEQUENCE: 186
gacgaccggc taccaagagg acagtctaga tcctatgagc tgacacag            48

<210> SEQ ID NO 187
<211> LENGTH: 48
<212> TYPE: DNA
<213> ORGANISM: artificial sequence
<220> FEATURE:
<223> OTHER INFORMATION: primer

<400> SEQUENCE: 187
gacgaccggc taccaagagg acagtctaga tcttctgagc tgactcag            48

<210> SEQ ID NO 188
<211> LENGTH: 48
<212> TYPE: DNA
<213> ORGANISM: artificial sequence
<220> FEATURE:
<223> OTHER INFORMATION: primer

<400> SEQUENCE: 188
gacgaccggc taccaagagg acagtctaga tcctatgagc tgatgcag            48

<210> SEQ ID NO 189
<211> LENGTH: 48
<212> TYPE: DNA
<213> ORGANISM: artificial sequence
<220> FEATURE:
<223> OTHER INFORMATION: primer

<400> SEQUENCE: 189
gacgaccggc taccaagagg acagtctaga cagcytgtgc tgactcaa            48

<210> SEQ ID NO 190
<211> LENGTH: 48
<212> TYPE: DNA
<213> ORGANISM: artificial sequence
<220> FEATURE:
<223> OTHER INFORMATION: primer

<400> SEQUENCE: 190
gacgaccggc taccaagagg acagtctaga cagsctgtgc tgactcag            48

<210> SEQ ID NO 191
<211> LENGTH: 48

```
<212> TYPE: DNA
<213> ORGANISM: artificial sequence
<220> FEATURE:
<223> OTHER INFORMATION: primer

<400> SEQUENCE: 191
gacgaccggc taccaagagg acagtctaga aattttatgc tgactcag        48

<210> SEQ ID NO 192
<211> LENGTH: 48
<212> TYPE: DNA
<213> ORGANISM: artificial sequence
<220> FEATURE:
<223> OTHER INFORMATION: primer

<400> SEQUENCE: 192
gacgaccggc taccaagagg acagtctaga cagrctgtgg tgactcag        48

<210> SEQ ID NO 193
<211> LENGTH: 48
<212> TYPE: DNA
<213> ORGANISM: artificial sequence
<220> FEATURE:
<223> OTHER INFORMATION: primer

<400> SEQUENCE: 193
gacgaccggc taccaagagg acagtctaga cagactgtgg tgacccag        48

<210> SEQ ID NO 194
<211> LENGTH: 48
<212> TYPE: DNA
<213> ORGANISM: artificial sequence
<220> FEATURE:
<223> OTHER INFORMATION: primer

<400> SEQUENCE: 194
gacgaccggc taccaagagg acagtctaga cwgcctgtgc tgactcag        48

<210> SEQ ID NO 195
<211> LENGTH: 48
<212> TYPE: DNA
<213> ORGANISM: artificial sequence
<220> FEATURE:
<223> OTHER INFORMATION: primer

<400> SEQUENCE: 195
gacgaccggc taccaagagg acagtctaga caggcagggc tgactcag        48

<210> SEQ ID NO 196
<211> LENGTH: 56
<212> TYPE: DNA
<213> ORGANISM: artificial sequence
<220> FEATURE:
<223> OTHER INFORMATION: nested oligonucleotide

<400> SEQUENCE: 196
gacgaccggc taccaagagg agtgctcgag ctcaggccct gatgggtgac ttcgct    56

<210> SEQ ID NO 197
<211> LENGTH: 60
<212> TYPE: DNA
<213> ORGANISM: artificial sequence
<220> FEATURE:
<223> OTHER INFORMATION: nested oligonucleotide

<400> SEQUENCE: 197
```

```
gacgaccggc taccaagagg acagaagagc tcctgggtag aagtcactka tsagrcacag      60
```

<210> SEQ ID NO 198
<211> LENGTH: 24
<212> TYPE: DNA
<213> ORGANISM: artificial sequence
<220> FEATURE:
<223> OTHER INFORMATION: primer

<400> SEQUENCE: 198

```
gacgaccggc taccaagagg agtg                                             24
```

<210> SEQ ID NO 199
<211> LENGTH: 24
<212> TYPE: DNA
<213> ORGANISM: artificial sequence
<220> FEATURE:
<223> OTHER INFORMATION: primer

<400> SEQUENCE: 199

```
gacgaccggc taccaagagg acag                                             24
```

<210> SEQ ID NO 200
<211> LENGTH: 25
<212> TYPE: DNA
<213> ORGANISM: artificial sequence
<220> FEATURE:
<223> OTHER INFORMATION: restriction oligonucleotide

<400> SEQUENCE: 200

```
ctaactccat ggtgaccctg ggatg                                            25
```

<210> SEQ ID NO 201
<211> LENGTH: 24
<212> TYPE: DNA
<213> ORGANISM: artificial sequence
<220> FEATURE:
<223> OTHER INFORMATION: restriction oligonucleotide

<400> SEQUENCE: 201

```
caactggctc ctcggtgact ctag                                             24
```

<210> SEQ ID NO 202
<211> LENGTH: 24
<212> TYPE: DNA
<213> ORGANISM: artificial sequence
<220> FEATURE:
<223> OTHER INFORMATION: restriction oligonucleotide

<400> SEQUENCE: 202

```
cagtgagcag ttaacatctg gagg                                             24
```

<210> SEQ ID NO 203
<211> LENGTH: 47
<212> TYPE: DNA
<213> ORGANISM: artificial sequence
<220> FEATURE:
<223> OTHER INFORMATION: primer

<400> SEQUENCE: 203

```
gacgtggccg ttggaagagg agtgctcgag gtccaactgc agcagyc                    47
```

<210> SEQ ID NO 204
<211> LENGTH: 23
<212> TYPE: DNA
<213> ORGANISM: artificial sequence

```
<220> FEATURE:
<223> OTHER INFORMATION: primer

<400> SEQUENCE: 204
catggagtta gtttgggcag cag                                             23

<210> SEQ ID NO 205
<211> LENGTH: 22
<212> TYPE: DNA
<213> ORGANISM: artificial sequence
<220> FEATURE:
<223> OTHER INFORMATION: primer

<400> SEQUENCE: 205
caacgttgca ggtgacggtc tc                                              22

<210> SEQ ID NO 206
<211> LENGTH: 23
<212> TYPE: DNA
<213> ORGANISM: artificial sequence
<220> FEATURE:
<223> OTHER INFORMATION: primer

<400> SEQUENCE: 206
cgaggagcca gttgtatctc cac                                             23

<210> SEQ ID NO 207
<211> LENGTH: 22
<212> TYPE: DNA
<213> ORGANISM: artificial sequence
<220> FEATURE:
<223> OTHER INFORMATION: primer

<400> SEQUENCE: 207
ccacattgca ggtgatggac tg                                              22

<210> SEQ ID NO 208
<211> LENGTH: 52
<212> TYPE: DNA
<213> ORGANISM: artificial sequence
<220> FEATURE:
<223> OTHER INFORMATION: primer

<400> SEQUENCE: 208
gacgaccggc taccaagagg agtgtctaga gaaawtgtgc tcacccagtc tc             52

<210> SEQ ID NO 209
<211> LENGTH: 22
<212> TYPE: DNA
<213> ORGANISM: artificial sequence
<220> FEATURE:
<223> OTHER INFORMATION: primer

<400> SEQUENCE: 209
ctgctcactg gatggtggga ag                                              22

<210> SEQ ID NO 210
<211> LENGTH: 23
<212> TYPE: DNA
<213> ORGANISM: artificial sequence
<220> FEATURE:
<223> OTHER INFORMATION: primer

<400> SEQUENCE: 210
gagtggcctc acaggtatag ctg                                             23
```

<210> SEQ ID NO 211
<211> LENGTH: 52
<212> TYPE: DNA
<213> ORGANISM: artificial sequence
<220> FEATURE:
<223> OTHER INFORMATION: primer

<400> SEQUENCE: 211
gacgaccggc taccaagagg agtgtctaga gacattgtga tgwcacagtc tc            52

<210> SEQ ID NO 212
<211> LENGTH: 52
<212> TYPE: DNA
<213> ORGANISM: artificial sequence
<220> FEATURE:
<223> OTHER INFORMATION: primer

<400> SEQUENCE: 212
gacgaccggc taccaagagg agtgtctaga gatgttktga tgacccarac tc            52

<210> SEQ ID NO 213
<211> LENGTH: 52
<212> TYPE: DNA
<213> ORGANISM: artificial sequence
<220> FEATURE:
<223> OTHER INFORMATION: primer

<400> SEQUENCE: 213
gacgaccggc taccaagagg agtgtctaga gacattgtga tgackcaggc tg            52

<210> SEQ ID NO 214
<211> LENGTH: 52
<212> TYPE: DNA
<213> ORGANISM: artificial sequence
<220> FEATURE:
<223> OTHER INFORMATION: primer

<400> SEQUENCE: 214
gacgaccggc taccaagagg agtgtctaga gacawtgtgc tgacccartc tc            52

<210> SEQ ID NO 215
<211> LENGTH: 52
<212> TYPE: DNA
<213> ORGANISM: artificial sequence
<220> FEATURE:
<223> OTHER INFORMATION: primer

<400> SEQUENCE: 215
gacgaccggc taccaagagg agtgtctaga gaaawtgtgc tcacccagtc tc            52

<210> SEQ ID NO 216
<211> LENGTH: 52
<212> TYPE: DNA
<213> ORGANISM: artificial sequence
<220> FEATURE:
<223> OTHER INFORMATION: primer

<400> SEQUENCE: 216
gacgaccggc taccaagagg agtgtctaga gacatccaga tgacmcagtc tc            52

<210> SEQ ID NO 217
<211> LENGTH: 53
<212> TYPE: DNA
<213> ORGANISM: artificial sequence
<220> FEATURE:
<223> OTHER INFORMATION: primer

```
<400> SEQUENCE: 217
gacgaccggc taccaagagg agtgtctaga gatatccaga tgacacagac tac         53

<210> SEQ ID NO 218
<211> LENGTH: 50
<212> TYPE: DNA
<213> ORGANISM: artificial sequence
<220> FEATURE:
<223> OTHER INFORMATION: primer

<400> SEQUENCE: 218
gacgaccggc taccaagagg agtgtctaga gacattgtsa tgacccagtc              50

<210> SEQ ID NO 219
<211> LENGTH: 52
<212> TYPE: DNA
<213> ORGANISM: artificial sequence
<220> FEATURE:
<223> OTHER INFORMATION: primer

<400> SEQUENCE: 219
gacgaccggc taccaagagg agtgtctaga caaattgttc tcacccagtc tc           52

<210> SEQ ID NO 220
<211> LENGTH: 62
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (62)..(62)
<223> OTHER INFORMATION: n= G2'OMe[A(ps)U(ps)U(ps)](propyl)

<400> SEQUENCE: 220
gacgaccggc taccaagagg agtgtccgga tgttaactgc tcactggatg gtgggaagat   60 gn                                                                  62

<210> SEQ ID NO 221
<211> LENGTH: 24
<212> TYPE: DNA
<213> ORGANISM: artificial sequence
<220> FEATURE:
<223> OTHER INFORMATION: primer

<400> SEQUENCE: 221
gacgaccggc taccaagagg agtg                                          24

<210> SEQ ID NO 222
<211> LENGTH: 47
<212> TYPE: DNA
<213> ORGANISM: artificial sequence
<220> FEATURE:
<223> OTHER INFORMATION: primer

<400> SEQUENCE: 222
gacgtggccg ttggaagagg agtgctcgag gtgcagcttc agsagtc                 47

<210> SEQ ID NO 223
<211> LENGTH: 47
<212> TYPE: DNA
<213> ORGANISM: artificial sequence
<220> FEATURE:
<223> OTHER INFORMATION: primer
```

<400> SEQUENCE: 223
gacgtggccg ttggaagagg agtgctcgag gtgcagctga agsagtc        47

<210> SEQ ID NO 224
<211> LENGTH: 47
<212> TYPE: DNA
<213> ORGANISM: artificial sequence
<220> FEATURE:
<223> OTHER INFORMATION: primer

<400> SEQUENCE: 224
gacgtggccg ttggaagagg agtgctcgag gtycagctgc arcartc        47

<210> SEQ ID NO 225
<211> LENGTH: 47
<212> TYPE: DNA
<213> ORGANISM: artificial sequence
<220> FEATURE:
<223> OTHER INFORMATION: primer

<400> SEQUENCE: 225
gacgtggccg ttggaagagg agtgctcgag gtccaactgc agcagyc        47

<210> SEQ ID NO 226
<211> LENGTH: 47
<212> TYPE: DNA
<213> ORGANISM: artificial sequence
<220> FEATURE:
<223> OTHER INFORMATION: primer

<400> SEQUENCE: 226
gacgtggccg ttggaagagg agtgctcgag gttcagctgc agcagtc        47

<210> SEQ ID NO 227
<211> LENGTH: 47
<212> TYPE: DNA
<213> ORGANISM: artificial sequence
<220> FEATURE:
<223> OTHER INFORMATION: primer

<400> SEQUENCE: 227
gacgtggccg ttggaagagg agtgctcgag gtgaagctgg tggagwc        47

<210> SEQ ID NO 228
<211> LENGTH: 47
<212> TYPE: DNA
<213> ORGANISM: artificial sequence
<220> FEATURE:
<223> OTHER INFORMATION: primer

<400> SEQUENCE: 228
gacgtggccg ttggaagagg agtgctcgag gtgaagcttc tggagtc        47

<210> SEQ ID NO 229
<211> LENGTH: 47
<212> TYPE: DNA
<213> ORGANISM: artificial sequence
<220> FEATURE:
<223> OTHER INFORMATION: primer

<400> SEQUENCE: 229
gacgtggccg ttggaagagg agtgctcgag gtgmagctgg tggagtc        47

<210> SEQ ID NO 230
<211> LENGTH: 59

```
<212> TYPE: DNA
<213> ORGANISM: artificial sequence
<220> FEATURE:
<223> OTHER INFORMATION: nested oligonucleotide
<220> FEATURE:
<221> NAME/KEY: misc_feature
<222> LOCATION: (59)..(59)
<223> OTHER INFORMATION: n= A2'OMe[U(ps)C(ps)A(ps)](propyl)

<400> SEQUENCE: 230
gacgtggccg ttggaagagg agtgcctagg gttaccatgg agttagtttg ggcagcagn     59

<210> SEQ ID NO 231
<211> LENGTH: 59
<212> TYPE: DNA
<213> ORGANISM: artificial sequence
<220> FEATURE:
<223> OTHER INFORMATION: nested oligonucleotide
<220> FEATURE:
<221> NAME/KEY: misc_feature
<222> LOCATION: (59)..(59)
<223> OTHER INFORMATION: n=A2'OMe[C(ps)A(ps)U(ps)](propyl)

<400> SEQUENCE: 231
gacgtggccg ttggaagagg agtgcctagg gtcatcgagg agccagttgt atctccacn     59

<210> SEQ ID NO 232
<211> LENGTH: 24
<212> TYPE: DNA
<213> ORGANISM: artificial sequence
<220> FEATURE:
<223> OTHER INFORMATION: primer

<400> SEQUENCE: 232
gacgtggccg ttggaagagg agtg                                           24

<210> SEQ ID NO 233
<211> LENGTH: 113
<212> TYPE: PRT
<213> ORGANISM: mouse

<400> SEQUENCE: 233

Gln Ser Gly Ala Glu Leu Met Lys Pro Gly Ala Ser Val Lys Ile Ser
1               5                   10                  15

Cys Lys Ala Thr Asp Tyr Thr Phe Ser Asn Tyr Trp Ile Glu Trp Val
            20                  25                  30

Lys Gln Arg Pro Gly His Gly Leu Glu Trp Ile Gly Glu Ile Leu Pro
        35                  40                  45

Gly Ser Gly Ser Thr Asn Phe Asn Glu Lys Phe Lys Gly Lys Ala Thr
    50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Phe
                85                  90                  95

Thr Phe Ser Leu Asp Tyr Trp Gly Gln Gly Thr Thr Leu Thr Val Ser
            100                 105                 110

Ser

<210> SEQ ID NO 234
<211> LENGTH: 113
<212> TYPE: PRT
<213> ORGANISM: mouse

<400> SEQUENCE: 234
```

-continued

Gln Ser Gly Ala Glu Leu Ile Lys Pro Gly Ala Ser Val Lys Ile Ser
1               5                   10                  15

Cys Arg Thr Thr Asp Tyr Thr Phe Ser Asn Tyr Trp Ile Glu Trp Val
            20                  25                  30

Lys Arg Arg Pro Gly His Gly Leu Glu Trp Ile Gly Glu Ile Leu Pro
        35                  40                  45

Gly Thr Gly Asp Thr Asn Phe Asn Glu Lys Phe Arg Gly Lys Ala Thr
    50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Phe
                85                  90                  95

Thr Phe Ser Phe Asp Tyr Trp Gly Gln Gly Thr Thr Leu Thr Val Ser
            100                 105                 110

Ser

<210> SEQ ID NO 235
<211> LENGTH: 113
<212> TYPE: PRT
<213> ORGANISM: mouse

<400> SEQUENCE: 235

Gln Ser Gly Ala Glu Leu Met Lys Pro Gly Ala Ser Val Lys Ile Ser
1               5                   10                  15

Cys Lys Ala Thr Asp Tyr Thr Phe Ser Asn Tyr Trp Ile Glu Trp Ile
            20                  25                  30

Lys Gln Arg Pro Gly His Gly Leu Glu Trp Ile Gly Glu Ile Leu Pro
        35                  40                  45

Gly Ser Gly Asp Thr Asn Phe Asn Glu Arg Phe Lys Asp Lys Ala Thr
    50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Tyr
                85                  90                  95

Thr Phe Ser Phe Asp Tyr Trp Gly Gln Gly Thr Thr Leu Thr Val Ser
            100                 105                 110

Ser

<210> SEQ ID NO 236
<211> LENGTH: 113
<212> TYPE: PRT
<213> ORGANISM: mouse

<400> SEQUENCE: 236

Gln Ser Gly Ala Glu Val Met Lys Pro Gly Ala Ser Val Lys Ile Ser
1               5                   10                  15

Cys Lys Ala Ser Asp Tyr Thr Phe Ser Asn Tyr Trp Ile Glu Trp Val
            20                  25                  30

Lys Gln Arg Pro Gly His Gly Leu Glu Trp Ile Gly Glu Ile Leu Pro
        35                  40                  45

Gly Ser Gly Asp Thr Asn Val Asn Glu Lys Phe Lys Gly Lys Ala Thr
    50                  55                  60

Phe Thr Ala Tyr Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Tyr

-continued

```
                85                  90                  95
Thr Phe Ser Phe Asp Tyr Trp Gly Gln Gly Thr Thr Leu Thr Val Ser
            100                 105                 110
Ser

<210> SEQ ID NO 237
<211> LENGTH: 113
<212> TYPE: PRT
<213> ORGANISM: mouse

<400> SEQUENCE: 237

Gln Ser Gly Ala Glu Leu Met Lys Pro Gly Ala Ser Val Lys Ile Ser
1               5                   10                  15

Cys Lys Ala Ser Asp Tyr Thr Phe Ser Asn Tyr Trp Ile Glu Trp Val
            20                  25                  30

Lys Gln Arg Pro Gly His Gly Leu Glu Trp Ile Gly Glu Ile Leu Pro
        35                  40                  45

Gly Ser Gly Asp Thr Asn Val Asn Glu Lys Phe Lys Gly Lys Ala Thr
    50                  55                  60

Phe Leu Ala Tyr Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Tyr
                85                  90                  95

Thr Phe Ser Phe Asp Tyr Trp Gly Gln Gly Thr Thr Leu Thr Val Ser
            100                 105                 110

Ser

<210> SEQ ID NO 238
<211> LENGTH: 113
<212> TYPE: PRT
<213> ORGANISM: mouse

<400> SEQUENCE: 238

Gln Ser Gly Ala Glu Leu Met Lys Pro Gly Ala Ser Val Lys Ile Ser
1               5                   10                  15

Cys Lys Ala Thr Asp Tyr Thr Phe Ser Asn Tyr Trp Ile Glu Trp Val
            20                  25                  30

Lys Gln Arg Pro Gly His Gly Leu Glu Trp Ile Gly Glu Ile Leu Pro
        35                  40                  45

Gly Ser Gly Asp Thr Asn Phe Asn Glu Lys Phe Lys Gly Lys Ala Thr
    50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Tyr
                85                  90                  95

Thr Phe Ser Phe Asp Tyr Trp Gly Gln Gly Thr Thr Leu Thr Val Ser
            100                 105                 110

Ser

<210> SEQ ID NO 239
<211> LENGTH: 113
<212> TYPE: PRT
<213> ORGANISM: mouse

<400> SEQUENCE: 239

Gln Ser Gly Ala Glu Leu Met Lys Pro Gly Ala Ser Val Lys Ile Ser
1               5                   10                  15
```

```
Cys Lys Ala Ser Asp Tyr Thr Phe Ser Asn Tyr Trp Ile Glu Trp Val
             20                  25                  30

Lys Gln Arg Pro Gly His Gly Leu Glu Trp Ile Gly Glu Ile Leu Pro
             35                  40                  45

Gly Thr Gly Asp Thr Asn Phe Asn Glu Lys Phe Arg Gly Lys Ala Thr
         50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Phe
                 85                  90                  95

Thr Phe Ser Phe Asp Tyr Trp Gly Gln Gly Thr Thr Leu Thr Val Ser
            100                 105                 110

Ser
```

<210> SEQ ID NO 240
<211> LENGTH: 113
<212> TYPE: PRT
<213> ORGANISM: mouse

<400> SEQUENCE: 240

```
Gln Ser Gly Ala Glu Leu Met Lys Pro Gly Ala Ser Val Lys Ile Ser
1               5                   10                  15

Cys Lys Ala Thr Asp Tyr Thr Phe Ser Asn Tyr Trp Ile Glu Trp Val
             20                  25                  30

Lys Gln Arg Pro Gly His Gly Leu Glu Trp Ile Gly Glu Ile Leu Pro
             35                  40                  45

Gly Ser Gly Ser Thr Asn Phe Asn Glu Lys Phe Lys Gly Lys Ala Thr
         50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Phe
                 85                  90                  95

Thr Phe Ser Phe Asp Tyr Trp Gly Gln Gly Thr Thr Leu Thr Val Ser
            100                 105                 110

Ser
```

<210> SEQ ID NO 241
<211> LENGTH: 109
<212> TYPE: PRT
<213> ORGANISM: mouse

<400> SEQUENCE: 241

```
Gln Ser Gly Ala Glu Leu Met Lys Pro Gly Ala Ser Val Lys Ile Ser
1               5                   10                  15

Cys Lys Ala Thr Asp Tyr Thr Phe Ser Asn Tyr Trp Ile Glu Trp Val
             20                  25                  30

Lys Gln Arg Pro Gly His Gly Leu Glu Trp Ile Gly Asp Ile Leu Pro
             35                  40                  45

Gly Ser Gly Asp Thr Asn Val Asn Glu Lys Phe Lys Gly Lys Ala Thr
         50                  55                  60

Phe Thr Ala Asp Thr Ser Ser Asn Thr Ala Tyr Met Gln Leu Ser Ser
65                  70                  75                  80

Leu Thr Ser Glu Asp Ser Ala Val Tyr Tyr Cys Ala Arg Ala Tyr Tyr
                 85                  90                  95

Thr Leu Ser Phe Asp Tyr Trp Gly Gln Gly Thr Thr Leu
```

-continued

<210> SEQ ID NO 242
<211> LENGTH: 110
<212> TYPE: PRT
<213> ORGANISM: mouse

<400> SEQUENCE: 242

Ala Glu Leu Met Lys Pro Gly Ala Ser Val Lys Ile Ser Cys Lys Ala
1               5                   10                  15

Thr Asp Tyr Thr Phe Ser Asn Tyr Trp Ile Glu Trp Val Lys Gln Arg
            20                  25                  30

Pro Gly His Gly Leu Glu Trp Ile Gly Glu Ile Leu Pro Gly Ser Gly
        35                  40                  45

Asp Thr Asn Phe Asn Glu Lys Phe Lys Gly Lys Ala Thr Phe Thr Ala
    50                  55                  60

Tyr Thr Ser Ser Asn Thr Ala Tyr Met Gln Leu Ser Ser Leu Thr Ser
65                  70                  75                  80

Glu Asp Ser Ala Val Tyr Tyr Cys Ala Arg Ala Tyr Tyr Thr Phe Ser
                85                  90                  95

Phe Asp Tyr Trp Gly Gln Gly Thr Thr Leu Thr Val Ser Ser
            100                 105                 110

<210> SEQ ID NO 243
<211> LENGTH: 110
<212> TYPE: PRT
<213> ORGANISM: mouse

<400> SEQUENCE: 243

Ala Glu Leu Met Lys Pro Gly Ala Ser Val Lys Ile Ser Cys Lys Ala
1               5                   10                  15

Thr Asp Tyr Thr Phe Ser Asn Tyr Trp Ile Glu Trp Val Lys Gln Arg
            20                  25                  30

Pro Gly His Gly Leu Glu Trp Ile Gly Glu Ile Leu Pro Gly Ser Gly
        35                  40                  45

Asp Thr Asn Phe Asn Glu Lys Phe Lys Gly Lys Ala Thr Phe Thr Ala
    50                  55                  60

Ser Thr Ser Ser Asn Thr Ala Tyr Met Gln Leu Ser Ser Leu Thr Ser
65                  70                  75                  80

Glu Asp Ser Ala Val Tyr Tyr Cys Ala Arg Ala Tyr Tyr Thr Phe Ser
                85                  90                  95

Phe Asp Tyr Trp Gly Gln Gly Thr Thr Leu Thr Val Ser Ser
            100                 105                 110

<210> SEQ ID NO 244
<211> LENGTH: 110
<212> TYPE: PRT
<213> ORGANISM: mouse

<400> SEQUENCE: 244

Ala Glu Leu Met Lys Pro Gly Ala Ser Val Lys Ile Ser Cys Lys Ala
1               5                   10                  15

Ser Asp Tyr Thr Phe Ser Asn Tyr Trp Ile Glu Trp Val Lys Gln Arg
            20                  25                  30

Pro Gly His Gly Leu Glu Trp Ile Gly Glu Ile Leu Pro Gly Ser Gly
        35                  40                  45

Asp Ala Asn Phe Asn Glu Lys Phe Lys Gly Lys Ala Thr Phe Thr Ala
    50                  55                  60

```
Tyr Thr Ser Ser Asn Thr Ala Tyr Met Gln Leu Ser Ser Leu Thr Ser
 65                  70                  75                  80

Glu Asp Ser Ala Val Tyr Tyr Cys Ala Arg Ala Tyr Tyr Thr Phe Ser
                 85                  90                  95

Phe Asp Tyr Trp Gly Gln Gly Thr Thr Leu Thr Val Ser Ser
            100                 105                 110

<210> SEQ ID NO 245
<211> LENGTH: 110
<212> TYPE: PRT
<213> ORGANISM: mouse

<400> SEQUENCE: 245

Ala Glu Val Met Lys Pro Gly Ala Ser Val Lys Ile Ser Cys Lys Ala
  1               5                  10                  15

Ser Asp Tyr Thr Phe Ser Asn Tyr Trp Ile Glu Trp Val Lys Gln Arg
                 20                  25                  30

Pro Gly His Gly Leu Glu Trp Ile Gly Glu Ile Leu Pro Gly Ser Gly
             35                  40                  45

Asp Thr Asn Val Ser Glu Lys Phe Lys Gly Lys Ala Thr Phe Thr Ala
 50                  55                  60

Tyr Thr Ser Ser Asn Thr Ala Tyr Met Gln Leu Ser Ser Leu Thr Ser
 65                  70                  75                  80

Glu Asp Ser Ala Val Tyr Tyr Cys Ala Arg Ala Tyr Tyr Thr Phe Ser
                 85                  90                  95

Phe Asp Tyr Trp Gly Gln Gly Thr Thr Leu Thr Val Ser Ser
            100                 105                 110

<210> SEQ ID NO 246
<211> LENGTH: 110
<212> TYPE: PRT
<213> ORGANISM: mouse

<400> SEQUENCE: 246

Ala Glu Leu Met Lys Pro Gly Ala Ser Val Lys Ile Ser Cys Lys Ala
  1               5                  10                  15

Thr Asp Tyr Thr Phe Ser Asn Tyr Trp Ile Glu Trp Val Lys Gln Arg
                 20                  25                  30

Pro Gly His Gly Leu Glu Trp Ile Gly Glu Ile Leu Pro Gly Ser Gly
             35                  40                  45

Asp Thr Asn Phe Asn Glu Lys Phe Lys Gly Lys Ala Thr Phe Thr Ala
 50                  55                  60

Asp Thr Ser Ser Asn Thr Ala Tyr Met Gln Leu Ser Ser Leu Thr Ser
 65                  70                  75                  80

Glu Asp Ser Ala Val Tyr Tyr Cys Ala Arg Ala Tyr Tyr Thr Leu Ser
                 85                  90                  95

Phe Asp Tyr Trp Gly Gln Gly Thr Thr Leu Thr Val Ser Ser
            100                 105                 110

<210> SEQ ID NO 247
<211> LENGTH: 112
<212> TYPE: PRT
<213> ORGANISM: mouse

<400> SEQUENCE: 247

Gly Ala Glu Leu Met Lys Pro Gly Ala Ser Val Lys Ile Ser Cys Lys
  1               5                  10                  15
```

```
Ala Thr Gly Tyr Thr Phe Asn Thr Tyr Trp Ile Glu Trp Val Lys Gln
            20                  25                  30

Arg Pro Gly His Gly Leu Glu Trp Ile Gly Glu Ile Leu Pro Gly Thr
            35                  40                  45

Asp Asn Thr Asn Tyr Asn Glu Lys Phe Lys Gly Lys Ala Thr Phe Thr
        50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Phe Phe Asp Tyr Trp Gly Gln Gly Thr Thr Leu Thr Val Ser Ser
            100                 105                 110
```

<210> SEQ ID NO 248
<211> LENGTH: 112
<212> TYPE: PRT
<213> ORGANISM: mouse

<400> SEQUENCE: 248

```
Gly Ala Glu Leu Met Lys Pro Gly Ala Ser Val Lys Ile Ser Cys Lys
1               5                   10                  15

Ala Thr Gly Tyr Thr Phe Asn Thr Tyr Trp Ile Glu Trp Val Lys Gln
            20                  25                  30

Arg Pro Gly His Gly Leu Glu Trp Ile Gly Glu Ile Leu Pro Gly Thr
            35                  40                  45

Asp Asn Thr Asn Tyr Asn Glu Lys Phe Lys Gly Lys Ala Thr Phe Thr
        50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Phe Phe Asp Tyr Trp Gly Gln Gly Thr Thr Leu Thr Val Ser Ser
            100                 105                 110
```

<210> SEQ ID NO 249
<211> LENGTH: 112
<212> TYPE: PRT
<213> ORGANISM: mouse

<400> SEQUENCE: 249

```
Gly Ala Glu Leu Met Lys Pro Gly Ala Ser Val Lys Ile Ser Cys Lys
1               5                   10                  15

Ala Thr Gly Tyr Thr Phe Asn Thr Tyr Trp Ile Glu Trp Val Lys Gln
            20                  25                  30

Arg Pro Gly His Gly Leu Glu Trp Ile Gly Glu Ile Leu Pro Gly Thr
            35                  40                  45

Asp Asn Thr Asn Tyr Asn Glu Lys Phe Lys Gly Lys Ala Thr Phe Thr
        50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Phe Phe Asp Tyr Trp Gly Gln Gly Thr Thr Leu Thr Val Ser Ser
            100                 105                 110
```

<210> SEQ ID NO 250
<211> LENGTH: 112

```
<212> TYPE: PRT
<213> ORGANISM: mouse

<400> SEQUENCE: 250

Gly Ala Glu Leu Met Lys Pro Gly Ala Ser Val Lys Ile Ser Cys Lys
1               5                   10                  15

Ala Thr Gly Tyr Thr Phe Asn Thr Tyr Trp Ile Glu Trp Val Lys Gln
            20                  25                  30

Arg Pro Gly His Gly Leu Glu Trp Ile Gly Glu Ile Leu Pro Gly Thr
        35                  40                  45

Asp Asn Thr Asn Tyr Asn Glu Lys Phe Lys Gly Lys Ala Thr Phe Thr
    50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Phe Phe Asp Tyr Trp Gly Gln Gly Thr Thr Leu Thr Val Ser Ser
            100                 105                 110

<210> SEQ ID NO 251
<211> LENGTH: 112
<212> TYPE: PRT
<213> ORGANISM: mouse

<400> SEQUENCE: 251

Gly Ala Glu Leu Met Lys Pro Gly Ala Ser Val Lys Ile Ser Cys Lys
1               5                   10                  15

Ala Thr Gly Tyr Thr Phe Asn Thr Tyr Trp Ile Glu Trp Val Lys Gln
            20                  25                  30

Arg Pro Gly Arg Gly Leu Glu Trp Ile Gly Glu Ile Leu Pro Gly Thr
        35                  40                  45

Asp Asn Thr Asn Tyr Asn Glu Lys Phe Lys Gly Lys Ala Thr Phe Thr
    50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Phe Phe Asp Tyr Trp Gly Gln Gly Thr Thr Leu Thr Val Ser Ser
            100                 105                 110

<210> SEQ ID NO 252
<211> LENGTH: 112
<212> TYPE: PRT
<213> ORGANISM: mouse

<400> SEQUENCE: 252

Gly Ala Glu Leu Met Lys Pro Gly Ala Ser Val Lys Ile Ser Cys Lys
1               5                   10                  15

Ala Thr Gly Tyr Thr Leu Ser Ser Tyr Trp Ile Glu Trp Val Lys Gln
            20                  25                  30

Arg Pro Gly His Gly Leu Glu Trp Ile Gly Glu Ile Leu Pro Gly Ser
        35                  40                  45

Asp Asn Thr Asn Tyr Asn Glu Lys Phe Lys Gly Lys Ala Thr Phe Thr
    50                  55                  60

Ala Asp Thr Ser Ser Asn Ile Ala Tyr Met Gln Leu Ser Ser Leu Thr
65                  70                  75                  80

Ser Glu Asp Ser Ala Val Tyr Tyr Cys Ala Arg Gln Val Gly Leu Arg
```

```
                85                  90                  95
Trp Tyr Phe Asp Tyr Trp Gly Gln Gly Thr Thr Leu Thr Val Ser Ser
            100                 105                 110

<210> SEQ ID NO 253
<211> LENGTH: 112
<212> TYPE: PRT
<213> ORGANISM: mouse

<400> SEQUENCE: 253

Gly Ala Glu Leu Met Lys Pro Gly Ala Ser Val Lys Ile Ser Cys Lys
1               5                   10                  15

Ala Thr Gly Tyr Thr Leu Ser Ser Tyr Trp Ile Glu Trp Val Lys Gln
            20                  25                  30

Arg Pro Gly His Gly Leu Glu Trp Ile Gly Glu Ile Leu Pro Gly Ser
        35                  40                  45

Asp Asn Thr Asn Tyr Asn Glu Lys Phe Lys Gly Lys Ala Thr Phe Thr
    50                  55                  60

Ala Asp Thr Ser Ser Asn Ile Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Tyr Phe Asp Tyr Trp Gly Gln Gly Thr Thr Leu Thr Val Ser Ser
            100                 105                 110

<210> SEQ ID NO 254
<211> LENGTH: 112
<212> TYPE: PRT
<213> ORGANISM: mouse

<400> SEQUENCE: 254

Gly Ala Glu Leu Met Lys Pro Gly Ala Ser Val Lys Ile Ser Cys Lys
1               5                   10                  15

Ala Thr Gly Tyr Thr Leu Ser Ser Tyr Trp Ile Glu Trp Val Lys Gln
            20                  25                  30

Arg Pro Gly His Gly Leu Glu Trp Ile Gly Glu Ile Leu Pro Gly Ser
        35                  40                  45

Asp Asn Thr Asn Tyr Asn Glu Lys Phe Lys Gly Lys Ala Thr Phe Thr
    50                  55                  60

Ala Asp Thr Ser Ser Asn Ile Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Tyr Phe Asp Tyr Trp Gly Gln Gly Thr Thr Leu Thr Val Ser Ser
            100                 105                 110

<210> SEQ ID NO 255
<211> LENGTH: 112
<212> TYPE: PRT
<213> ORGANISM: mouse

<400> SEQUENCE: 255

Gly Ala Glu Leu Met Lys Pro Gly Ala Ser Val Lys Ile Ser Cys Lys
1               5                   10                  15

Ala Thr Gly Tyr Thr Leu Ser Ser Tyr Trp Ile Glu Trp Val Lys Gln
            20                  25                  30

Arg Pro Gly His Gly Leu Glu Trp Ile Gly Glu Ile Leu Pro Gly Ser
        35                  40                  45
```

```
Asp Asn Thr Asn Tyr Asn Glu Lys Phe Lys Gly Lys Ala Thr Phe Thr
    50                  55                  60

Ala Asp Thr Ser Ser Asn Ile Ala Tyr Met Gln Leu Ser Ser Leu Thr
65                  70                  75                  80

Ser Glu Asp Ser Ala Val Tyr Tyr Cys Ala Arg Gln Val Gly Leu Arg
                85                  90                  95

Trp Tyr Phe Asp Tyr Trp Gly Gln Gly Thr Thr Leu Thr Val Ser Ser
            100                 105                 110
```

<210> SEQ ID NO 256
<211> LENGTH: 119
<212> TYPE: PRT
<213> ORGANISM: mouse

<400> SEQUENCE: 256

```
Leu Val Asp Pro Gly Gly Gly Leu Val Gln Pro Gly Gly Ser Leu Arg
1               5                   10                  15

Leu Ser Cys Glu Thr Ser Gly Phe Thr Phe Thr Asp Tyr Tyr Leu Ser
                20                  25                  30

Trp Val Arg Gln Pro Pro Gly Lys Ala Leu Glu Trp Leu Gly Phe Ile
            35                  40                  45

Arg Asn Lys Ala Asn Gly Tyr Thr Thr Glu Tyr Ser Ala Ser Val Lys
    50                  55                  60

Gly Arg Phe Thr Ile Ser Arg Asp Asp Ser Gln Ser Ile Leu Tyr Leu
65                  70                  75                  80

Gln Met Asn Thr Leu Arg Ala Glu Asp Ser Ala Thr Tyr Tyr Cys Leu
                85                  90                  95

Arg Asn Gly Arg Pro Tyr Tyr Tyr Ala Leu Asp Tyr Trp Gly Gln Gly
            100                 105                 110

Thr Ser Val Ser Val Ser Ser
        115
```

<210> SEQ ID NO 257
<211> LENGTH: 115
<212> TYPE: PRT
<213> ORGANISM: mouse

<400> SEQUENCE: 257

```
Gly Gly Gly Leu Val Gln Pro Gly Gly Ser Leu Arg Leu Ser Cys Glu
1               5                   10                  15

Thr Ser Gly Phe Thr Phe Thr Asp Tyr Tyr Met Thr Trp Val Arg Gln
                20                  25                  30

Pro Pro Gly Lys Ala Leu Glu Trp Leu Gly Phe Ile Arg Asn Lys Ala
            35                  40                  45

Asn Gly Tyr Thr Thr Glu Tyr Ser Ala Ser Val Lys Gly Arg Phe Thr
    50                  55                  60

Ile Ser Arg Asp Asp Ser Gln Ser Ile Leu Tyr Leu Gln Met Asn Thr
65                  70                  75                  80

Leu Arg Ala Glu Asp Ser Ala Thr Tyr Tyr Cys Ser Arg Asn Gly Arg
                85                  90                  95

Pro Tyr Tyr Tyr Ala Leu Asp Tyr Trp Gly Gln Gly Thr Ser Val Ser
            100                 105                 110

Val Ser Ser
        115
```

<210> SEQ ID NO 258

```
<211> LENGTH: 115
<212> TYPE: PRT
<213> ORGANISM: mouse

<400> SEQUENCE: 258

Gly Gly Gly Leu Val Gln Pro Gly Gly Ser Leu Arg Leu Ser Cys Glu
1               5                   10                  15

Thr Ser Gly Phe Thr Phe Thr Asp Tyr Tyr Leu Ser Trp Val Arg Gln
            20                  25                  30

Pro Pro Gly Lys Ala Leu Glu Trp Leu Gly Phe Ile Arg Asn Lys Ala
        35                  40                  45

Asn Gly Tyr Thr Thr Glu Tyr Ser Ala Ser Val Lys Gly Arg Phe Thr
    50                  55                  60

Ile Ser Arg Asp Asp Ser Gln Ser Ile Leu Tyr Leu Gln Met Asn Thr
65                  70                  75                  80

Leu Arg Ala Glu Asp Ser Ala Thr Tyr Tyr Cys Ser Arg Asn Gly Arg
                85                  90                  95

Pro Tyr Tyr Tyr Ala Leu Asp Tyr Trp Gly Gln Gly Thr Ser Val Ser
            100                 105                 110

Val Ser Ser
        115

<210> SEQ ID NO 259
<211> LENGTH: 115
<212> TYPE: PRT
<213> ORGANISM: mouse

<400> SEQUENCE: 259

Gly Gly Gly Leu Val Gln Pro Gly Gly Ser Leu Arg Leu Ser Cys Glu
1               5                   10                  15

Thr Ser Gly Phe Thr Phe Thr Asp Tyr Tyr Leu Ser Trp Val Arg Gln
            20                  25                  30

Pro Pro Gly Lys Ala Leu Glu Trp Leu Gly Phe Ile Arg Asn Lys Ala
        35                  40                  45

Asn Gly Tyr Thr Thr Glu Tyr Ser Ala Ser Val Lys Gly Arg Phe Thr
    50                  55                  60

Ile Ser Arg Asp Asp Ser Gln Ser Ile Leu Tyr Leu Gln Met Asn Thr
65                  70                  75                  80

Leu Arg Ala Glu Asp Ser Ala Thr Tyr Tyr Cys Leu Arg Asn Gly Arg
                85                  90                  95

Pro Tyr Tyr Tyr Ala Leu Asp Tyr Trp Gly Gln Gly Thr Ser Val Ser
            100                 105                 110

Val Ser Ser
        115

<210> SEQ ID NO 260
<211> LENGTH: 113
<212> TYPE: PRT
<213> ORGANISM: mouse

<400> SEQUENCE: 260

Gly Thr Glu Leu Met Lys Pro Gly Ala Ser Val Lys Ile Ser Cys Arg
1               5                   10                  15

Ala Thr Gly Tyr Thr Phe Ser Asp Tyr Trp Ile Glu Trp Val Lys Gln
            20                  25                  30

Arg Pro Gly His Gly Leu Glu Trp Ile Gly Glu Ile Leu Pro Gly Ser
        35                  40                  45
```

-continued

```
Gly Asp Thr Asn Tyr Asn Glu Lys Phe Lys Gly Lys Ala Thr Phe Thr
            50                  55                  60

Ala Asp Thr Ser Ser Asn Thr Ala Tyr Met Gln Leu Ser Ser Leu Thr
 65                  70                  75                  80

Ser Glu Asp Ser Ala Val Tyr Tyr Cys Ala Arg Gly Leu Trp Leu Arg
                 85                  90                  95

Gly Tyr Tyr Phe Asp Tyr Trp Gly Gln Gly Thr Thr Leu Thr Val Ser
            100                 105                 110

Ser

<210> SEQ ID NO 261
<211> LENGTH: 113
<212> TYPE: PRT
<213> ORGANISM: mouse

<400> SEQUENCE: 261

Gly Thr Glu Leu Met Lys Pro Gly Ala Ser Val Lys Ile Ser Cys Arg
  1               5                  10                  15

Ala Thr Gly Tyr Thr Phe Ser Asp Tyr Trp Ile Glu Trp Val Lys Gln
                 20                  25                  30

Arg Pro Gly His Gly Leu Glu Trp Ile Gly Glu Ile Leu Pro Gly Ser
             35                  40                  45

Gly Asp Thr Asn Tyr Asn Glu Lys Phe Lys Gly Lys Ala Thr Phe Thr
         50                  55                  60

Ala Asp Thr Ser Ser Asn Thr Ala Tyr Met Gln Leu Ser Ser Leu Thr
 65                  70                  75                  80

Ser Glu Asp Ser Ala Val Tyr Tyr Cys Ala Arg Gly Leu Trp Leu Arg
                 85                  90                  95

Gly Tyr Tyr Phe Asp Tyr Trp Gly Gln Gly Thr Thr Leu Thr Val Ser
            100                 105                 110

Ser

<210> SEQ ID NO 262
<211> LENGTH: 113
<212> TYPE: PRT
<213> ORGANISM: mouse

<400> SEQUENCE: 262

Gly Thr Glu Leu Met Lys Pro Gly Ala Ser Val Lys Ile Ser Cys Arg
  1               5                  10                  15

Ala Thr Gly Tyr Thr Phe Ser Asp Tyr Trp Ile Glu Trp Val Lys Gln
                 20                  25                  30

Arg Pro Gly His Gly Leu Glu Trp Ile Gly Glu Ile Leu Pro Gly Ser
             35                  40                  45

Gly Asp Thr Asn Tyr Asn Glu Lys Phe Lys Gly Lys Ala Thr Phe Thr
         50                  55                  60

Ala Asp Thr Ser Ser Asn Thr Ala Tyr Met Gln Leu Ser Ser Leu Thr
 65                  70                  75                  80

Ser Glu Asp Ser Ala Val Tyr Tyr Cys Ala Arg Gly Leu Trp Leu Arg
                 85                  90                  95

Gly Tyr Tyr Phe Asp Tyr Trp Gly Gln Gly Thr Thr Leu Thr Val Ser
            100                 105                 110

Ser

<210> SEQ ID NO 263
<211> LENGTH: 118
```

```
<212> TYPE: PRT
<213> ORGANISM: mouse

<400> SEQUENCE: 263

Gln Leu Gln Gln Ser Gly Thr Glu Leu Met Lys Pro Gly Ala Ser Val
1               5                   10                  15

Lys Ile Ser Cys Arg Ala Thr Gly Tyr Thr Phe Ser Asp Tyr Trp Ile
            20                  25                  30

Glu Trp Val Lys Gln Arg Pro Gly His Gly Leu Glu Trp Ile Gly Glu
        35                  40                  45

Ile Leu Pro Gly Ser Gly Asp Thr Asn Tyr Asn Glu Lys Phe Lys Gly
50                  55                  60

Lys Ala Thr Phe Thr Ala Asp Thr Ser Ser Asn Thr Ala Tyr Met Gln
65                  70                  75                  80

Leu Ser Ser Leu Thr Ser Glu Asp Ser Ala Val Tyr Tyr Cys Ala Arg
                85                  90                  95

Gly Leu Trp Leu Arg Gly Tyr Tyr Phe Asp Tyr Trp Gly Gln Gly Thr
            100                 105                 110

Thr Leu Thr Val Ser Ser
        115

<210> SEQ ID NO 264
<211> LENGTH: 113
<212> TYPE: PRT
<213> ORGANISM: mouse

<400> SEQUENCE: 264

Gly Thr Glu Leu Met Lys Pro Gly Ala Ser Val Lys Ile Ser Cys Arg
1               5                   10                  15

Ser Thr Gly Tyr Thr Phe Ser Ser Tyr Trp Ile Glu Trp Tyr Lys Gln
            20                  25                  30

Arg Pro Gly His Gly Leu Glu Trp Ile Gly Glu Ile Leu Pro Gly Ser
        35                  40                  45

Gly Asp Thr Asn Tyr Asn Glu Lys Phe Lys Gly Lys Ala Thr Phe Thr
    50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Arg Gly Leu Trp Leu Arg
                85                  90                  95

Gly Tyr Tyr Phe Asp Tyr Trp Gly Gln Gly Thr Thr Leu Thr Val Ser
            100                 105                 110

Ser

<210> SEQ ID NO 265
<211> LENGTH: 115
<212> TYPE: PRT
<213> ORGANISM: mouse

<400> SEQUENCE: 265

Gly Gly Gly Leu Val Gln Pro Gly Asn Ser Leu Arg Leu Ser Cys Ala
1               5                   10                  15

Thr Ser Gly Phe Thr Phe Thr Asp Tyr Tyr Leu Ser Trp Val Arg Gln
            20                  25                  30

Pro Pro Gly Lys Ala Leu Glu Trp Leu Gly Phe Ile Arg Asn Lys Gly
        35                  40                  45

Asn Gly Tyr Thr Thr Glu Tyr Ser Ala Ser Val Lys Gly Arg Phe Thr
    50                  55                  60
```

```
Ile Ser Arg Asp Asp Ser Gln Ser Ile Leu Tyr Leu Gln Met Asn Thr
 65                  70                  75                  80

Leu Arg Ala Glu Asp Ser Ala Thr Tyr Tyr Cys Ala Arg His Gly Arg
                 85                  90                  95

Pro Tyr Tyr Tyr Leu Met Asp Tyr Trp Gly Gln Gly Thr Ser Val Thr
            100                 105                 110

Val Ser Ser
        115

<210> SEQ ID NO 266
<211> LENGTH: 115
<212> TYPE: PRT
<213> ORGANISM: mouse

<400> SEQUENCE: 266

Gly Gly Gly Leu Val Gln Pro Gly Asn Ser Leu Arg Leu Ser Cys Ala
  1               5                  10                  15

Thr Ser Gly Phe Thr Phe Thr Asp Tyr Tyr Leu Ser Trp Val Arg Gln
                 20                  25                  30

Pro Pro Gly Lys Ala Leu Glu Trp Leu Gly Phe Ile Arg Asn Lys Gly
             35                  40                  45

Asn Gly Tyr Thr Thr Glu Tyr Ser Ala Ser Val Lys Gly Arg Phe Thr
 50                  55                  60

Ile Ser Arg Asp Asp Ser Gln Ser Ile Leu Tyr Leu Gln Met Asn Thr
 65                  70                  75                  80

Leu Arg Ala Glu Asp Ser Ala Thr Tyr Tyr Cys Ala Arg His Gly Arg
                 85                  90                  95

Pro Tyr Tyr Tyr Leu Met Asp Tyr Trp Gly Gln Gly Thr Ser Val Thr
            100                 105                 110

Val Ser Ser
        115

<210> SEQ ID NO 267
<211> LENGTH: 115
<212> TYPE: PRT
<213> ORGANISM: mouse

<400> SEQUENCE: 267

Gly Gly Gly Leu Val Gln Pro Gly Asn Ser Leu Arg Leu Ser Cys Ala
  1               5                  10                  15

Ser Ser Gly Phe Thr Phe Thr Asp Tyr Tyr Met Ser Trp Val Arg Gln
                 20                  25                  30

Pro Pro Gly Lys Ala Leu Glu Trp Leu Gly Phe Ile Arg Asn Lys Ala
             35                  40                  45

Asn Gly Tyr Thr Thr Glu Tyr Ser Ala Ser Ala Lys Gly Arg Phe Thr
 50                  55                  60

Ile Ser Arg Asp Asp Ser Gln Ser Ile Leu Tyr Leu Gln Met Asn Thr
 65                  70                  75                  80

Leu Arg Ala Glu Asp Ser Ala Thr Tyr Tyr Cys Ala Arg His Gly Arg
                 85                  90                  95

Pro Tyr Tyr Tyr Leu Met Asp Tyr Trp Gly Gln Gly Thr Ser Val Thr
            100                 105                 110

Val Ser Ser
        115

<210> SEQ ID NO 268
```

```
<211> LENGTH: 117
<212> TYPE: PRT
<213> ORGANISM: mouse

<400> SEQUENCE: 268

His Gln Gln Ser Gly Ala Glu Leu Met Lys Pro Gly Ala Ser Val Lys
1               5                   10                  15

Ile Ser Cys Lys Ser Thr Gly Tyr Thr Phe Ser Ser Tyr Trp Ile Glu
            20                  25                  30

Trp Ile Lys Gln Arg Pro Gly His Gly Leu Glu Trp Ile Gly Glu Ile
        35                  40                  45

Leu Pro Gly Ser Gly Phe Thr Asn Tyr Asn Glu Asn Phe Lys Gly Lys
    50                  55                  60

Val Thr Phe Thr Ala Asp Thr Ser Ser Asn Thr Ala Tyr Met Gln Phe
65                  70                  75                  80

Ser Ser Leu Thr Ser Glu Asp Ser Ala Val Tyr Tyr Cys Ala Thr Thr
                85                  90                  95

Thr Val Val Val Arg Asp Tyr Leu Asp Tyr Trp Gly Gln Gly Thr Thr
            100                 105                 110

Leu Thr Val Ser Ser
        115

<210> SEQ ID NO 269
<211> LENGTH: 113
<212> TYPE: PRT
<213> ORGANISM: mouse

<400> SEQUENCE: 269

Gly Ala Glu Leu Met Lys Pro Gly Ala Ser Val Lys Ile Ser Cys Lys
1               5                   10                  15

Ala Thr Gly Tyr Thr Phe Ser Ser Tyr Trp Ile Glu Trp Ile Lys Gln
            20                  25                  30

Arg Pro Gly His Gly Leu Glu Trp Ile Gly Glu Ile Leu Pro Gly Ser
        35                  40                  45

Gly Phe Thr Asn Tyr Asn Glu Asn Phe Lys Gly Lys Val Thr Phe Ser
    50                  55                  60

Ala Asp Thr Ser Ser Asn Thr Ala Tyr Met Gln Leu Ser Ser Leu Thr
65                  70                  75                  80

Ser Glu Asp Ser Ala Val Tyr Tyr Cys Ala Thr Thr Val Val Val
                85                  90                  95

Arg Asp Tyr Leu Asp Tyr Trp Gly Gln Gly Thr Thr Leu Thr Val Ser
            100                 105                 110

Ser

<210> SEQ ID NO 270
<211> LENGTH: 109
<212> TYPE: PRT
<213> ORGANISM: mouse

<400> SEQUENCE: 270

Ser Arg Gln Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Met His Trp Tyr Gln Gln Lys Ser Ser Thr Ser Pro Lys Leu Trp
        35                  40                  45

Ile Tyr Asp Thr Ser Lys Leu Ala Ser Gly Val Pro Gly Arg Phe Ser
```

```
            50                  55                  60
Gly Ser Gly Ser Gly Asn Ser Tyr Ser Leu Thr Ile Ser Ser Met Glu
 65                  70                  75                  80

Ala Glu Asp Val Ala Thr Tyr Tyr Cys Phe Gln Gly Ser Gly Tyr Pro
                 85                  90                  95

Leu Thr Phe Gly Ala Gly Thr Lys Leu Glu Leu Lys Arg
            100                 105

<210> SEQ ID NO 271
<211> LENGTH: 109
<212> TYPE: PRT
<213> ORGANISM: mouse

<400> SEQUENCE: 271

Ser Arg Gln Ile Val Leu Thr Gln Ser Pro Ala Ile Met Ser Ala Ser
 1               5                  10                  15

Pro Gly Glu Lys Val Thr Met Thr Cys Ser Ala Ser Ser Ser Val Ser
                 20                  25                  30

Tyr Met His Trp Tyr Gln Gln Lys Ser Ser Thr Ser Pro Lys Leu Trp
             35                  40                  45

Ile Tyr Asp Thr Ser Lys Leu Ala Ser Gly Val Pro Gly Arg Phe Ser
         50                  55                  60

Gly Ser Gly Ser Gly Asn Ser Tyr Ser Leu Thr Ile Ser Ser Met Glu
 65                  70                  75                  80

Ala Glu Asp Val Ala Thr Tyr Tyr Cys Phe Gln Gly Ser Gly Tyr Pro
                 85                  90                  95

Leu Thr Phe Gly Ser Gly Thr Lys Leu Glu Ile Lys Arg
            100                 105

<210> SEQ ID NO 272
<211> LENGTH: 109
<212> TYPE: PRT
<213> ORGANISM: mouse

<400> SEQUENCE: 272

Ser Arg Gln Ile Val Leu Thr Gln Ser Pro Ala Ile Met Ser Ala Ser
 1               5                  10                  15

Pro Gly Glu Lys Val Thr Met Thr Cys Ser Ala Ser Ser Ser Val Asn
                 20                  25                  30

Tyr Met His Trp Tyr Gln Gln Lys Ser Gly Thr Ser Pro Lys Arg Trp
             35                  40                  45

Ile Tyr Asp Thr Ser Lys Leu Thr Ser Gly Val Pro Ala Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Asn Arg Asn Pro
                 85                  90                  95

Pro Thr Phe Gly Gly Gly Thr Lys Leu Glu Ile Lys Arg
            100                 105

<210> SEQ ID NO 273
<211> LENGTH: 109
<212> TYPE: PRT
<213> ORGANISM: mouse

<400> SEQUENCE: 273

Ser Arg Gln Ile Val Leu Thr Gln Ser Pro Ala Ile Met Ser Ala Ser
 1               5                  10                  15
```

-continued

Pro Gly Glu Lys Val Thr Met Thr Cys Ser Ala Asn Ser Ser Val Ser
             20                  25                  30

Tyr Met His Trp Tyr Gln Gln Lys Ser Gly Thr Ser Pro Lys Arg Trp
         35                  40                  45

Ile Tyr Asp Thr Ser Lys Leu Ala Ser Gly Val Pro Ala Arg Phe Ser
     50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Asn Arg Asn Pro
                 85                  90                  95

Pro Thr Phe Gly Gly Gly Thr Lys Leu Glu Ile Lys Arg
             100                 105

<210> SEQ ID NO 274
<211> LENGTH: 109
<212> TYPE: PRT
<213> ORGANISM: mouse

<400> SEQUENCE: 274

Ser Arg Gln Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
             20                  25                  30

Tyr Met His Trp Tyr Gln Gln Lys Ser Ser Thr Ser Pro Lys Leu Trp
         35                  40                  45

Ile Tyr Asp Thr Ser Lys Leu Ala Ser Gly Val Pro Gly Arg Phe Ser
     50                  55                  60

Gly Ser Gly Ser Gly Asn Ser Tyr Ser Leu Thr Ile Ser Ser Met Glu
65                  70                  75                  80

Ala Glu Asp Val Ala Thr Tyr Tyr Cys Phe Gln Gly Ser Gly Tyr Pro
                 85                  90                  95

Leu Thr Phe Gly Ser Gly Thr Lys Leu Glu Ile Lys Arg
             100                 105

<210> SEQ ID NO 275
<211> LENGTH: 109
<212> TYPE: PRT
<213> ORGANISM: mouse

<400> SEQUENCE: 275

Ser Arg Gln Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
             20                  25                  30

Tyr Met His Trp Tyr Gln Gln Lys Ser Ser Thr Ser Pro Lys Leu Trp
         35                  40                  45

Ile Tyr Asp Thr Ser Lys Leu Ala Ser Gly Val Pro Gly Arg Phe Ser
     50                  55                  60

Gly Ser Gly Ser Gly Asn Thr Tyr Ser Leu Thr Ile Ser Ser Met Glu
65                  70                  75                  80

Ala Glu Asp Val Ala Thr Tyr Tyr Cys Phe Gln Gly Ser Gly Tyr Pro
                 85                  90                  95

Leu Thr Phe Gly Ser Gly Thr Lys Leu Glu Ile Lys Arg
             100                 105

<210> SEQ ID NO 276

```
<211> LENGTH: 110
<212> TYPE: PRT
<213> ORGANISM: mouse

<400> SEQUENCE: 276

Ser Arg Asp Ile Gln Met Thr Gln Ser Pro Ala Ser Leu Ser Ala Ser
1               5                   10                  15

Val Gly Glu Thr Val Thr Ile Thr Cys Arg Ala Ser Glu Asn Ile Asn
            20                  25                  30

Ser Tyr Leu Ala Trp Phe Gln Gln Lys Gln Gly Lys Ser Pro Gln Leu
        35                  40                  45

Leu Val Tyr Asp Ala Lys Thr Leu Ala Glu Gly Val Pro Ser Arg Phe
    50                  55                  60

Ser Gly Ser Gly Ser Gly Thr Gln Phe Ser Leu Lys Ile Asn Ser Leu
65                  70                  75                  80

Gln Pro Glu Asp Phe Gly Ser Tyr Tyr Cys Gln His His Tyr Gly Ile
                85                  90                  95

Pro Leu Thr Phe Gly Ala Gly Thr Lys Leu Glu Leu Lys Arg
            100                 105                 110

<210> SEQ ID NO 277
<211> LENGTH: 110
<212> TYPE: PRT
<213> ORGANISM: mouse

<400> SEQUENCE: 277

Ser Arg Asp Ile Gln Met Thr Gln Ser Pro Ala Ser Leu Ser Ala Ser
1               5                   10                  15

Val Gly Glu Thr Val Thr Ile Thr Cys Arg Ala Ser Glu Asn Ile Asn
            20                  25                  30

Ser Tyr Leu Ala Trp Phe Gln Gln Lys Gln Gly Lys Ser Pro Gln Leu
        35                  40                  45

Leu Val Tyr Asp Ala Lys Thr Leu Ala Glu Gly Val Pro Ser Arg Phe
    50                  55                  60

Ser Gly Ser Gly Ser Gly Thr Gln Phe Ser Leu Lys Ile Asn Ser Leu
65                  70                  75                  80

Gln Pro Glu Asp Phe Gly Ser Tyr Tyr Cys Gln His His Tyr Gly Ile
                85                  90                  95

Pro Leu Thr Phe Gly Ala Gly Thr Lys Leu Glu Leu Lys Arg
            100                 105                 110

<210> SEQ ID NO 278
<211> LENGTH: 110
<212> TYPE: PRT
<213> ORGANISM: mouse

<400> SEQUENCE: 278

Ser Arg Asp Ile Gln Met Thr Gln Ser Pro Ala Ser Leu Ser Ala Ser
1               5                   10                  15

Val Gly Glu Thr Val Thr Ile Thr Cys Arg Ala Ser Glu Asn Ile Asn
            20                  25                  30

Ser Tyr Leu Ala Trp Phe Gln Gln Lys Gln Gly Lys Ser Pro Gln Leu
        35                  40                  45

Leu Val Tyr Asp Ala Lys Thr Leu Ala Glu Gly Val Pro Ser Arg Phe
    50                  55                  60

Ser Gly Ser Gly Ser Gly Thr Gln Phe Ser Leu Lys Ile Asn Ser Leu
65                  70                  75                  80
```

```
Gln Pro Glu Asp Phe Gly Ser Tyr Tyr Cys Gln His His Tyr Gly Ile
            85                  90                  95
Pro Leu Thr Phe Gly Ala Gly Thr Lys Leu Glu Leu Lys Arg
            100                 105                 110
```

<210> SEQ ID NO 279
<211> LENGTH: 26
<212> TYPE: DNA
<213> ORGANISM: artificial sequence
<220> FEATURE:
<223> OTHER INFORMATION: restriction oligonucleotide

<400> SEQUENCE: 279
tccggggacc tgtacaccac gagcag                                         26

<210> SEQ ID NO 280
<211> LENGTH: 48
<212> TYPE: DNA
<213> ORGANISM: artificial sequence
<220> FEATURE:
<223> OTHER INFORMATION: primer

<400> SEQUENCE: 280
gtgctggccg ttggaagagg agtgctcgag caggtkcagc tggtgcag                 48

<210> SEQ ID NO 281
<211> LENGTH: 48
<212> TYPE: DNA
<213> ORGANISM: artificial sequence
<220> FEATURE:
<223> OTHER INFORMATION: primer

<400> SEQUENCE: 281
gtgctggccg ttggaagagg agtgctcgag caggtccagc ttgtgcag                 48

<210> SEQ ID NO 282
<211> LENGTH: 48
<212> TYPE: DNA
<213> ORGANISM: artificial sequence
<220> FEATURE:
<223> OTHER INFORMATION: primer

<400> SEQUENCE: 282
gtgctggccg ttggaagagg agtgctcgag saggtccagc tggtacag                 48

<210> SEQ ID NO 283
<211> LENGTH: 48
<212> TYPE: DNA
<213> ORGANISM: artificial sequence
<220> FEATURE:
<223> OTHER INFORMATION: primer

<400> SEQUENCE: 283
gtgctggccg ttggaagagg agtgctcgag caratgcagc tggtgcag                 48

<210> SEQ ID NO 284
<211> LENGTH: 48
<212> TYPE: DNA
<213> ORGANISM: artificial sequence
<220> FEATURE:
<223> OTHER INFORMATION: primer

<400> SEQUENCE: 284
gtgctggccg ttggaagagg agtgctcgag cagatcacct tgaaggag                 48

```
<210> SEQ ID NO 285
<211> LENGTH: 48
<212> TYPE: DNA
<213> ORGANISM: artificial sequence
<220> FEATURE:
<223> OTHER INFORMATION: primer

<400> SEQUENCE: 285
gtgctggccg ttggaagagg agtgctcgag caggtcacct tgarggag          48

<210> SEQ ID NO 286
<211> LENGTH: 48
<212> TYPE: DNA
<213> ORGANISM: artificial sequence
<220> FEATURE:
<223> OTHER INFORMATION: primer

<400> SEQUENCE: 286
gtgctggccg ttggaagagg agtgctcgag gargtgcagc tggtggag          48

<210> SEQ ID NO 287
<211> LENGTH: 48
<212> TYPE: DNA
<213> ORGANISM: artificial sequence
<220> FEATURE:
<223> OTHER INFORMATION: primer

<400> SEQUENCE: 287
gtgctggccg ttggaagagg agtgctcgag caggtgcagc tggtggag          48

<210> SEQ ID NO 288
<211> LENGTH: 48
<212> TYPE: DNA
<213> ORGANISM: artificial sequence
<220> FEATURE:
<223> OTHER INFORMATION: primer

<400> SEQUENCE: 288
gtgctggccg ttggaagagg agtgctcgag gaggtgcagc tgttggag          48

<210> SEQ ID NO 289
<211> LENGTH: 48
<212> TYPE: DNA
<213> ORGANISM: artificial sequence
<220> FEATURE:
<223> OTHER INFORMATION: primer

<400> SEQUENCE: 289
gtgctggccg ttggaagagg agtgctcgag cagstgcagc tgcaggag          48

<210> SEQ ID NO 290
<211> LENGTH: 48
<212> TYPE: DNA
<213> ORGANISM: artificial sequence
<220> FEATURE:
<223> OTHER INFORMATION: primer

<400> SEQUENCE: 290
gtgctggccg ttggaagagg agtgctcgag caggtgcagc tacagcag          48

<210> SEQ ID NO 291
<211> LENGTH: 48
<212> TYPE: DNA
<213> ORGANISM: artificial sequence
<220> FEATURE:
<223> OTHER INFORMATION: primer
```

<400> SEQUENCE: 291
gtgctggccg ttggaagagg agtgctcgag gargtgcagc tggtgcag 48

<210> SEQ ID NO 292
<211> LENGTH: 48
<212> TYPE: DNA
<213> ORGANISM: artificial sequence
<220> FEATURE:
<223> OTHER INFORMATION: primer

<400> SEQUENCE: 292
gtgctggccg ttggaagagg agtgctcgag caggtacagc tgcagcag 48

<210> SEQ ID NO 293
<211> LENGTH: 48
<212> TYPE: DNA
<213> ORGANISM: artificial sequence
<220> FEATURE:
<223> OTHER INFORMATION: primer

<400> SEQUENCE: 293
gtgctggccg ttggaagagg agtgctcgag caggtscagc tggtgcaa 48

<210> SEQ ID NO 294
<211> LENGTH: 51
<212> TYPE: DNA
<213> ORGANISM: artificial sequence
<220> FEATURE:
<223> OTHER INFORMATION: extension oligonucleotide

<400> SEQUENCE: 294
gtgctggccg ttggaagagg agtgcctgta caggtccccg gaggcatcct c 51

<210> SEQ ID NO 295
<211> LENGTH: 24
<212> TYPE: DNA
<213> ORGANISM: artificial sequence
<220> FEATURE:
<223> OTHER INFORMATION: primer

<400> SEQUENCE: 295
gtgctggccg ttggaagagg agtg 24

<210> SEQ ID NO 296
<211> LENGTH: 24
<212> TYPE: DNA
<213> ORGANISM: artificial sequence
<220> FEATURE:
<223> OTHER INFORMATION: primer

<400> SEQUENCE: 296
ctcgagcagg tkcagctggt gcag 24

<210> SEQ ID NO 297
<211> LENGTH: 24
<212> TYPE: DNA
<213> ORGANISM: artificial sequence
<220> FEATURE:
<223> OTHER INFORMATION: primer

<400> SEQUENCE: 297
ctcgagcagg tccagcttgt gcag 24

<210> SEQ ID NO 298
<211> LENGTH: 24

```
<210> SEQ ID NO 299
<211> LENGTH: 24
<212> TYPE: DNA
<213> ORGANISM: artificial sequence
<220> FEATURE:
<223> OTHER INFORMATION: primer

<400> SEQUENCE: 298
ctcgagsagg tccagctggt acag                                          24

<210> SEQ ID NO 299
<211> LENGTH: 24
<212> TYPE: DNA
<213> ORGANISM: artificial sequence
<220> FEATURE:
<223> OTHER INFORMATION: primer

<400> SEQUENCE: 299
ctcgagcara tgcagctggt gcag                                          24

<210> SEQ ID NO 300
<211> LENGTH: 24
<212> TYPE: DNA
<213> ORGANISM: artificial sequence
<220> FEATURE:
<223> OTHER INFORMATION: primer

<400> SEQUENCE: 300
ctcgagcaga tcaccttgaa ggag                                          24

<210> SEQ ID NO 301
<211> LENGTH: 24
<212> TYPE: DNA
<213> ORGANISM: artificial sequence
<220> FEATURE:
<223> OTHER INFORMATION: primer

<400> SEQUENCE: 301
ctcgagcagg tcaccttgar ggag                                          24

<210> SEQ ID NO 302
<211> LENGTH: 24
<212> TYPE: DNA
<213> ORGANISM: artificial sequence
<220> FEATURE:
<223> OTHER INFORMATION: primer

<400> SEQUENCE: 302
ctcgaggarg tgcagctggt ggag                                          24

<210> SEQ ID NO 303
<211> LENGTH: 24
<212> TYPE: DNA
<213> ORGANISM: artificial sequence
<220> FEATURE:
<223> OTHER INFORMATION: primer

<400> SEQUENCE: 303
ctcgagcagg tgcagctggt ggag                                          24

<210> SEQ ID NO 304
<211> LENGTH: 24
<212> TYPE: DNA
<213> ORGANISM: artificial sequence
<220> FEATURE:
<223> OTHER INFORMATION: primer

<400> SEQUENCE: 304
```
ctcgaggagg tgcagctgtt ggag                                      24

<210> SEQ ID NO 305
<211> LENGTH: 24
<212> TYPE: DNA
<213> ORGANISM: artificial sequence
<220> FEATURE:
<223> OTHER INFORMATION: primer

<400> SEQUENCE: 305
ctcgagcags tgcagctgca ggag                                      24

<210> SEQ ID NO 306
<211> LENGTH: 24
<212> TYPE: DNA
<213> ORGANISM: artificial sequence
<220> FEATURE:
<223> OTHER INFORMATION: primer

<400> SEQUENCE: 306
ctcgagcagg tgcagctaca gcag                                      24

<210> SEQ ID NO 307
<211> LENGTH: 24
<212> TYPE: DNA
<213> ORGANISM: artificial sequence
<220> FEATURE:
<223> OTHER INFORMATION: primer

<400> SEQUENCE: 307
ctcgaggarg tgcagctggt gcag                                      24

<210> SEQ ID NO 308
<211> LENGTH: 24
<212> TYPE: DNA
<213> ORGANISM: artificial sequence
<220> FEATURE:
<223> OTHER INFORMATION: primer

<400> SEQUENCE: 308
ctcgagcagg tacagctgca gcag                                      24

<210> SEQ ID NO 309
<211> LENGTH: 24
<212> TYPE: DNA
<213> ORGANISM: artificial sequence
<220> FEATURE:
<223> OTHER INFORMATION: primer

<400> SEQUENCE: 309
ctcgagcagg tscagctggt gcaa                                      24